US010513693B2

(12) United States Patent
Dantas Costa et al.

(10) Patent No.: US 10,513,693 B2
(45) Date of Patent: Dec. 24, 2019

(54) USE OF GLYCEROL WITH LIMITED FEED OF CARBOHYDRATES FOR FERMENTATION

(71) Applicant: BASF SE, Ludwigshafen (DE)

(72) Inventors: Esther Dantas Costa, Mannheim (DE); Oskar Zelder, Speyer (DE); Hartwig Schröder, NuBloch (DE); Stefan Haefner, Speyer (DE); Joanna Martyna Krawczyk, Mannheim (DE); Gregory Von Abendroth, Tarrytown, NY (US); Christian Riedele, Eppelheim (DE); Torsten Renz, Hochdorf-Assenheim (DE)

(73) Assignee: BASF SE, Ludwigshafen (DE)

( * ) Notice: Subject to any disclaimer, the term of this patent is extended or adjusted under 35 U.S.C. 154(b) by 171 days.

(21) Appl. No.: 15/127,181

(22) PCT Filed: Mar. 18, 2015

(86) PCT No.: PCT/EP2015/055717
§ 371 (c)(1),
(2) Date: Sep. 19, 2016

(87) PCT Pub. No.: WO2015/140226
PCT Pub. Date: Sep. 24, 2015

(65) Prior Publication Data
US 2018/0030418 A1 Feb. 1, 2018

(30) Foreign Application Priority Data
Mar. 19, 2014 (EP) .................... 14160638

(51) Int. Cl.
*C12N 9/04* (2006.01)
*C12N 9/10* (2006.01)
*C12P 7/46* (2006.01)
*C07K 14/285* (2006.01)

(52) U.S. Cl.
CPC ......... *C12N 9/0006* (2013.01); *C12N 9/1029* (2013.01); *C12P 7/46* (2013.01); *C12Y 101/01027* (2013.01); *C12Y 203/01054* (2013.01); *C07K 14/285* (2013.01)

(58) Field of Classification Search
None
See application file for complete search history.

(56) References Cited

U.S. PATENT DOCUMENTS 8,883,466 B2 * 11/2014 Scholten ............. C12N 9/0006
435/145
9,023,632 B2 * 5/2015 Schroder .................. C12N 1/32
435/183
2010/0159543 A1 6/2010 Scholten et al.
2014/0235815 A1 * 8/2014 Burgard .................. C07C 55/10
528/271
2016/0348082 A1 * 12/2016 Krawczyk ............ C12N 9/1205
2017/0073665 A1 * 3/2017 Krawczyk ............ C12Y 207/11

FOREIGN PATENT DOCUMENTS

| EP | 2204443 A1 | 7/2010 |
| EP | 2612905 A2 | 7/2013 |
| WO | WO-2005/052135 A1 | 6/2005 |
| WO | WO-2009/024294 A1 | 2/2009 |
| WO | WO-2010/092155 A1 | 8/2010 |

OTHER PUBLICATIONS

Fan et al., Process optimization with alternative carbon sources and modulation of secondary metabolism for enhanced ansamitocin P-3 production in Actinosynnema pretiosum, J. Biotechnol., 192:1-10 (2014).
International Preliminary Report on Patentability, International Application No. PCT/EP2015/055717, dated Sep. 20, 2016.
International Search Report and Written Opinion, International Application No. PCT/EP2015/055717, dated May 22, 2015.
Kuhnert et al., *Basfia succiniciproducens* gen. nov., sp., nov., a new member of the family Pasteurellaceae isolated from bovine rumen, Int. J. Systematic and Evolutionary Microbiology, 60(1):44-50 (2010).
Scholten et al., Continuous cultivation approach for fermentative succinic acid production from crude glycerol by Basfia succiniciproducens DD1, Biotechnology Letters, 31(12):1947-51 (2009).
Japanese Patent Application No. 2016-558086, Notice of Reasons for Rejection, dated Mar. 12, 2019.
Liu et al., Glycerol/glucose co-fermentation: one more proficient process to produce propionic acid by *Propionibacterium acidipropionici*, Curr. Microbiol., 62(1):152-8 (Jan. 2011).

(Continued)

*Primary Examiner* — Anand U Desai
(74) *Attorney, Agent, or Firm* — Marshall, Gerstein & Borun LLP

(57) ABSTRACT

The present invention relates to a process for producing an organic acid by fermentation, comprising the process steps: I) cultivating microorganisms in a culture medium to which are fed, as assimilable carbon sources, glycerol and a further carbonaceous compound, to allow the microorganisms to produce the organic acid, thereby obtaining a fermentation broth comprising the organic acid; II) recovering the organic acid or the salt thereof from the fermentation broth obtained in process step I); wherein, at least for a certain period of time in process step I), the consumption rate of the further carbonaceous compound ($C_{Rc.c.}$; in g per liter per hour) is lower than the maximum theoretical consumption rate of the further carbonaceous compound ($CR_{c.c.\ max}$; in g per liter per hour).

10 Claims, 4 Drawing Sheets
Specification includes a Sequence Listing.

(56) References Cited

OTHER PUBLICATIONS

Saint-Amans et al., Regulation of carbon and electron flow in *Clostridium butyricum* VPI 3266 grown on glucose-glycerol mixtures, J. Bacteriol., 183(5):1748-54 (Mar. 2001).
Temudo et al., Glycerol fermentation by (open) mixed cultures: a chemostat study, Biotechnol. Bioeng., 100(6):1088-98 (Aug. 2008).
Wang et al., Propionic acid production in glycerol/glucose co-fermentation by *Propionibacterium freudenreichii* subsp. *shermanii*, Bioresour. Technol., 137:116-23 (Jun. 2013).

* cited by examiner

USE OF GLYCEROL WITH LIMITED FEED OF CARBOHYDRATES FOR FERMENTATION

This application is a National Stage application of International Application No. PCT/EP2015/055717, filed Mar. 18, 2015, which claims priority under 35 U.S.C. § 119 to European Patent Application No. 14160638.4, filed Mar. 19, 2014.

INCORPORATION BY REFERENCE OF MATERIAL SUBMITTED ELECTRONICALLY

This application incorporates by reference in its entirety a computer-readable nucleotide/amino acid sequence listing identified as one 58,813 byte ASCII (text) file named "H75743_SubSeqListing.txt," created Sep. 19, 2016.

The present invention relates to a process for producing an organic acid by fermentation.

Organic compounds such as small dicarboxylic acids having 6 or fewer carbons are commercially significant chemicals with many uses. For example, the small diacids include 1,4-diacids, such as succinic acid, malic acid and tartaric acid, and the 5-carbon molecule itaconic acid. Other diacids include the two carbon oxalic acid, three carbon malonic acid, five carbon glutaric acid and the 6 carbon adipic acid and there are many derivatives of such diacids as well.

As a group the small diacids have some chemical similarity and their uses in polymer production can provide specialized properties to the resin. Such versatility enables them to fit into the downstream chemical infrastructure markets easily. For example, the 1,4-diacid molecules fulfill many of the uses of the large scale chemical maleic anhydride in that they are converted to a variety of industrial chemicals (tetrahydrofuran, butyrolactone, 1,4-butanediol, 2-pyrrolidone) and the succinate derivatives succindiamide, succinonitrile, diaminobutane and esters of succinate. Tartaric acid has a number of uses in the food, leather, metal and printing industries. Itaconic acid forms the starting material for production of 3-methylpyrrolidone, methyl-BDO, methyl-THF and others.

In particular, succinic acid or succinate—these terms are used interchangeably herein—has drawn considerable interest because it has been used as a precursor of many industrially important chemicals in the food, chemical and pharmaceutical industries. In fact, a report from the U.S. Department of Energy reports that succinic acid is one of 12 top chemical building blocks manufactured from biomass. Thus, the ability to make diacids in bacteria would be of significant commercial importance.

WO-A-2009/024294 discloses a succinic acid producing bacterial strain, being a member of the family of Pasteurellaceae, originally isolated from rumen, and capable of utilizing glycerol as a carbon source and variant and mutant strains derived there from retaining said capability, in particular, a bacterial strain designated DD1 as deposited with DSMZ (Deutsche Sammlung von Mikroorganismen and Zellkulturen GmbH, Inhoffenstr. 7B, D-38124 Braunschweig, Germany) having the deposit number DSM 18541 (ID 06-614) and having the ability to produce succinic acid. The DD1-strain belongs to the species *Basfia succiniciproducens* and the family of Pasteurellaceae as classified by Kuhnert et al., 2010. Mutations of these strains, in which the ldhA-gene and/or the pflD- or the pflA-gene have been disrupted, are disclosed in WO-A-2010/092155, these mutant strains being characterized by a significantly increased production of succinic acid from carbon sources such as glycerol or mixtures of glycerol and carbohydrates such as maltose, under anaerobic conditions compared to the DD1-wildtype disclosed in WO-A-2009/024294.

However, in the process for producing organic acids as disclosed, for example, in WO-A-2009/024294 or WO-A-2010/092155, the space time yield when using glycerol as the sole carbon source is still improvable.

It was therefore an object of the present invention to overcome the disadvantages of the prior art.

In particular, it was an object of the present invention to provide a process for producing an organic acid, such as succinic acid, by fermentation, which allows the production of these organic acids when using glycerol as the predominant carbon source in higher space time yields, compared to the processes known in the prior art.

A contribution to achieving the abovementioned aims is provided by a process for producing an organic acid by fermentation, comprising the process steps I) cultivating microorganisms in a culture medium to which are fed, as assimilable carbon sources, glycerol and a further carbonaceous compound, to allow the microorganisms to produce the organic acid, thereby obtaining a fermentation broth comprising the organic acid;

II) recovering the organic acid or the salt thereof from the fermentation broth obtained in process step I);

wherein the consumption rate of the further carbonaceous compound ($CR_{c.c.}$; in g per liter per hour) is lower than the maximum theoretical consumption rate of the further carbonaceous compound ($CR_{c.c.\ max}$; in g per liter per hour).

The inventors of the present application have found that, when producing organic acids such as succinic acid in a fermentation process in which glycerol is used as the predominant carbon source, the space time yield of organic acids such as succinic acid can be significantly improved if a further carbonaceous compound, such as sucrose or D-glucose, is added in a limited way. By adding the further carbonaceous compound in a limited way the consumption rate of the further carbonaceous compound is lower than the maximum theoretical consumption rate of the further carbonaceous compound.

In process step I) of the process according to the present invention microorganisms are cultivated in a culture medium to which are fed, as assimilable carbon sources, glycerol and a further carbonaceous compound, to allow the microorganisms to produce the organic acid, thereby obtaining a fermentation broth comprising the organic acid.

Suitable microorganims according to the present invention may be yeasts, fungi or bacteria. Suitable bacteria, yeasts or fungi are in particular those bacteria, yeasts or fungi which have been deposited at the Deutsche Sammlung von Mikroorganismen and Zellkulturen GmbH (DSMZ), Brunswick, Germany, as bacterial, yeast or fungal strains. Bacteria which are suitable according to the invention belong to the genera detailed under www.dsmz.de/species/bacteria.htm, yeasts which are suitable according to the invention belong to those genera which are detailed under www.dsmz.de/species/yeasts.htm, and fungi which are suitable according to the invention are those which are detailed under www.dsmz.de/species/fungi.htm.

Preferably, the microorganisms used in process step I) are bacterial cells. The term "bacterial cell" as used herein refers to a prokaryotic organism, i.e. a bacterium. Bacteria can be classified based on their biochemical and microbiological properties as well as their morphology. These classification criteria are well known in the art. According to a preferred embodiment of the process according to the present invention the microorganisms belong to the family of Enterobacteriaceae, Pasteurellaceae, Bacillaceae or Corynebacteriaceae.

"Enterobacteriaceae" represent a large family of bacteria, including many of the more familiar bacteria, such as *Salmonella* and *Escherichia coli*. They belong to the Proteobacteria, and they are given their own order (Enterobacteriales). Members of the Enterobacteriaceae are rod-shaped. Like other Proteobacteria they have Gram-negative stains, and they are facultative anaerobes, fermenting sugars to produce lactic acid and various other end products such as succinic acid. Most also reduce nitrate to nitrite. Unlike most similar bacteria, Enterobacteriaceae generally lack cytochrome C oxidase. Most have many flagella used to move about, but a few genera are non-motile. They are non-spare forming, and mostly they are catalase-positive. Many members of this family are a normal part of the gut flora found in the intestines of humans and other animals, while others are found in water or soil, or are parasites on a variety of different animals and plants. *Escherichia coli*, better known as *E. coli*, is one of the most important model organisms, and its genetics and biochemistry have been closely studied. Most members of Enterobacteriaceae have peritrichous Type I fimbriae involved in the adhesion of the bacterial cells to their hosts. Examples for the Enterobacteriaceae are *E. coli, Proteus, Salmonella* and *Klebsiella*.

"Pasteurellaceae" comprise a large family of Gram-negative Proteobacteria with members ranging from bacteria such as *Haemophilus influenzae* to commensals of the animal and human mucosa. Most members live as commensals on mucosal surfaces of birds and mammals, especially in the upper respiratory tract. Pasteurellaceae are typically rod-shaped, and are a notable group of facultative anaerobes. They can be distinguished from the related Enterobacteriaceae by the presence of oxidase, and from most other similar bacteria by the absence of flagella.

Bacteria in the family Pasteurellaceae have been classified into a number of genera based on metabolic properties and there sequences of the 16S RNA and 23S RNA. Many of the Pasteurellaceae contain pyruvate-formate-lyase genes and are capable of anaerobically fermenting carbon sources to organic acids.

"Bacillaceae" is a family of Gram-positive, heterotrophic, rod-shaped bacteria that may produce endospores. Motile members of this family are characterized by peritrichous flagellae. Some Bacillaceae are aerobic, while others are facultative or strict anaerobes. Most are nonpathogenic, but *Bacillus* species are known to cause disease in humans. This family also comprises the genus Bacilli which includes two orders, Bacillales and Lactobacillales. The *bacillus* species represents a large cylindrical bacteria that can grow under aerobic conditions at 37° C. They are typically nonpathogenic. The genus Bacillales contains the species Alicyclobacillaceae, Bacillaceae, Caryophanaceae, Listeriaceae, Paenibacillaceae, Planococcaceae, Sporolactobacillaceae, Staphylococcaceae, Thermoactinomycetaceae, Turicibacteraceae. Many of the Bacilli contain pyruvate-formate-lyase genes and are capable of anaerobically fermenting carbon sources to organic acids.

"Corynebacteriaceae" is a large family of mostly Gram-positive and aerobic and nonmotile rod-shaped bacteria of the order Eubacteriales. This family also comprises the genus Corynebacterium, which is a genus of Gram-positive, rod-shaped bacteria. Corynebacteria are widely distributed in nature and are mostly innocuous. Some are useful in industrial settings such as *C. glutamicum*.

It is particularly preferred that the microorganism used in process step I) is a modified microorganism. The term "modified microorganism" includes a microorganism which has been genetically altered, modified or engineered (e.g., genetically engineered) such that it exhibits an altered, modified or different genotype and/or phenotype (e. g., when the genetic modification affects coding nucleic acid sequences of the microorganism) as compared to the naturally-occurring wildtype microorganism from which it was derived. According to a particular preferred embodiment of the process according to the present invention the modified microorganism used in process step I) is a recombinant microorganism, which means that the microorganism has been obtained using recombinant DNA. The expression "recombinant DNA" as used herein refers to DNA sequences that result from the use of laboratory methods (molecular cloning) to bring together genetic material from multiple sources, creating sequences that would not otherwise be found in biological organisms. An example of such a recombinant DNA is a plasmid into which a heterologous DNA-sequence has been inserted.

Preferably, the microorganism, in particular the modified microorganism, used in process step I) has been derived from a wildtype that belongs to the family Pasteurellaceae. In this context it is furthermore preferred that the wildtype from which modified microorganism has been derived belongs to the genus *Basfia* and it is particularly preferred that the wildtype from which the modified microorganism has been derived belongs to the species *Basfia succiniciproducens*.

Most preferably, the wildtype from which the modified microorganism used in process step I) has been derived is *Basfia succiniciproducens*-strain DD1 deposited under the Budapest Treaty with DSMZ (Deutsche Sammlung von Mikroorganismen and Zellkulturen, GmbH), Germany, having the deposit number DSM 18541. This strain has been originally isolated from the rumen of a cow of German origin. *Pasteurella* bacteria can be isolated from the gastrointestinal tract of animals and, preferably, mammals. The bacterial strain DD1, in particular, can be isolated from bovine rumen and is capable of utilizing glycerol (including crude glycerol) as a carbon source. Further strains of the genus *Basfia* that can be used for preparing the modified microorganism according to the present invention are the *Basfia*-strain that has been deposited under the deposit number DSM 22022 with DSZM or the *Basfia*-strains that have been deposited with the Culture Collection of the University of Goteborg (CCUG), Sweden, having the deposit numbers CCUG 57335, CCUG 57762, CCUG 57763, CCUG 57764, CCUG 57765 or CCUG 57766. Said strains have been originally isolated from the rumen of cows of German or Swiss origin.

In this context it is particularly preferred that the wildtype from which the modified microorganism used in process step I) of the process according to the present invention has been derived has a 16S rDNA of SEQ ID NO: 1 or a sequence, which shows a sequence homology of at least 96%, at least 97%, at least 98%, at least 99% or at least 99.9% with SEQ ID NO: 1. It is also preferred that the wildtype from which the modified microorganism according to the present invention has been derived has a 23S rDNA of SEQ ID NO: 2 or a sequence, which shows a sequence homology of at least 96%, at least 97%, at least 98%, at least 99% or at least 99.9% with SEQ ID NO: 2.

The identity in percentage values referred to in connection with the various polypeptides or polynucleotides to be used for the modified microorganism according to the present invention is, preferably, calculated as identity of the residues over the complete length of the aligned sequences, such as, for example, the identity calculated (for rather similar sequences) with the aid of the program needle from the bioinformatics software package EMBOSS (Version 5.0.0, emboss.source-forge.net/what/) with the default parameters which are, i.e. gap open (penalty to open a gap): 10.0, gap extend (penalty to extend a gap): 0.5, and data file (scoring matrix file included in package): EDNAFUL.

It should be noted that the modified microorganism used in process step I) of the process according to the present invention can not only be derived from the above mentioned wildtypemicroorganisms, especially from *Basfia succiniciproducens*-strain DD1, but also from variants of these strains. In this context the expression "a variant of a strain" comprises every strain having the same or essentially the same characteristics as the wildtype-strain. In this context it is particularly preferred that the 16 S rDNA of the variant has an identity of at least 90%, preferably at least 95%, more preferably at least 99%, more preferably at least 99.5%, more preferably at least 99.6%, more preferably at least 99.7%, more preferably at least 99.8% and most preferably at least 99.9% with the wildtype from which the variant has been derived. It is also particularly preferred that the 23 S rDNA of the variant has an identity of at least 90%, preferably at least 95%, more preferably at least 99%, more preferably at least 99.5%, more preferably at least 99.6%, more preferably at least 99.7%, more preferably at least 99.8% and most preferably at least 99.9% with the wildtype from which the variant has been derived. A variant of a strain in the sense of this definition can, for example, be obtained by treating the wildtype-strain with a mutagenizing chemical agent, X-rays, or UV light, or by recombinant methods in which genes are deleted, overexpressed or in which heterologous genes are introduced into the cells.

According to a preferred embodiment of the process according to the present invention the modified microorganism used in process step I) is a microorganism that has, compared to its wildtype
i) a reduced pyruvate formate lyase activity,
ii) a reduced lactate dehydrogenase activity, or
iii) a reduced pyruvate formate lyase activity and a reduced lactate dehydrogenase activity.

In context with the expression "a modified microorganism having, compared to its wildtype, a reduced activity of the enzyme that is encoded by the x-gene", wherein the x-gene is the ldhA-gene, the pflA-gene and/or the pflD-gene, the term "wildtype" refers to a microorganism in which the activity of the enzyme that is encoded by the x-gene has not been decreased, i. e. to a microorganism whose genome is present in a state as before the introduction of a genetic modification of the x-gene (in particular of the ldhA-gene, the pflA-gene and/or the pflD-gene). Preferably, the expression "wildtype" refers to a microorganism whose genome, in particular whose x-gene, is present in a state as generated naturally as the result of evolution. The term may be used both for the entire microorganism but preferably for individual genes, e.g. the ldhA-gene, the pflA-gene and/or the pflD-gene.

The term "reduced activity of an enzyme" as used herein preferably corresponds to a reduction of the activity of the corresponding enzyme by at least 50%, preferably at least 75% and more preferably at least 95%, compared to the activity of the corresponding enzyme in the wildtype.

The term "reduced activity of an enzyme" includes, for example, the expression of the enzyme by said genetically modified (e.g., genetically engineered) microorganism at a lower level than that expressed by the wildtype of said microorganism. Genetic manipulations for reducing the expression of an enzyme can include, but are not limited to, deleting the gene or parts thereof encoding for the enzyme, altering or modifying regulatory sequences or sites associated with expression of the gene encoding the enzyme (e.g., by removing strong promoters or repressible promoters), modifying proteins (e.g., regulatory proteins, suppressors, enhancers, transcriptional activators and the like) involved in transcription of the gene encoding the enzyme and/or the translation of the gene product, or any other conventional means of decreasing expression of a particular gene routine in the art (including, but not limited to, the use of antisense nucleic acid molecules or iRNA or other methods to knock-out or block expression of the target protein). Further on, one may introduce destabilizing elements into the mRNA or introduce genetic modifications leading to deterioration of ribosomal binding sites (RBS) of the RNA. It is also possible to change the codon usage of the gene in a way, that the translation efficiency and speed is decreased.

A reduced activity of an enzyme can also be obtained by introducing one or more gene mutations which lead to a reduced activity of the enzyme. Furthermore, a reduction of the activity of an enzyme may also include an inactivation (or the reduced expression) of activating enzymes which are necessary in order to activate the enzyme the activity of which is to be reduced. By the latter approach the enzyme the activity of which is to be reduced is preferably kept in an inactivated state.

Modified microorganisms being deficient in lactate dehydrogenase and/or being deficient in pyruvate formate lyase activity are disclosed in WO-A-2010/092155, US 2010/0159543 and WO-A-2005/052135, the disclosure of which with respect to the different approaches of reducing the activity of lactate dehydrogenase and/or pyruvate formate lyase in a microorganism, preferably in a bacterial cell of the genus *Pasteurella*, particular preferred in *Basfia succiniciproducens* strain DD1, is incorporated herein by reference. Methods for determining the pyruvate formate lyase activity are, for example, disclosed by Asanuma N. and Hino T. in "*Effects of pH and Energy Supply on Activity and Amount of Pyruvate-Formate-Lyase in Streptococcus bovis*", Appl. Environ. Microbiol. (2000), Vol. 66, pages 3773-3777" and methods for determining the lactate dehydrogenase activity are, for example, disclosed by Bergmeyer, H. U., Bergmeyer J. and Grassi, M. (1983-1986) in "*Methods of Enzymatic Analysis*", $3^{rd}$ Edition, Volume III, pages 126-133, Verlag Chemie, Weinheim.

In this context it is preferred that the reduction of the activity of lactate dehydrogenase is achieved by an inactivation of the ldhA-gene (which encodes the lactate dehydrogenase LdhA; EC 1.1.1.27 or EC 1.1.1.28) and the reduction of the pyruvate formate lyase is achieved by an inactivation of the pflA-gene (which encodes for an activator of pyruvate formate lyase PflA; EC 1.97.1.4) or the pflD-gene (which encodes the pyruvate formate lyase PflD; EC 2.3.1.54), wherein the inactivation of these genes (i. e. ldhA, pflA and pflD) is preferably achieved by a deletion of theses genes or parts thereof, by a deletion of a regulatory element of these genes or at least a part thereof or by an introduction of at least one mutation into these genes, wherein these modifications are preferably performed by means of the "Campbell recombination" as described above.

The ldhA-gene the activity of which is reduced in the modified microorganism preferably comprises a nucleic acid selected from the group consisting of:
α1) nucleic acids having the nucleotide sequence of SEQ ID NO: 3;
α2) nucleic acids encoding the amino acid sequence of SEQ ID NO: 4;
α3) nucleic acids which are at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the nucleic acid of α1) or α2), the identity being the identity over the total length of the nucleic acids of α1) or α2); and
α4) nucleic acids encoding an amino acid sequence which is at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the amino acid sequence encoded by the nucleic acid of α1) or α2), the identity being the identity over the total length of amino acid sequence encoded by the nucleic acids of α1) or α2).

The pflA-gene the activity of which is reduced in the modified microorganism preferably comprises a nucleic acid selected from the group consisting of:
β1) nucleic acids having the nucleotide sequence of SEQ ID NO: 5;
β2) nucleic acids encoding the amino acid sequence of SEQ ID NO: 6;
β3) nucleic acids which are at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the nucleic acid of β1) or β2), the identity being the identity over the total length of the nucleic acids of β1) or β2); and
β4) nucleic acids encoding an amino acid sequence which is at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the amino acid sequence encoded by the nucleic acid of β1) or β2), the identity being the identity over the total length of amino acid sequence encoded by the nucleic acids of β1) or β2).

The pflD-gene the activity of which is reduced in the modified microorganism preferably comprises a nucleic acid selected from the group consisting of:
γ1) nucleic acids having the nucleotide sequence of SEQ ID NO: 7;
γ2) nucleic acids encoding the amino acid sequence of SEQ ID NO: 8;
γ3) nucleic acids which are at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the nucleic acid of γ1) or γ2), the identity being the identity over the total length of the nucleic acids of γ1) or γ2); and
γ4) nucleic acids encoding an amino acid sequence which is at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the amino acid sequence encoded by the nucleic acid of γ1) or γ2), the identity being the identity over the total length of amino acid sequence encoded by the nucleic acids of γ1) or γ2).

In this context it is preferred that the modified microorganism used in process step I) of the process according to the present invention comprises:
A) a deletion of the ldhA-gene or at least a part thereof, a deletion of a regulatory element of the ldhA-gene or at least a part thereof or an introduction of at least one mutation into the ldhA-gene;
B) a deletion of the pflD-gene or at least a part thereof, a deletion of a regulatory element of the pflD-gene or at least a part thereof or an introduction of at least one mutation into the pflD-gene;
C) a deletion of the pflA-gene or at least a part thereof, a deletion of a regulatory element of the pflA-gene or at least a part thereof or an introduction of at least one mutation into the pflA-gene;
D) a deletion of the ldhA-gene or at least a part thereof, a deletion of a regulatory element of the ldhA-gene or at least a part thereof or an introduction of at least one mutation into the ldhA-gene
and
a deletion of the pflD-gene or at least a part thereof, a deletion of a regulatory element of the pflD-gene or at least a part thereof or an introduction of at least one mutation into the pflD-gene;
or
E) a deletion of the ldhA-gene or at least a part thereof, a deletion of a regulatory element of the ldhA-gene or at least a part thereof or an introduction of at least one mutation into the ldhA-gene
and
a deletion of the pflA-gene or at least a part thereof, a deletion of a regulatory element of the pflA-gene or at least a part thereof or an introduction of at least one mutation into the pflA-gene.

Preferably, the organic acid that is produced by the microorganisms in process step I) of the process according to the present invention comprises carboxylic acids such as formic acid, lactic acid, propionic acid, 2-hydroxypropionic acid, 3-hydroxypropionic acid, 3-hydroxybutyric acid, acrylic acid, pyruvic acid or salts of these carboxylic acids, dicarboxylic acids such as malonic acid, succinic acid, malic acid, tartaric acid, glutaric acid, itaconic acid, adipic acid or salts thereof or tricarboxylic acids such as citric acid or salts thereof. According to a particular preferred embodiment of the process according to the present invention the organic acid is succinic acid. The term "succinic acid", as used in the context of the present invention, has to be understood in its broadest sense and also encompasses salts thereof (i. e. succinate), as for example alkali metal salts, like $Na^+$ and $K^+$-salts, or earth alkali salts, like $Mg^{2+}$ and $Ca^{2+}$-salts, or ammonium salts or anhydrides of succinic acid.

The microorganisms are preferably incubated in the culture medium at a temperature in the range of about 10 to 60° C. or 20 to 50° C. or 30 to 45° C. at a pH of 2.5 to 9.0 or 3.5 to 8.0 or 4.5 to 7.0.

Preferably, the organic acid, especially succinic acid, is produced under anaerobic conditions. Anaerobic conditions may be established by means of conventional techniques, as for example by degassing the constituents of the reaction medium and maintaining anaerobic conditions by introducing carbon dioxide or nitrogen or mixtures thereof and optionally hydrogen at a flow rate of, for example, 0.1 to 1 or 0.2 to 0.5 vvm. Aerobic conditions may be established by means of conventional techniques, as for example by introducing air or oxygen at a flow rate of, for example, 0.1 to 1 or 0.2 to 0.5 vvm. If appropriate, a slight over pressure of 0.1 to 1.5 bar may be applied in the process.

The process according to the present invention is characterized in that the consumption rate of the further carbonaceous compound ($CR_{c.c.}$; in g per liter per hour) is lower than the maximum theoretical consumption rate of the further carbonaceous compound ($CR_{c.c.\ max}$; in g per liter per hour). The consumption rate of the further carbonaceous compound is lower than the maximum theoretical consumption rate of the further carbonaceous compound if the amount of the further carbonaceous compound (i. e. the amount that is fed into the culture medium and the amount that may already be contained in the culture medium and that is not yet consumed) is lower than the maximum amount of the further carbonaceous compound that the cells could theoretical consume. The amount of the further carbonaceous compound is thus limited.

In the process of the present invention the consumption rate of the further carbonaceous compound can, for example, be controlled by the feeding rate of the further carbonaceous compound (provided that the amount of the further carbonaceous compound that may already be present in the culture medium and that is not yet consumed is sufficiently low). In this context it is preferred that the feeding rate of the further carbonaceous compound is not more than 50%, more preferably not more than 25%, more preferably not more than 10% and most preferably not more than 5% of the maximum consumption rate of the further carbonaceous compound. Controlling the consumption rate of the further carbonaceous compound by the feeding rate of the further carbonaceous compound is, in particular, possible if the culture medium is essentially free of any (not yet consumed) further carbonaceous compound or if the amount of the further carbonaceous compound is lower than 0.5 g/l, preferably lower than 0.05 g/l, most preferably below the detection limit. In a preferred embodiment the further carbonaceous compound which is fed into the culture medium is immediately and completely consumed by the cells. Under such conditions the further carbonaceous compound is fed in a limited way.

It is furthermore preferred that in the process of the present invention the condition in which the consumption rate of the further carbonaceous compound is lower than the maximum theoretical consumption rate of the further carbonaceous compound is maintained for a certain period of time, preferably for a cultivation period of at least 30 minutes, preferably of at least 1 hour, more preferably of at least 6 hours, even more preferably of at least 12 hours and most preferably of at least 20 hours. In general, the conditions of the limited feed of the further carbonaceous compound are realized for at least 25%, preferably for at least 50% and most preferably for at least 70% of the total cultivation time.

Preferably, the consumption rate of the further carbonaceous compound ($CR_{c.c.}$; in g per liter per hour) is not more than 50%, more preferably not more than 25%, more preferably not more than 10% and most preferably not more than 5% of the maximum theoretical consumption rate of the further carbonaceous compound ($CR_{c.c.\ max}$; in g per liter per hour). If, for example, the maximum consumption rate for the further carbonaceous compound would be 1 g/L/h, the consumption rate would be not more than 0.5 g/L/h (50%), preferably not more than 0.25 g/L/h (25%), more preferably not more than 0.1 g/L/h (10%) and most preferably not more than 0.05 g/L/h (5%).

In this context it is furthermore preferred that at the same time (i. e. within the same period of time in which the consumption rate of the further carbonaceous compound is lower than the maximum theoretical consumption rate of the further carbonaceous compound) the amount of glycerol is not limited, but is preferably present in an excess (which means that glycerol is preferably added in such an amount and/or is present in the culture medium in such an amount that the cells cannot consume glycerol faster than it is added to the cell culture and/or than it is present in the culture medium). In this context it is preferred that the consumption rate of glycerol ($CR_g$; in g per liter per hour) is more than 25%, preferably more than 50%, more preferably more than 75%, even more preferably more than 90% and most preferably more than 95% of the maximum theoretical consumption rate of glycerol ($CR_{g.\ max}$; in g per liter per hour). If, for example, the maximum consumption rate for glycerol would be 1 g/L/h, the consumption rate would be more than 0.5 g/L/h (50%), preferably more than 0.75 g/L/h (75%), more preferably more than 0.9 g/L/h (90%) and most preferably more than 0.95 g/L/h (95%).

According to a preferred embodiment of the process according to the present invention, for a cultivation period of at least 30 minutes, preferably of at least 1 hour, more preferably of at least 6 hours, even more preferably of at least 12 hours and most preferably of at least 20 hours
- the consumption rate of the further carbonaceous compound ($CR_{c.c.}$; in g per liter per hour) is not more than 50%, more preferably not more than 25%, more preferably not more than 10% and most preferably not more than 5% of the maximum theoretical consumption rate of the further carbonaceous compound ($CR_{c.c.\ max}$; in g per liter per hour)
and, at the same time,
- the consumption rate of glycerol ($CR_g$; in g per liter per hour) is more than 25%, preferably more than 50%, more preferably more than 75%, even more preferably more than 90% and most preferably more than 95% of the maximum theoretical consumption rate of glycerol ($CR_g$ max; in g per liter per hour).

For the determination of the maximum theoretical consumption rate of the further carbonaceous compound $CR_{c.c.\ max}$ and the maximum theoretical consumption rate of glycerol $CR_{g.\ max}$ the cells are incubated in the presence of an excess of the further carbonaceous compound and glycerol, respectively. An excess of the further carbonaceous compound and glycerol is present if, at least for a certain period of time, a certain minimum amount of the not yet consumed substrate (i. e. further carbonaceous compound or glycerol) can be detected in the culture medium, preferably an amount of at least 1 g/L, more preferably at least 2.5 g/L).

For the determination maximum theoretical consumption rate of the further carbonaceous compound $CR_{c.c.\ max}$ the cells are cultured for one hour under exactly the same cultivation conditions as for the determination of $CR_{c.c.}$ (i. e. the determintation of the actual consumption rate of the carbonaceous compound when the carbonaceous compound in present in a limited amount), but with an initial amount of carbonaceous compound of at least 5 g per liter and with a further continuous addition of the carbonaceous compound in such an amount that the concentration of the not yet consumed carbonaceous compound in the culture medium will always be above 1 g/L. Furthermore, the expression "under exactly the same cultivation conditions" in context with the determination of $CR_{c.c.\ max}$ as used herein indicates that the determination of $CR_{c.c.\ max}$ takes place in the presence of the same amount of glycerol as is present when determining $CR_{c.c.}$, but with an excess amount of the carbonaceous compound. For the determination maximum theoretical consumption rate of glycerol $C_{g.\ max}$ the cells are also cultured for one hour under exactly the same cultivation conditions as for the determination of $CR_{g.}$ (i. e. the actual consumption rate of glycerol), but with an initial amount of glycerol as the sole carbon source of at least 5 g per liter and with a further continuous addition of glycerol in such an amount that the concentration of the not yet consumed glycerol in the culture medium will always be above 1 g/L. The expression "under exactly the same cultivation conditions" in context with the determination of $CR_{g.\ max}$ as used herein indicates that the determination of $CR_{g.\ max}$ takes place in the presence of the same amount of the further carbonaceous as is present when determining $CR_g$, but with an excess amount of glycerol.

The carbon sources (i. e. glycerol and the further carbonaceous compound) can be added to the cultivation time at once at the beginning of the cultivation or they can be added periodically or continuously. It is, of course, also possible to add, for example, one carbon source (for example glycerol) at once at the beginning of the cultivation and the other carbon source periodically of continuously (for example the further carbonaceous compound). Irrespective the way in which the carbon sources are added to the fermentation medium, it is preferred that the above described conditions for the limited feed of the further carbonaceous compound and the preferably non-limited feed of glycerol are maintained for a cultivation period of at least 30 minutes, preferably of at least 1 hour, more preferably of at least 6 hours, even more preferably of at least 12 hours and most preferably of at least 24 hours.

Preferably, glycerol and the further carbonaceous compound are fed into the culture medium in a total weight ratio glycerol:further carbonaceous compound of at least 5:1, more preferably at least 7.5:1 and most preferably at least 10:1. The term "total weight ratio" as used herein defines the ratio of the total amount of the further carbonaceous compound and the total amount of glycerol that are added in process step I).

According to one embodiment of the process according to the present invention the further carbonaceous compound is fed into the fermentation medium in such an amount that the concentration of the further carbonaceous compound in the fermentation medium increases by less than 0.1 g/l/h, preferably less than 0.01 g/l/h. Most preferably, the concentration of the further carbonaceous compound in the fermentation medium does not increase at all (because the added carbonaceous compound is consumed immediately). In this context it is also preferred that concentration of the further carbonaceous compound in the culture medium is between 0 and 1 g/L, preferably less than 0.6 g/L, more preferred less than 0.3 g/L, even more preferred less than 0.1 g/L, wherein most preferably the concentration of the further carbonaceous compound in the culture medium is below the detection limit as measured with a suitable standard assay (preferably by HPLC, as described in the experimental part herein), e.g. determined as a residual concentration in the culture medium, due to the rapid consumption of the further carbonaceous compound by the microorganisms.

The further carbonaceous compound preferably is a carbohydrate except glycerol, more preferably a carbohydrate selected from the groups consisting of sucrose, D-fructose, D-glucose, D-xylose, L-arabinose, D-galactose, D-mannose and mixtures thereof or compositions containing at least one of said compounds. Most preferably, the further carbonaceous compound is selected from the group consisting of sucrose and D-glucose most preferably sucrose, D-glucose and mixtures thereof.

The glycerol used as the assimilable carbon source may by used in the form of pure glycerol or in the form of a crude glycerol that, for example, has been obtained from bio diesel or bio ethanol production without prior purification.

The initial concentration of the assimilable carbon source (i. e. the sum of glycerol and the at least one further carbonaceous compound) is preferably adjusted to a value in a range of 0 to 100 g/l, preferably 0 to 75 g/l, more preferably 0 to 50 g/l, even more preferably 0 to 25 g/l and may be maintained in said range during cultivation (the initial concentration of the assimilable carbon source can be 0 g/l if the further carbonaceous compound is consumed faster than it is fed into the cell culture). The pH of the reaction medium may be controlled by addition of suitable bases as for example, gaseous ammonia, $NH_4HCO_3$, $(NH_4)_2CO_3$, NaOH, $Na_2CO_3$, $NaHCO_3$, KOH, $K_2CO_3$, $KHCO_3$, $Mg(OH)_2$, $MgCO_3$, $Mg(HCO_3)_2$, $Ca(OH)_2$, $CaCO_3$, $Ca(HCO_3)_2$, CaO, $CH_6N_2O_2$, $C_2H_7N$ and/or mixtures thereof. These alkaline neutralization agents are especially required if the organic acids that are formed in the course of the fermentation process are carboxylic acids or dicarboxylic acids. In the case of succinic acid as the organic acid, $Mg(OH)_2$ and $MgCO_3$ are particular preferred bases.

The fermentation step I) according to the present invention can, for example, be performed in stirred fermenters, bubble columns and loop reactors. A comprehensive overview of the possible method types including stirrer types and geometric designs can be found in Chmiel: "*Bioprozesstechnik: Einführung in die Bioverfahrenstechnik*", Volume 1. In the process according to the present invention, typical variants available are the following variants known to those skilled in the art or explained, for example, in Chmiel, Hammes and Bailey: "*Biochemical Engineering*": such as batch, fed-batch, repeated fed-batch or else continuous fermentation with and without recycling of the biomass. Depending on the production strain, sparging with air, oxygen, carbon dioxide, hydrogen, nitrogen or appropriate gas mixtures may be effected in order to achieve good yield (YP/S).

Particularly preferred conditions for producing the organic acid, especially succinic acid, in process strep I) are:

Assimilable carbon source: glycerol+D-glucose, glycerol+sucrose

Temperature: 30 to 45° C.

pH: 5.5 to 8.0

Supplied gas: $CO_2$

It is furthermore preferred in process step I) that the assimilable carbon sources (i. e. glycerol and further carbonaceous compound) are converted to the organic acid, preferably to succinic acid, with a carbon yield YP/S of at least 0.75 g/g, preferably of at least 0.85 g/g and most preferably of at least 1.0 g/g, (organic acid/carbon, preferably succinic acid/carbon).

It is furthermore preferred in process step I) that the assimilable carbon sources (i. e. glycerol and further carbonaceous compound) are converted to the organic acid, preferably to succinic acid, with a specific productivity yield of at least 0.6 g g $DCW^{-1}h^{-1}$ organic acid, preferably succinic acid, or of at least of at least 0.65 g g $DCW^{-1}h^{-1}$, of at least 0.7 g g $DCW^{-1}h^{-1}$, of at least 0.75 g g $DCW^{-1}h^{-1}$ or of at least 0.77 g g $DCW^{-1}h^{-1}$ organic acid, preferably succinic acid.

It is furthermore preferred in process step I) that the assimilable carbon sources (i. e. glycerol and further carbonaceous compound) are converted to the organic acid, preferably to succinic acid, with a space time yield for the organic acid, preferably for succinic acid, of at least 2.2 g/(L×h) or of at least 2.5 g/(L×h), at least 2.75 g/(L×h), at least 3 g/(L×h), at least 3.25 g/(L×h), at least 3.5 g/(L×h), at least 3.7 g/(L×h), at least 4.0 g/(L×h) at least 4.5 g/(L×h) or at least 5.0 g/(L×h) of the organic acid, preferably succinic acid. According to another preferred embodiment of the process according to the present invention in process step I) the microorganism is converting at least 20 g/L, more preferably at least 25 g/l and even more preferably at least 30 g/l of the assimilable carbon source (i. e. the sum of glycerol and the at least one further carbonaceous compound) to at least 20 g/l, more preferably to at least 25 g/l and even more preferably at least 30 g/l of the organic acid, preferably succinic acid.

The different yield parameters as described herein ("carbon yield" or "YP/S"; "specific productivity yield"; or "space-time-yield (STY)") are well known in the art and are determined as described for example by Song and Lee, 2006. "Carbon yield" and "YP/S" (each expressed in mass of organic acid produced/mass of assimilable carbon source consumed) are herein used as synonyms. The specific productivity yield describes the amount of a product, like succinic acid, that is produced per h and L fermentation broth per g of dry biomass. The amount of dry cell weight stated as "DCW" describes the quantity of biologically active microorganism in a biochemical reaction. The value is given as g product per g DCW per h (i.e. g g $DCW^{-1}h^{-1}$). The space-time-yield (STY) is defined as the ratio of the total amount of organic acid formed in the fermentation process to the volume of the culture, regarded over the entire time of cultivation. The space-time yield is also known as the "volumetric productivity".

In process step II) the organic acid, preferably succinic acid, or the salt thereof is recovered from the fermentation broth obtained in process step I).

Usually, the recovery process comprises the step of separating the microorganisms from the fermentation broth as the so called "biomass". Processes for removing the biomass are known to those skilled in the art, and comprise filtration, sedimentation, flotation or combinations thereof. Consequently, the biomass can be removed, for example, with centrifuges, separators, decanters, filters or in a flotation apparatus. For maximum recovery of the product of value, washing of the biomass is often advisable, for example in the form of a diafiltration. The selection of the method is dependent upon the biomass content in the fermentation broth and the properties of the biomass, and also the interaction of the biomass with the organic acid (e. the product of value). In one embodiment, the fermentation broth can be sterilized or pasteurized. In a further embodiment, the fermentation broth is concentrated. Depending on the requirement, this concentration can be done batch wise or continuously. The pressure and temperature range should be selected such that firstly no product damage occurs, and secondly minimal use of apparatus and energy is necessary. The skillful selection of pressure and temperature levels for a multistage evaporation in particular enables saving of energy.

The recovery process may further comprise additional purification steps in which the organic acid, preferably succinic acid, is further purified. If, however, the organic acid is converted into a secondary organic product by chemical reactions as described below, a further purification of the organic acid is, depending on the kind of reaction and the reaction conditions, not necessarily required. For the purification of the organic acid obtained in process step II), preferably for the purification of succinic acid, methods known to the person skilled in the art can be used, as for example crystallization, filtration, electrodialysis and chromatography. In the case of succinic acid as the organic acid, for example, succinic acid may be isolated by precipitating it as a calcium succinate product by using calcium hydroxide, -oxide, -carbonate or hydrogen carbonate for neutralization and filtration of the precipitate. The succinic acid is recovered from the precipitated calcium succinate by acidification with sulfuric acid followed by filtration to remove the calcium sulfate (gypsum) which precipitates. The resulting solution may be further purified by means of ion exchange chromatography in order to remove undesired residual ions. Alternatively, if magnesium hydroxide, magnesium carbonate or mixtures thereof have been used to neutralize the fermentation broth, the fermentation broth obtained in process step I) may be acidified to transform the magnesium succinate contained in the medium into the acid form (i. e. succinic acid), which subsequently can be crystallized by cooling down the acidified medium. Examples of further suitable purification processes are disclosed in EP-A-1 005 562, WO-A-2008/010373, WO-A-2011/082378, WO-A-2011/043443, WO-A-2005/030973, WO-A-2011/123268 and WO-A-2011/064151 and EP-A-2 360 137.

According to a preferred embodiment of the process according to the present invention the process further comprises the process step:

I) conversion of the organic acid contained in the fermentation broth obtained in process step I) or conversion of the recovered organic acid obtained in process step II) into a secondary organic product being different from the organic acid by at least one chemical reaction.

In case of succinic acid as the organic acid preferred secondary organic products are selected from the group consisting of succinic acid esters and polymers thereof, tetrahydrofuran (THF), 1,4-butanediol (BDO), gamma-butyrolactone (GBL) and pyrrolidones.

According to a preferred embodiment for the production of THF, BDO and/or GBL this process comprises:
b1) either the direct catalytic hydrogenation of the succinic acid obtained in process steps I) or II) to THF and/or BDO and/or GBL or
b2) the chemical esterification of succinic acid and/or succinic acid salts obtained in process steps I) or II) into its corresponding di-lower alkyl ester and subsequent catalytic hydrogenation of said ester to THF and/or BDO and/or GBL.

According to a preferred embodiment for the production of pyrrolidones this process comprises:
b) the chemical conversion of succinic acid ammonium salts obtained in process steps I) or II) to pyrrolidones in a manner known per se.

For details of preparing these compounds reference is made to US-A-2010/0159543 and WO-A-2010/092155.

The invention is now explained in more detail with the aid of figures and non-limiting examples.

EXAMPLES

Example 1: General Method for the Transformation of Basfia succiniciproducens

TABLE 1

Nomenclature of the DD1-wildtype and mutants referred to in the examples
Strain

Wildtype DD1 (deposit DSM18541)
DD1 ΔldhA ΔpflA
DD1 ΔldhA ΔpflD

*Basfia succiniciproducens* DD1 (wildtype) was transformed with DNA by electroporation using the following protocol:

For preparing a pre-culture DD1 was inoculated from frozen stock into 40 ml BHI (brain heart infusion; Becton, Dickinson and Company) in 100 ml shake flask. Incubation was performed over night at 37° C.; 200 rpm. For preparing the main-culture 100 ml BHI were placed in a 250 ml shake flask and inoculated to a final OD (600 nm) of 0.2 with the pre-culture. Incubation was performed at 37° C., 200 rpm. The cells were harvested at an OD of approximately 0.5, 0.6 and 0.7, pellet was washed once with 10% cold glycerol at 4° C. and re-suspended in 2 ml 10% glycerol (4° C.).

100 µl of competent cells were the mixed with 2-8 µg Plasmid-DNA and kept on ice for 2 min in an electroporation cuvette with a width of 0.2 cm. Electroporation under the following conditions: 400Ω; 25 µF; 2.5 kV (Gene Pulser, Bio-Rad). 1 ml of chilled BHI was added immediately after electroporation and incubation was performed for approximately 2 h at 37° C.

Cells were plated on BHI with 5 mg/L chloramphenicol and incubated for 2-5 d at 37° C. until the colonies of the transformants were visible. Clones were isolated and restreaked onto BHI with 5 mg/l chloramphenicol until purity of clones was obtained.

Example 2: Generation of Deletion/Mutation Constructs

Figure 1:
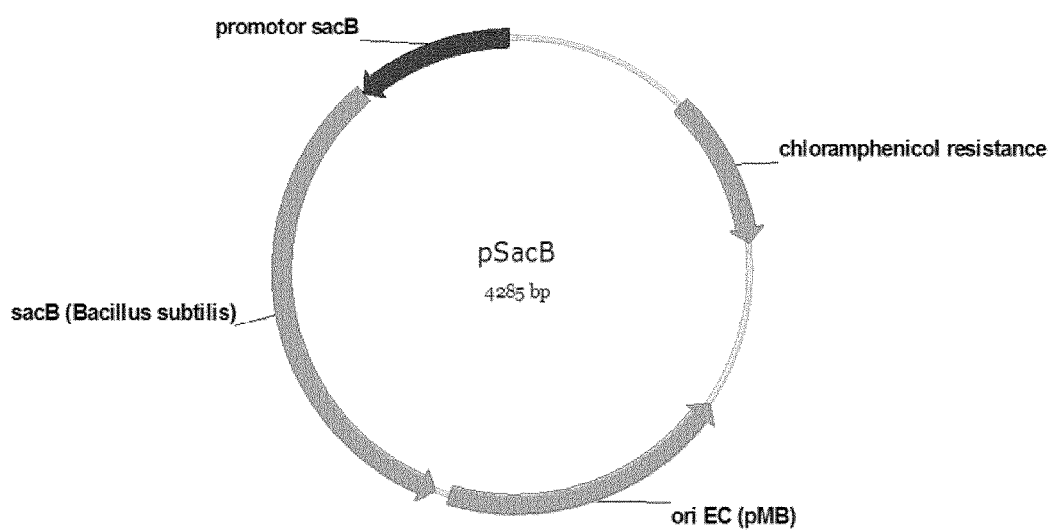
FIG. 1 shows a schematic map of plasmid pSacB (SEQ ID NO: 9).
Figure 2:
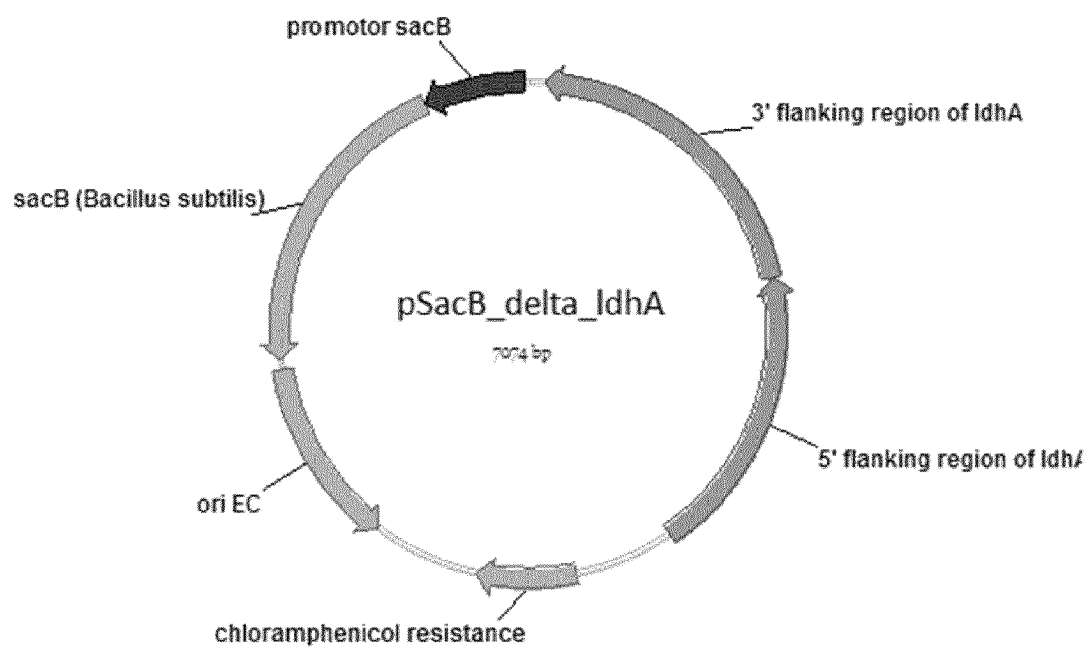
FIG. 2 shows a schematic map of plasmid pSacB ΔldhA (SEQ ID NO: 10).
Figure 3:
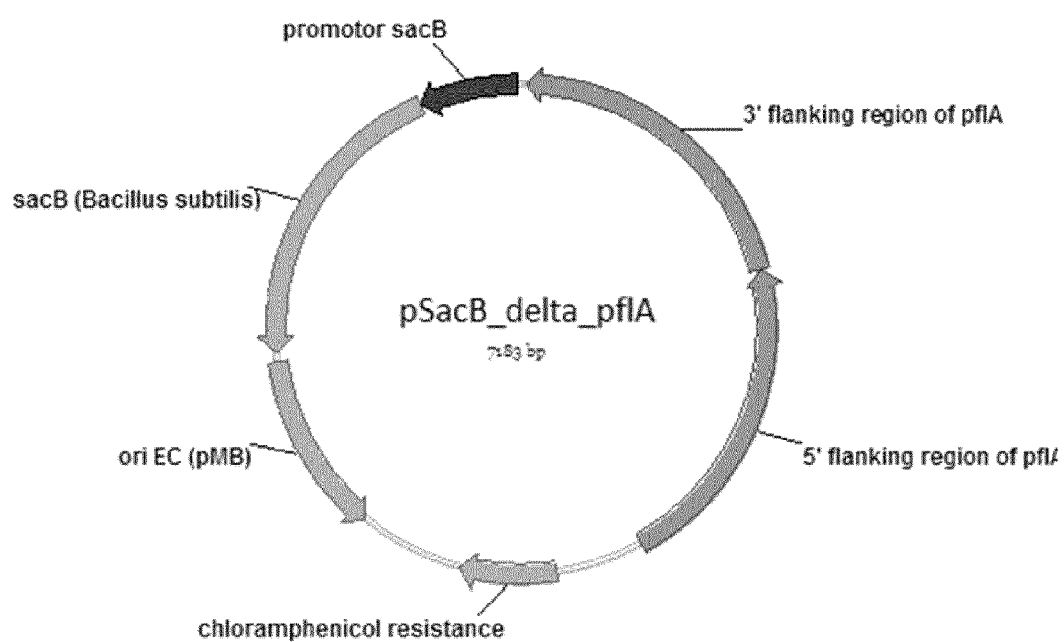
FIG. 3 shows a schematic map of plasmid pSacB ΔpflA (SEQ ID NO: 11).
Figure 4:
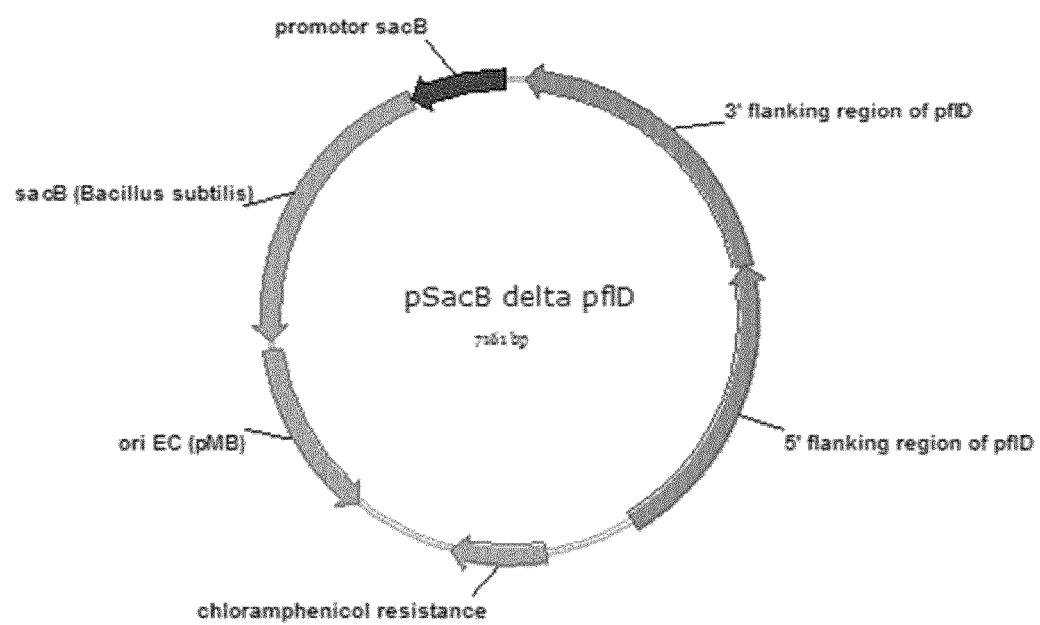
FIG. 4 shows a schematic map of plasmid pSacB ΔpflD (SEQ ID NO: 12).

Generation of Deletions Constructs:

Deletion plasmids were constructed based on the vector pSacB (SEQ ID NO: 9). FIG. 1 shows a schematic map of plasmid pSacB. 5'- and 3'-flanking regions (approx. 1500 bp each) of the chromosomal fragment, which should be deleted were amplified by PCR from chromosomal DNA of *Basfia succiniciproducens* and introduced into said vector using standard techniques. Normally, at least 80% of the ORF were targeted for a deletion. In such a way, the deletion plasmids for the lactate dehydrogenase ldhA, pSacB_delta_ldhA (SEQ ID NO: 10), the pyruvate formate lyase activating enzyme pflA, pSacB_delta_pflA (SEQ ID NO: 11) and the pyruvate formate lyase pflD, pSacB_delta_pflD (SEQ ID NO: 12) were constructed. FIGS. 2, 3 and 4 show schematic maps of plasmid pSacB_delta_ldhA, pSacB_delta_pflA and pSacB_delta_pflD, respectively.

In the plasmid sequence of pSacB (SEQ ID NO: 9) the sacB-gene is contained from bases 2380-3801. The sacB-promotor is contained from bases 3802-4264. The chloramphenicol gene is contained from base 526-984. The origin of replication for *E. coli* (ori EC) is contained from base 1477-2337 (see FIG. 1).

In the plasmid sequence of pSacB_delta_ldhA (SEQ ID NO: 10) the 5' flanking region of the ldhA gene, which is homologous to the genome of *Basfia succiniciproducens*, is contained from bases 1519-2850, while the 3' flanking region of the ldhA-gene, which is homologous to the genome of *Basfia succiniciproducens*, is contained from bases 62-1518. The sacB-gene is contained from bases 5169-6590. The sacB-promoter is contained from bases 6591-7053. The chloramphenicol gene is contained from base 3315-3773. The origin of replication for *E. coli* (ori EC) is contained from base 4266-5126 (see FIG. 2).

In the plasmid sequence of pSacB_delta_pflA (SEQ ID NO: 11) the 5' flanking region of the pflA-gene, which is homologous to the genome of *Basfia succiniciproducens*, is contained from bases 1506-3005, while the 3' flanking region of the pflA-gene, which is homologous to the genome of *Basfia succiniciproducens*, is contained from bases 6-1505. The sacB-gene is contained from bases 5278-6699. The sacB-promoter is contained from bases 6700-7162. The chloramphenicol gene is contained from base 3424-3882. The origin of replication for *E. coli* (ori EC) is contained from base 4375-5235 (see FIG. 3).

In the plasmid sequence of pSacB_delta_pflD (SEQ ID NO: 12) the 5' flanking region of the pflD-gene, which is homologous to the genome of *Basfia succiniciproducens*, is contained from bases 1533-2955, while the 3' flanking region of the pflD-gene, which is homologous to the genome of *Basfia succiniciproducens*, is contained from bases 62-1532. The sacB-gene is contained from bases 5256-6677. The sacB-promoter is contained from bases 6678-7140. The chloramphenicol gene is contained from base 3402-3860. The origin of replication for *E. coli* (ori EC) is contained from base 4353-5213 (see FIG. 4).

Example 3: Generation of Improved Succinate Producing Strains

Generation of Deletion Mutants:
a) *Basfia succiniciproducens* DD1 was transformed as described above with the pSacB_delta_ldhA and "Campbelled in" to yield a "Campbell in" strain. Transformation and integration into the genome of *Basfia succiniciproducens* was confirmed by PCR yielding bands for the integration event of the plasmid into the genome of *Basfia succiniciproducens*.

The "Campbell in" strain was then "Campbelled out" using agar plates containing sucrose as a counter selection medium, selecting for the loss (of function) of the sacB-gene. Therefore, the "Campbell in" strains were incubated in 25-35 ml of non selective medium (BHI containing no antibiotic) at 37° C., 220 rpm over night. The overnight culture was then streaked onto freshly prepared BHI containing sucrose plates (10%, no antibiotics) and incubated overnight at 37° C. ("first sucrose transfer"). Single colony obtained from first transfer were again streaked onto freshly prepared BHI containing sucrose plates (10%) and incubated overnight at 37° C. ("second sucrose transfer"). This procedure was repeated until a minimal completion of five transfers ("third, forth, fifth sucrose transfer") in sucrose. The term "first to fifth sucrose transfer" refers to the transfer of a strain after chromosomal integration of a vector containing a sacB-levan-sucrase gene onto sucrose and growth medium containing agar plates for the purpose of selecting for strains with the loss of the sacB-gene and the surrounding plasmid sequences. Single colony from the fifth transfer plates were inoculated onto 25-35 ml of non selective medium (BHI containing no antibiotic) and incubated at 37° C., 220 rpm over night. The overnight culture was serially diluted and plated onto BHI plates to obtain isolated single colonies.

The "Campbelled our" strains containing either the wild-type situation of the ldhA-locus or the mutation/deletion of the ldhA-gene were confirmed by chloramphenicol sensitivity. The mutation/deletion mutants among these strains were identified and confirmed by PCR analysis. This led to the ldhA-deletion mutant *Basfia succiniciproducens* DD1 ΔldhA.

b) *Basfia succiniciproducens* DD1 ΔldhA was transformed with pSacB_delta_pflA as described above and "Campbelled in" to yield a "Campbell in" strain. Transformation and integration was confirmed by PCR. The "Campbell in" strain was then "Campbelled our" as described previously. The deletion mutants among these strains were identified and confirmed by PCR analysis. This led to the ldhA pflD-double deletion mutant *Basfia succiniciproducens* DD1 ΔldhA ΔpflA.

c) *Basfia succiniciproducens* ΔldhA was transformed with pSacB_delta_pflD as described above and "Campbelled in" to yield a "Campbell in" strain. Transformation and integration was confirmed by PCR. The "Campbell in" strain was then "Campbelled our" as described previously. The deletion mutants among these strains were identified and confirmed by PCR analysis. This led to the ldhA pflD-double deletion mutant *Basfia succiniciproducens* DD1 ΔldhA ΔpflD.

Example 4: Determination of Glucose or Glycerol Consumption Rate for DD1 ΔldhA ΔpflA 1. Medium Preparation The composition of the cultivation medium used for the seed culture is described in table 1. For the main culture fermentation, the medium used is described in table 2.

TABLE 1

Medium composition for cultivation of the seed culture

| Compound | Concentration [g/L] |
| --- | --- |
| Yeast extract (Bio Springer) | 12.5 |
| $(NH_4)_2SO_4$ | 0.05 |
| succinic acid | 2.5 |
| $Na_2CO_3$ | 2 |
| $KH_2PO_4$ | 1 |
| $MgCO_3$ | 50 |
| glucose | 50 |

TABLE 2

Medium composition for cultivation of the main culture

| Compound | Concentration [g/L] |
| --- | --- |
| Yeast extract (Bio Springer) | 12.5 |
| $(NH_4)_2SO_4$ | 0.05 |
| betaine | 0.23 |
| $Na_2CO_3$ | 2 |
| $KH_2PO_4$ | 1 |
| Polypropylene glycol (antifoam) | 50 |
| glucose | 50 |

2. Cultivations and Analytics

The main culture was inoculated after one seed culture step. For the seed culture, the medium described in table 1 was prepared by autoclaving the water, $MgCO_3$ and $Na_2CO_3$ in a 2 L bottle. The other components were prepared and sterilized separated and added to the bottle afterwards in a sterile manner. 1% of cryo stocks were inoculated in a 2 L bottle containing 1800 mL of the liquid medium described above. A $CO_2$ atmosphere was applied in the bottle. The starting pH of the medium was in the range of 7.5 to 8.0 due to the presence of $MgCO_3$ and the $CO_2$ atmosphere. The incubation was performed at 37° C., 170 rpm (shaking diameter: 2.5 cm) under anaerobic conditions for 12 hours. The culture reached $OD_{600\ nm}$ of 21.

A total of 5% of the seed culture described above was used to inoculate the main culture. The main culture was performed in 1 L-fermenters containing an initial volume of 500 mL of the liquid medium described in table 2. The medium was prepared by autoclaving the water, $Na_2CO_3$ and antifoam in the fermenter. The other components were prepared separated as solutions and added to the fermenter afterwards in a sterile manner. Glucose was used as the carbon source for these fermentations in order to determine its consumption rate by the succinic acid producing strain. 45 g/L of glucose was batched in the medium and also provided along the fermentation by feeding which was added at a rate of 2 g/L/h. The feeding started 4 h after the start of the fermentation. Glucose was in an excess amount during the entire fermentation time and it was measured by HPLC as described in the next section (an excess amount of glucose was confirmed by the fact the that detectable glucose concentration in the fermentation was always above 1 g/L). A pH 6.5 was kept constant during the fermentation and it was controlled by the addition of magnesium hydroxide 15 wt-%. $CO_2$ was applied in the fermenter at flow of 0.1 vvm and the steering rate was 500 rpm. The analytics of the seed culture and the main culture are described in the next section.

3. Analytics

The production of carboxylic acids was quantified via HPLC. The details about the HPLC method applied are described in table 3 and 4. Cell growth was measured by measuring the absorbance at 600 nm ($OD_{600\ nm}$) using a spectrophotometer (Ultrospec3000, Amersham Biosciences, Uppsala Sweden).

TABLE 3

HPLC method (ZX-THF50) for analysis of glycerol, glucose and succinic acid

| HPLC column | Aminex HPX-87 H, 300 × 7.8 mm (BioRad) |
| --- | --- |
| Precolumn | Cation H |
| Temperature | 50° C. |
| Eluent flow rate | 0.50 ml/min |
| Injection volume | 5.0 μl |
| Diode array detector | RI-Detector |
| Runtime | 28 min |
| max. pressure | 140 bar |
| Eluent A | 5 mM $H_2SO_4$ |
| Eluent B | 5 mM $H_2SO_4$ |

| | Time [min] | A [%] | B [%] | Flow [ml/min] |
| --- | --- | --- | --- | --- |
| Gradient | 0.0 | 50 | 50 | 0.50 |
| | 28.0 | 50 | 50 | 0.50 |

4. Results

To calculate the glucose consumption rate, fermentation with batched glucose was performed. In this fermentation, glucose was in excess to allow for the calculation of the glucose consumption rate over time. The concentration of glucose was checked offline by HPLC during the fermentation and glucose was always detected in the medium. The measurements confirmed that glucose was always in excess in the medium. In this experiment 45 g/L of glucose was batched and a feeding rate of 2 g/L/h was applied after 4 hours.

TABLE 5

Glucose consumption rate for different time intervals of the succinic acid fermentation with *Basfia* DD1 ΔldhA ΔpflD described above

|  | Time interval [h] | | | |
| --- | --- | --- | --- | --- |
|  | 0-9 | 9-15 | 15-23 | 23-40 |
| Glucose consumption rate [g/L/h] | 2.76 | 3.87 | 2.22 | 1.61 |

In order to calculate the consumption rate, the amount of glucose consumed in certain time interval was determined.

Example 5: Comparison of Fermentations with DD1 ΔldhA ΔpflA Using Glycerol in Combination with Limited or Unlimited Glucose 5. Medium Preparation The composition of the cultivation media used for the seed culture and for the main culture are described in the previous section (example 4).

6. Cultivations and Analytics

The main culture is inoculated from a seed train consisting of one seed culture. For the seed culture 1% of cryo stocks were inoculated in a 2 L bottle with containing 1800 ml of the liquid medium described in table 1 with a $CO_2$ atmosphere. The starting pH of the medium was in the range of 7.5 to 8.0 due to the presence of $MgCO_3$ and the $CO_2$ atmosphere. The incubation was overnight at 37° C. and 170 rpm (shaking diameter: 2.5 cm) under anaerobic conditions for 12 hours ($OD_{600\ nm}$ of 21).

A total of 5% of the seed culture was used to inoculate the main culture in 1 L-fermenters containing an initial volume of 500 mL of the liquid medium described in table 2. Glycerol and glucose were the carbon sources. 54 g/L of glycerol and 8 g/L of glucose were provided by batch before the start of the fermentation. Glycerol was kept in excess during the entire fermentation and glucose was fed in rates that provided either limited or non-limited amounts of glucose for the cells. The feed is considered limited when the feeding rate is lower than the consumption rate of glucose that was previously determined. The feed started after 4 hours of fermentation and the feeding rate of glucose was either 2.5 g/L/h (unlimited) or 0.25 g/L/h (limited). The base utilized was magnesium hydroxide 15 wt.-%. $CO_2$ was applied in the fermenter at flow of 0.1 vvm and the steering rate was 500 rpm. The analytics of the seed culture and the main culture have been performed as described in the previous section (table 3). The concentration of glucose was checked offline by HPLC during the fermentation and glucose was always detected in the medium when fed with 2.5 g/L/h. When the limited feed of glucose was applied (0.25 g/L/h), the sugar was not detected in the culture supernatant during a certain time interval.

7. Results

7a. Determination of Glucose Consumption Rate

In this experiment 8 g/L of glucose and 54 g/L of glycerol were batched before the start of the fermentation and a feeding rate of 2.5 g/L/h of glucose were applied after 4 hours of fermentation. The glucose consumption rate was calculated as described in example 4 and the results for each time interval for this specific experimental set up are described in table 6. In this experiment the detectable glucose concentration in the fermentation was always above 1 g/L. The consumption rate for glycose given in table 6 thus represent the "maximum theoretical consumption rate for the further carbonaceous compound $CR_{c.c.\ max}$" under the given culture conditions.

TABLE 6

Glucose consumption rate for different time intervals of the succinic acid fermentation with *B. succiniciproducens* DD1 ΔldhA ΔpflD

|  | Time interval [h] | | | |
| --- | --- | --- | --- | --- |
|  | 0-9 | 9-15 | 15-23 | 23-40 |
| Glucose consumption rate [g/L/h] | 0.94 | 2.48 | 2.09 | 1.29 |

7b. Comparison Between Limited and Unlimited Feed of Glucose in the Succinic Acid Titer and Space Time Yield of Fermentations with B. *Succiniciproducens* DD1 ΔldhA ΔpflD After determination of the glucose consumption rate described above, either limited or unlimited feed of glucose were applied in fermentations. The different feeding rates to provide the limited and unlimited glucose concentrations are shown in table 7. The succinic acid titer and space time yield are also shown in table 7.

TABLE 7

Comparison between limited and unlimited feed of glucose in the production of succinic acid

|  | Feeding rate [g/L/h] | |
| --- | --- | --- |
| [Concentration (g/L)], time (h) | Unlimited Feed 2.5 g/L/h | Limited Feed 0.25 g/L/h |
| [Glycerol] t = 0 | 54 | 54 |
| [Glucose] t = 0 | 8 | 8 |
| [Glucose] t = 23 h | 25 | 0 |
| [Succinic acid] t = 0 | 1.5 | 1.5 |
| [Succinic acid] t = 23 h | 25.3 | 50.6 |
| Space time yield [g/L/h] | 1.035 | 2.135 |

When feeding glucose with a rate of 0.25 g/L/h (limited feed), the glucose concentration in the fermentation was always below the detection limit.

The results show an increase in the titer of succinic acid produced and a higher space time yield when glucose is added in a limited way.

Example 6: Comparison Between Different Limited Feeds of Glucose in a Fermentation with *B. succiniciproducens* DD1 ΔldhA ΔpflD 8. Medium Preparation The compositions of the cultivation media used for the seed culture and for the main culture are described in the section 1 (example 4).

9. Cultivations and Analytics

The main culture is inoculated from a seed train consisting of one seed culture. For the seed culture 1% of cryo stocks were inoculated in a 2 L bottle with containing 1800 ml of the liquid medium described in table 1 with a $CO_2$ atmosphere. The starting pH of the medium was in the range of 7.5 to 8.0 due to the presence of $MgCO_3$ and the $CO_2$ atmosphere. The incubation was overnight at 37° C. and 170 rpm (shaking diameter: 2.5 cm) under anaerobic conditions for 12 hours ($OD_{600\ nm}$ of 21).

A total of 5% of the seed culture was used to inoculate the main culture in 1 L-fermenters containing an initial volume of 500 mL of the liquid medium described in table 2. Glycerol and glucose were the carbon sources. 50 g/L of glycerol and 8 g/L of glucose were provided by batch before the start of the fermentation. Glycerol was kept in excess during the entire fermentation and glucose was fed in rates that provided limited amounts of glucose for the cells. The feed is considered limited when the feeding rate is lower than the consumption rate of glucose that was previously determined. The feed started after 4 hours of fermentation and the feeding rates of glucose are described in table 8. The base utilized was magnesium hydroxide 15 wt-%. $CO_2$ was applied in the fermenter at flow of 0.1 vvm and the steering rate was 500 rpm. The analytics of the seed culture and the main culture have been performed as described in the previous section (table 3). The concentration of glucose was checked offline by HPLC during the fermentation and glucose not detected in the culture supernatant during a certain time interval.

10. Results

After calculating the glucose consumption rate as described in example 1, fermentations with feeding rates of glucose lower than the consumption rate (limited feed) were performed. Glycerol is in excess in the fermentation. The succinic acid titer and the space time yield are directly influenced by the amount of glucose fed into the fermenter (table 8). The results observed in table 8 confirm that in fermentations where glycerol is the main carbon source, the amount of succinic acid and the space time yield are improved with limited amounts of glucose. The lower the feeding rate of glucose, the higher is the succinic acid titer and the space time yield.

TABLE 8

Influence of limited feeding rates of glucose in combination with an excess of glycerol on the titer and the space time yield of succinic acid fermentation by *Basfia succiniciproducens* DD1 ΔldhA ΔpflA.

| Feed rate glucose [g/L/h] | Succinic acid titer [%] | Space time yield [g succinic acid/L/time (h)] |
|---|---|---|
| 0.93 | 100 | 2.5 |
| 0.56 | 105 | 2.62 |
| 0.37 | 112 | 2.76 |

The examples show that limited amounts of glucose are beneficial when using glycerol as the main C-source for succinic acid fermentations.

SEQUENCES

SEQ ID NO: 1 (nucleottde sequence of 16 S rDNA of stratn DD1)
tttgatcctggctcagattgaacgctggcggcaggcttaacacat
gcaagtcgaacggtagcgggaggaaagcttgctttctttgccga
cgagtggcggacgggtgagtaatgcttggggatctggcttatgga
ggggataacgacgggaaactgtcgctaataccgcgtaatat
cttcggattaaagggtgggactttcgggccacccgccataagatg
agcccaagtgggattaggtagttggtggggtaaaggcctacc
aagccgacgatctctagctggtctgagaggatgaccagccacact
ggaactgagacacggtccagactcctacgggaggcagca
gtggggaatattgcacaatgggggaaccctgatgcagccatgcc
gcgtgaatgaagaaggccttcgggttgtaaagttctttcggtg
acgaggaagtgtttgttttaataggacaagcaattgacgttaat
cacagaagaagcaccggctaactccgtgccagcagccgcggt
aatacggagggtgcgagcgttaatcggaataactgggcgtaaagg
gcatgcaggcggacttttaagtgagatgtgaaagccccgg
gcttaacctgggaattgcatttcagactgggagtctagagtactt
tagggaggggtagaattccacgtgtagcggtgaaatgcgtagag
atgtggaggaataccgaaggcgaaggcagcccccttgggaagatac
tgacgctcatatgcgaaagcgtggggagcaaacaggatt
agatacctggtagtccacgcggtaaacgctgtcgatttgggat
tgggctttaggcctggtgctcgtagctaacgtgataaatcgacc
gcctggggagtacggccgcaaggttaaaactcaaatgaattgacg
ggggcccgcacaagcggtggagcatgtggtttaattcgatg
caacgcgaagaaccttacctactcttgacatccagagaatcctgt
agagatacgggagtgccttcgggagctctgagacaggtgctg
catggctgtcgtcagctcgtgttgtgaaatgttgggttaagtccc
gcaacgagcgcaacccttatccttgttgccagcatgtaaagatgg
gaactcaaaggagactgccggtgacaaaccggaggaaggtgggat
gacgtcaagtcatcatggcccttacgagtagggctaca
cacgtgctacaatggtgcatacagagggcggcgataccgcgaggta
gagcgaatctcagaaagtgcatcgtagtccggattggagt
ctgcaactcgactccatgaagtcggaatcgctagtaatcgcaaatc
agaatgttgcggtgaatacgttcccgggccttgtacacaccg
cccgtcacaccatgggagtgggttgtaccagaagtagatagcttaa
ccttcggggggggcgtttaccacggtatgattcatgactggg
gtgaagtcgtaacaaggtaaccgtaggggaacctgcgg SEQ ID NO: 2 (nucleottde sequence of 23 S rDNA of stratn DD1)
agtaataacgaacgacacaggtataagaatacttgaggttgtat
ggttaagtgactaagcgtacaaggtggatgccttggcaatcaga
ggcgaagaaggacgtgctaatctgcgaaaagcttgggtgagttg
ataagaagcgtctaacccaagatatccgaatggggcaaccc
agtagatgaagaatctactatcaataaccgaatccataggttat
tgaggcaaaccgggagaactgaaacatctaagtaccccgagg
aaaagaaatcaaccgagattacgtcagtagcggcgagcgaaagc
gtaagagccggcaagtgatagcatgaggattagaggaat
cggctgggaagccgggcggcacagggtgatagcccccgtacttga
aaatcattgtgtggtactgagcttgcgagaagtagggcggga
cacgagaaatcctgtttgaagaaggggggaccatcctccaaggc
taaatactcctgattgaccgatagtgaaccagtactgtgaagg
aaaggcgaaaagaacccccggtgaggggagtgaaatagaacctga
aaccttgtacgtacaagcagtgggagcccgcgcgagggtga
ctgcgtacctttgtataatgggtcagcgacttatattatgtag
cgaggttaaccgaataggggagccgaagggaaaccgagtcttaact
gggcgtcgagttgcatgatatagacccgaaacccggtgatctagcc
atgggcaggttgaaggttgggtaacactaactggaggacc
gaaccgactaatgttgaaaaattagcggatgacctgtggctgggg
tgaaaggccaatcaaaccgggagatagctggttctccccg
aaatctatttaggtagagcctatgtgaatccttcgggggtagag
cactgtttcggctaggggccatcccggcttaccaacccgatgc
aaactgcgaataccgaagagtaatgcataggagacacacggcggt
gctaacgttcgtcgtggagagggaaacaacccagacc
gccagctaaggtcccaaagtttatattaagtgggaaacgaagtggg
aaggcttagacagctaggatgttggcttagaagcagccatc
atttaaagaaagcgtaatagctcactagtcgagtcggcctgcgcgg
aagatgtaacggggctcaaatatagcaccgaagctgcggc
atcaggcgtaagcctgttgggtaggggagcgtcgtgtaagcggaag
aaggtggttcgagagggctgctggacgtatcacgagtgcg
aatgctgacataagtaacgataaaacgggtgaaaaacccgttcgcc
ggaagaccaaggggttcctgtccaacgttaatcggggcag
ggtgagtcggcccctaaggcgaggctgaagagcgtagtcgatggga
aacgggttaatattcccgtacttgttataattgcgatgtggg
gacggagtaggttaggttatcgacctgttggaaaaggtcgtttaag
ttggtaggtggagcgtttaggcaaatccggacgcttatcaaca
ccgagagatgatgacgaggcgctaaggtgccgaagtaaccgatacc
acacttccaggaaaagccactaagcgtcagattataata

```
aaccgtactataaaccgacacaggtggtcaggtagagaatactcag
gcgcttgagagaactcgggtgaaggaactaggcaaaata
gcaccgtaacttcgggagaaggtgcgccggcgtagattgtagaggt
ataccctttgaaggttgaaccggtcgaagtgacccgctggct
gcaactgtttattaaaaacacagcactctgcaaacacgaaagtgga
cgtatagggtgtgatgcctgcccggtgctggaaggttaattg
atggcgttatcgcaagagaagcgcctgatcgaagccccagtaaacg
gcggccgtaactataacggtcctaaggtagcgaaattcctt
gtcgggtaagttccgacctgcacgaatggcataatgatggccaggc
tgtctccacccgagactcagtgaaattgaaatcgccgtgaa
gatgcggtgtacccgcggctagacggaaagaccccgtgaaccttta
ctatagcttgacactgaaccttgaattttgatgtgtaggatag
gtgggaggcttttgaagcggtaacgccagttatcgtggagccatcctt
gaaataccaccctttaacgtttgatgtctaacgaagtgcccg
gaacgggtactcggacagtgtctggtgggtagtttgactggggcggt
ctcctcccaaagagtaagcgaggagcacgaaggtttgcta
atgacggtcggacatcgtcaggttagtgcaatggtataagcaagctt
aactgcgagacggacaagtcgagcaggtgcgaaagcag
gtcatagtgatccggtggttctgaatggaagggccatcgctcaacgg
ataaaaggtactccggggataaacaggctgataccgccca
agagttcatatcgacggcggtgtttggcacctcgatgtcggctcatc
acatcctggggctgaagtaggtcccaaggggtatggctgttcgc
catttaaagtggtacgcgagctgggtttaaaacgtcgtgagacagtt
tggtccctatctgccgtgggcgttggagaattgagaggggct
gctcctagtacgagaggaccggagtggacgcatcactggtgttccgg
ttgtgtcgccagacgcattgccgggtagctacatgcggaa
gagataagtgctgaaagcatctaagcacgaaacttgcctcgagatga
gttctcccagtatttaatactgtaagggttgttggagacgac
gacgtagataggccgggtgtgtaagcgttgcgagacgttgagctaac
cggtactaattgcccgagaggcttagccataccaacgctca
agtgtttttggtagtgaaagttattacggaataagtaagtagtcagg
gaatcggct SEQ ID NO: 3 (nucleottde sequence of IdhA-gene
from stratn DD1)
ttgacaaaatcagtatgtttaaataaggagctaactatgaaagttgc
cgtttacagtactaaaaattatgatcgcaaacatctggatttgg
cgaataaaaaatttaattttgagcttcatttctttgattttttactt
gatgaacaaaccgcgaaaatggcggagggcgccgatgccgtctgta
ttttcgtcaatgatgatgcgagccgccggtgttaacaaagttggcg
caaatcggagtgaaaattatcgctttacgttgtgccggtttaat
aatgtggatttggaggcggcaaaagagctgggattaaaagtcgtacg
ggtgcctgcgtattcgccgaagccgttgccgagcatgcg
atcggattaatgctgactttaaaccgccgtatccataaggcttatca
gcgtacccgcgatgcgaattttttctctggaaggattggtcggtttt
aatatgttcggcaaaaccgccggagtgattggtacgggaaaaatcgg
cttggcggctattcgcattttaaaaggcttcggtatggacgtt
ctggcgtttgatccttttaaaaatccggcggcggaagcgttgggcgc
aaaatatgtcggtttagacgagcttttatgcaaagaactgtta
tcactttgcattgcccggctacggcggataattatcatttattaaat
gaagcggcttttaataaaatgcgcgacggtgtaatgattattaata
ccagccgcggcgttttaattgacagccgggcggcaatcgaagcgtta
aaacggcagaaaatcggcgctctcggtatggatgtttatg
aaaatgaacgggatttgttttttcgaggataaatctaacgatgttata
cggatgatgtattccgtcgcctttcttcctgtcataatgtgcttttta
ccggtcatcaggcgttttaacggaagaagcgctgaataatatcgccg
atgtgactttatcgaatattcaggcggtttccaaaaatgcaac
gtgcgaaaatagcgttgaaggctaa SEQ ID NO: 4 (amino acid sequence of IdhA from
strain DD1)
MTKSVCLNKELTMKVAVYSTKNYDRKHLDLANKKFNFELHFFDFLLDEQ
TAKMAEGADAVCIFVNDDASRPVLTKLAQIGVKIIALRCAGFNNVDLE
AAKELGLKVVRVPAYSPEAVAEHAIGLMLTLNRRIHKAYQRTRDANFSL
EGLVGFNMFGKTAGVIGTGKIGLAAIRILKGFGMDVLAFDPFKNPAAE
ALGAKYVGLDELYAKSHVITLHCPATADNYHLLNEAAFNKMRDGVMIIN
TSRGVLIDSRAAIEALKRQKIGALGMDVYENERDLFFEDKSNDVITDDV
FRRLSSCHNVLFTGHQAFLTEEALNNIADVT
LSNIQAVSKNATCENSVEG SEQ ID NO: 5 (nucleottde sequence of pflA-gene
from strain DD1)
atgtcggttttaggacgaattcattcatttgaaacctgcgggacagt
tgacgggccgggaatccgctttattttattttttacaaggctgcttaa
tgcgttgtaaatactgccataatagagacacctgggatttgcacggc
ggtaaagaaatttccgttgaagaattaatgaaagaagtggtg
acctatcgccattttatgaacgcctcgggcggcgagttaccgcttc cggcggtgaagctattttacaggcggaatttgtacgggactgg
ttcagagcctgccataaagaaggaattaatacttgcttggataccaa
cggttcgtccgtcatcatgatcatattattgatgaattgattgat
gacacggatcttgtgttgcttgacctgaaagaaatgaatgaacgggt
tcacgaaagctgattggcgtgccgaataaaagagtgctcg
aattcgcaaaatatttagcggatcgaaatcagcgtacctggatccgc
catgttgtagtgccgggtttacagatagtgacgaagatttgc
acatgctggggaatttcattaaagatatgaagaatatcgaaaaagtg
gaattattaccttatcaccgtctaggcgcccataaatgggaa
gtactcggcgataaatacgagcttgaagatgtaaaaccgccgacaaa
agaattaatggagcatgttaaggggttgcttgcaggctac
gggcttaatgtgacatattag SEQ ID NO: 6 (amtno acid sequence of PflA from
strain DD1)
MSVLGRIHSFETCGTVDGPGIRFILFLQGCLMRCKYCHNRDTWDLH
GGKEISVEELMKEVVTYRHFMNASGGGVTASGGEAILQAEFVRDWFR
ACHKEGINTCLDTNGFVRHHDHIIDELIDDTDLVLLDLKEMNERVHE
SLIGVPNKRVLEFAKYLADRNQRTWIRHVVVPGYTDSDEDLHMLGNFI
KDMKNIEKVELLPYHRLGAHKWEVLGDKYELEDVKPPTKELMEHVKGL
LAGYGLNVTY SEQ ID NO: 7 (nucleotide sequence of pflD-gene
from strain DD1)
atggctgaattaacagaagctcaaaaaaaagcatgggaaggatt
cgttccggtgaatggcaaaacggcgtaaatttacgtgacttt
atccaaaaaaactatactccgtatgaaggtgacgaatcattctt
agctgatgcgactcctgcaaccagcgagttgtggaacagcgtga
tggaagcgcatcaaaatcgaaaacaaaactcacgcacctttagat
ttcgacgaacatactccgtcaactatcacttctcacaagctgg
ttatatcaataaagatttagaaaaaatcgttggtcttcaaacag
acgctccgttaaaacgtgcaattatgccgtacggcggtatcaaat
gatcaaaggttcttgcgaagtttacggtcgtaaattagatccg
aagtagaatttatttcaccgaatatcgtaaaacccataaccaagg
cgtattcgacgtttatacgccggatattttacgctgccgtaaat
caggcgtgttaaccggtttaccggatgcttacggtcgtggtcgt
attatcggtgactaccgtcgtttagcggtatacggtattgattac
ctgatgaaagataaaaaagcccaattcgattcattacaaccgcgt
ttggaagcgggcgaagacattcaggcaactatccaattacgtgaa
gaaattgccgaacaacaccgcgctttaggcaaaatcaaagaaatgg
cggcatcttacggttcacaatttccggccctgcgaacgcac
aggaagcaatccaatggacatattttgcttatctcgcagcggtt
aaatcacaaaacggtgcggcaatgtcattcggtcgtacgtctacat
tcttagatatctatatcgaacgtgacttaaaacgcggtttaatca
ctgaacaacaggcgcaggaattaatggaccacttagtaatgaaatt
acgtatggttcgtttcttacgtacgccggaatacgatcaattatt
ctcaggcgacccgatgtgggcaaccgaaactatcgccggtatgggc
ttagacggtcgtccgttggtaactaaaaacagcttccgcgt
attacatactttatacactatgggtacttctccggaaccaaactta
actattctttggtccgaacaattacctgaagcgttcaaacgtttctgt
gcgaaagtatctattgatacttcctccgtacaatacgaaatgatga
cttaatgcgtcctgacttcaacaacgatgactatgcaatcgcat
gctgcgtatcaccgatggtcgtaaagtaaacaaatgcaattcttcggt
gcgcgcgcaaactagctaaactatgttatacgcaattaac
ggcggtatcgatgagaaaatggtatgcaagtcggtcctaaaactgcg
ccgattacagacgaagtattgaatttcgataccgtaatcg
aacgtatggacagtttcatggactggttggcgactcaatatgtaaccg
cattgaacatcatccacttcatgcacgataaatatgcatatg
aagcggcattgatggcgttccacgatcgcgacgtattccgtacaatgg
cttgcggtatcgcgggtctttccgtggctgcggactcattatc
cgcaatcaaatatgcgaaagttaaaccgattcgcggcgacatcaaaga
taaagacgtaatgtcgtggcctcgaatgttgctatcga
cttcgaaattgaaggcgaatatccgcaattcggtaacaatgatccgcg
tgttgatgatttagcggtagacttagttgaacgtttcatgaaa
aaagttcaaaaacacaaaacttaccgcaacgcaactccgacacaatct
atcctgactatcacttctaacgtggtatacggtaagaaa
accgatcatccgcagcggtcgtcgagcaggcgcgccattcggaccg
ggtgcaaacccaatgcacggtcgtgaccaaaaaggt
gcggttgcttcacttacttctgtggctaaacttccgttcgcttacgcg
aaagacggtatttcatataccttctctatcgtaccgaacgcattag
gtaaagatgacgaagcgcaaaaacgcaaccttgccggttaatggacg
gttatttccatcatgaagcgacagtggaaggcggtcaa
cacttgaatgttaacgttcttaacgctgaaattgttgttagacgcgatg
gaaaatccggaaaaatacccgcaattaaccattcgtgtttcag
gttacgcggttcgtttcaactcattaactaaagagcaacaacaagacg
tcatcactcgtacgtttacacaatcaatgtaa
```

SEQ ID NO: 8 (amino acid of PflD from strain DD1)
MAELTEAQKKAWEGFVPGEWQNGVNLRDFIQKNYTPYEGDESFLADAT
PATSELWNSVMEGIKIENKTHAPLDFDEHTPSTITSHKPGYINKDLEK
IVGLQTDAPLKRAIMPYGGIKMIKGSCEVYGRKLDPQVEFIFTEYRKT
HNQGVFDVYTPDILRCRKSGVLTGLPDAYGRGRIIGDYRRLAVYGIDY
LMKDKKAQFDSLQPRLEAGEDIQATIQLREEIAEQHRALGKIKEMAAS
YGYDISGPATNAQEAIQWTYFAYLAAVKSQNGAAMSFGRTSTFLDIYI
ERDLKRGLITEQQAQELMDHLVMKLRMVRFLRTPEYDQLFSGDPMWAT
ETIAGMGLDGRPLVTKNSFRVLHTLYTMGTSPEPNLTILWSEQLPEAF
KRFCAKVSIDTSSVQYENDDLMRPDFNNDDYAIACCVSPMVVGKQMQF
FGARANLAKTMLYAINGGIDEKNGMQVGPKTAPITDEVLNFDTVIERM
DSFMDWLATQYVTALNIIHFMHDKYAYEAALMAFHDRDVFRTMACGIA
GLSVAADSLSAIKYAKVKPIRGDIKDKDGNVVASNVAIDFEIEGEYPQ
FGNNDPRVDDLAVDLVERFMKKVQKHKTYRNATPTQSILTITSNVVYG
KKTGNTPDGRRAGAPFGPGANPMHGRDQKGAVASLTSVAKLPFAYAKD
GISYTFSIVPNALGKDDEAQKRNLAGLMDGYFHHEATVEGGQHLNVNV
LNREMLLDAMENPEKYPQLTIRVSGYAVRFNSLTKEQQQDVITRT
FTQSM SEQ ID NO: 9 (complete nucleotide sequence of
plasmid pSacB)
tcgagaggcctgacgtcgggcccggtaccacgcgtcatatgacta
gttcggacctagggatatcgtcgacatcgatgctcttctgcgtt
aattaacaattgggatcctctagactccataggccgctttcctgg
ctttgcttccagatgtatgctctcctccggagagtaccgtgactt
tattttcggcacaaatacagggtcgatggataaatacggcgatag
tttcctgacggatgatccgtatgtaccggcggaagacaagctgca
aacctgtcagatggagattgatttaatggcggatgtgctgagagca
ccgccccgtgaatccgcagaactgatccgtatgtgtttgcgg
atgattggccggaataaataaagccgggcttaatacagattaagcc
cgtatagggtattattactgaataccaaacagcttacggagg
acggaatgttacccattgagacaaccagactgccttctgattatta
atattttttcactattaatcagaaggaataaccatgaatttttacccg
gattgacctgaatacctggaatcgcagggaacactttgcccttat
cgtcagcagattaaatgcggattcagcctgaccaccaaactcg
atattaccgctttgcgtaccgcactggcggagacaggttataagtt
ttatccgctgatgattacctgatctcccgggctgttaatcagttt
ccggagttccggatggcactgaaagacaatgaacttatttactggg
accagtcagacccggtctttactgtctttcataaagaaaccgaaa
cattctctgcactgtcctgccgttattttccggatctcagtgagtt
tatggcaggttataatgcggtaacggcagaatatcagcatgatacca
gattgtttccgcaggaaattaccggagaatcacctgaatatatca
tcattaccgtgggtgagttttgacgggatttaacctgaacatca
ccggaaatgatgattattttgccccggttttacgatggcaaagtt
tcagcaggaaggtgaccgcgtattattacctgtttctgtacaggttc
atcatgcagtctgtgatgtcttcatgcagcacggttattaatac
acttcagctgatgtgtgataacatactgaaataaattaattaattct
gtatttaagccaccgtatccggcaggaatggtggctttttttttata
ttttaaccgtaatctgtaattcgtttcaagactggttcaggatgagc
tcgcttggactcctgttgatagatccagtaatgacctcagaactcca
tctggattttgttcagaacgctcggttgccgccgggcgttttttattg
gtgagaatccaagcactagcggcgcgccgccggccggtgtgaaat
accgcacagatgcgtaaggagaaaataccgcatcaggcgctcttccg
cttcctcgctcactgactcgctgcgctcggtcgttcggctgcggcga
gcggtatcagctcactcaaaggcggtaatacggttatccacagaatc
aggggataacgcaggaaagaacatgtgagcaaaaggccagcaaaagg
ccaggaaccgtaaaaaggccgcgttgctggcgtttttccataggcte
cgcccccctgacgagcatcacaaaaatcgacgctcaagtcagaggtg
gcgaaacccgacaggactataaagataccaggcgtttccccctggaa
gctccctcgtgcgctctcctgttccgaccctgccgcttaccggatac
ctgtccgcctttctcccttcgggaagcgtggcgctttctcatagctc
acgctgtaggtatctcagttcggtgtaggtcgttcgctccaagctg
ggctgtgtgcacgaaccccccgttcagcccgaccgctgcgccttatc
cggtaactatcgtcttgagtccaacccggtaagacacgacttatcgc
cactggcagcagccactggtaacaggattagcagagcgaggtatgtag
gcggtgctacagagttcttgaagtggtggcctaactacggctaca
ctagaaggacagtatttggtatctgcgctctgctgaagccagttacc
ttcggaaaaagagttggtagctcttgatccggcaaacaaacc
accgctggtagcggtggtttttttgtttgcaagcagcagattacgcg
cagaaaaaaaggatctcaagaagatcctttgatctttctacgg
ggtctgacgctcagtggaacgaaaactcacgttaagggattttggtca
tgagattatcaaaaaggatcttcacctagatccttttaaagg
ccggccgcggccgccatcggcattttcttttgcgttttatttgttaa
ctgttaattgtccttgttcaaggatgctgtctttgacaacagatgttt
tcttgcctttgatgttcagcaggaagctcggcgcaaacgttgattgtt
tgtctgcgtagaatcctctgtttgtcatatagcttgtaatcacgacatt
gtttcctttcgcttgaggtacagcgaagtgtgagtaagtaaaggttac atcgttaggatcaagatccatttttaacacaaggccagttttgtt
cagcggcttgtatgggccagttaaagaattagaaacataaccaagcat
gtaaatatcgttagacgtaatgccgtcaatcgtcattttgat
ccgcgggagtcagtgaacaggtaccatttgccgttcattttaaagacgt
tcgccggttcaatttcatctgttactgtgttagatgcaatcagc
ggtttcatcacttttttcagtgtgtaatcatcgtttagctcaatcata
ccgagagcgccgtttgctaactcagccgtgcgtttttttatcgctttgca
gaagttttgacttcttgacgaagaatgatgtgcttttgccatagta
tgctttgttaaataaagattcttcgccttggtagccatcttcagttcc
agtgtttgcttcaaatactaagtatttgtggcctttatcttctacgtag
tgaggatctctcagcgtatggttgtcgcctgagctgtagttgcctt
atcgatgaactgctgtacattttgatacgttttccgtcaccgtcaaag
attgatttataatcctctacaccgttgatgttcaaagagctgtctg
atgctgatacgttaacttgtgcagttgtcagtgtttgtttgccgtaatg
tttaccggagaaatcagtgtaaaataaacggattttttccgtcaga
tgtaaatgtggctgaacctgaccattcttgtgttggtcttttaggata
gaatcattttgcatcgaatttgtcgctgtctttaaagacgcggccag
cgttttttccagctgtcaatagaagtttcgccgacttttttgatgaacat
gtaaatcgatgtgtcatccgcatttttaggatctccggctaatgc
aaagacgatgtggtagccgtgatagttttgcgacagtgcgtcagcgttt
tgtaatggccagctgtcccaaacgtccaggccttttgcaga
agagatattttaattgtggacgaatcaaattcagaaacttgatattttt
tcatttttttgctgttcagggatttgcagcatatcatgcgtgtaata
tggaaatgccgtatgtttccttatatgcttttggttcgtttcttc
gcaaacgcttgagttgcgcctcctgccacagtgcggtagtaaagg
ttaatactgttgctgttttgcaaacttttttgatgttcatcgttcatgt
ctcctttttttatgtactgtgttagcggtctgcttcttccagcccctg
tttgaagatggcaagttagttacgcaacaataaaaaaagaccttaaaatat
gtaaggggtgacgccaaagtatacactttgcccttttacacatttt
aggtcttgcctgctttatcagtaacaaacccgcgcgatttacttttcga
cctcattctattagactctcgtttggattgcaactggtctatttttcct
cttttgtttgataagaaatcataaaaggatttgcagactacgggcctaa
agaactaaaaatctatctgtttctttttcattctctgtatttttata
gtttctgttgcatgggcataaagttgccttttaatcacaattcagaaa
atatcataatatctcatttcactaaataatagtgaacgcaggt
atatgtgatgggttaaaaaggatcggcggccgctcgatttaaatc SEQ ID NO: 10 (complete nucleotide sequence of
plasmid pSacB_delta_ldhA)
tcgagaggcctgacgtcgggcccggtaccacgcgtcatatgactagtt
cggacctagggatatcgtcgacatcgatgctcttctgcgtgaacgcactt
gtatgtaggtagtttgaccgcccgaatattcgttataccttggtgga
aaaattcaaaccgatggagcaattatacaattttgtggcggcgc
aaaaaggtaaaagcggtatcgtctattgcaacagccgtagcaaag
tgggagcgcattgcgagcgcgtcgaaagaaaagaggcattc
cgcagccgcttatcatgcgggcatggagccgtcgcagcgggaagc
ggtgcaacaggcgtttcaacgggataatattcaagtggtgg
tggcgaccattgcttttggtatggggatcaacaaatctaatgtgc
gttttgttgcgcatttgattctcgcagcattgaggcgtattat
caggaaaccgcggcgcgggggcgacctgccggcggaagcggta
ctgttttacgagccggcggattatgcctggttgcataaaat
tttattggaagagccgaaagcccgcaacgggatatttaaacggca
taagctggaagccatcggcgaatttgccgaaagccagacc
tgccgtcgtttagtgctgttaaattatttcggcgaaaaccgccaaac
gccatgtaataactgtgatatctgcctcgatccgccgaaaaaat
atgacggattattagacgcgcagaaaatcctttcgaccatttatcgca
ccgggcaacgttcggcacgcaatacgtaatcggcgtaatg
cgcggtttgcagaatcagaaaataaaagaaaatcaactgatgagttg
aaagtctacggaattggcaaagataaaagcaaagaat
actggcaatcggtaattcgtcagctgattcatttgggctttgtgcaac
aaatcatcagcgatttcggcatggggaccagattacagctcac
cgaaagccgcgatttccttgtcgcggcgaagttgctttggaactggc
catgccgagattatcttccattaccatgtacaggctccgc
aacgcaatgcgtaaccaactacgacaaagatttatttgcccgcctgc
gtttcctgcgcaaacagattgccgacaaagaaaacattc
cgccttatattgtgtcagtgacgcgacctttgcaggaaatgtcgttgt
atcagccgacagccagcaaagtggaaatgctgcaaatcaacgt
gtcggcgccatcaaatggcagcgcttcggacagccttttatggcgatt
attaaagaacatcaggcttgtgctaaagcgggtaagaatc
cgttggaattgcaatcttaaaattttttaacttttttgaccgcactttta
aggttagcaaatttccaataaaaagtgcggtgggtttttcgggaatttttt
aacgcgctgattccttcgctctttaaaatttttcgctccatttgttc
ggyggttgccgatcctttcttgactgagatccataagagatgaa
tagccgcttatattttaatagctaaccgtaatcgggtacgctttt
tttatgcggaaaatccatattttttctaccgcacttttctcttaaaga
tttatacttaagtctgtttgattcaatttatttggaggttttatgcaa
cacattcaactggctcccgatttaacattcagtcgcttaattcaagga ttctggcggttaaaaagctggcggaaatcgccgcaggaattgcttaca
ttcgttaagcaaggattagaattaggcgttgatacgctggatcat
gccgcttgttacggggcttttacttccgaggcggaattcggacgggcg
ctggcgctggataaatccttgcgcgcacagcttactttggtg
accaaatgcgggattttgtatcctaatgaagaattacccgatataaat
cccatcactatgacaacagctaccgccatattatgtggtcg
gcgcaacgttccattgaaaaactgcaatgcgactatttagatgtattg
ctgattcaccgwcttttctccctgtgcggatcccgaacaaatcg
cgcgggcttttgatgaactttatcaaaccggraaagtacgttatttc
ggggtatctaactatacgccggctaagttcgccatgttgcaatctt
atgtgaatcagccgttaatcactaatcaaattgagatttcgcctcttc
atcgtcaggcttttgatgacggtaccctggatttttttactggaaaa
acgtattcaaccgatggcatggtcgccacttgccggcggtcgtttatt
caatcaggatgagaacagtcgggcggtgcaaaaaacattactcgaaat
cggtgaaacgaaaggagaaaccgtttagatacattggcttatgctg
gttattggcgcatccggcaaaaattatgccggttatgggtccggtaa
aattgaacgggtaaaaagcgcggcggatgcgttacgaatttccttcac
tgaggaagaatggattaaggtttatgttgccgcacagggacgggatatt
ccgtaacatcatccgtctaatcctgcgtatctggggaaagatgcgtca
tcgtaagaggtctataatatcgtcgttttgataagggtgcagtaa
ggcacccgttaaaatcacattgcgttcgcaacaaaattattccttac
gaatagcattcacctctttttaacagatgttgaatatccgtatcggca
aaaatatcctctatatttgcggttaaacggcgccgccagttagcatat
tgagtgctggttcccggaatattgacgggttcggtcataccgagcag
tcttcaggttggaatccccatcgtcgacatcgatgctcttctgcgtta
attaacaattgggatcctctagactccataggccgctttcctggctt
tgcttccagatgtatgctctcctccggagagtaccgtgactttattt
tcggcacaaatacagggggtcgatggataaatacggcgatagtttctg
acggatgatccgtatgtaccggcggaagacaagctgcaaacctgtca
gatggagattgatttaatggcggatgtgctgagagcaccgccccgtg
aatccgcagaactgatccgctatgtgtttgcggatgattggc
cggaataaatcaaagcgcgggcttaatacagattaagccgctataggggt
attattactgaataccaaacagcttacggaggacggaaatg
ttacccattgagacaaccagactgccttctgattattaatatttttca
ctattaatcagaaggaataaccatgaattttacccggattgacct
gaatacctggaatcgcagggaacacttgccctttatcgtcagcagat
taaatgcggattcagcctgaccaccaaactcgatattaccg
ctttgcgtaccgcactggcggagacaggttgataagtttatccgctg
atgatttacctgatctcccgggctgttaatcagtttccggagttcc
ggatggcactgaaagacaatgaacttatttactgggaccagtcagacc
cggtctttactgtctttcataaagaaaccgaaacattctctg
cactgtcctgccgttatttccggatctcagtgagttatggcaggt
tataatgcggtaacggcagaatatcagcatgataccagattgtttc
cgcagggaaatttaccggagaatcacctgaatatatcatcattaccg
tgggtgagttttgacgggatttaacctgaacatcaccggaaa
tgatgattatttgccccggtttttacgatggcaaagtttcagcagga
aggtgaccgcgtattattacctgtttctgtacaggttcatcatgca
gtctgtgatggctttcatgcagcacggtttattaatacacttcagctg
atgtgtgataacatactgaaatattaattcttcgtatttaagc
caccgtatccgcaggaatggtggcttttttttttatattttaaccgt
aatctgtaatttcgtttcagactggttcaggatgagctcgcttggac
tcctgttgatagatccagtaatgacctcagaactccatctggatttg
ttcagaacgctcggttgccgccgggcgttttttattggtgagatcc
aagcactagcggcgcgccgggccggtgtgaaataccgcacagat
gcgtaaggagaaataccgcatcaggcgctcttccgcttcctcgctc
actgactcgctgcgctcggtcgttcggctgcggcgagcggtatcagct
cactcaaaggcggtaatacggttatccacagaatcagggggataacgc
aggaaagaacatgtgagcaaaaggccagcaaaaggccaggaaccgta
aaaaggccgcgttgctggcgtttttccataggctccgcccccctgacg
agcatcacaaaaatcgacgctcaagtcagaggtggcgaaacccgaca
ggactataaagataccaggcgtttccccctggaagctccctcgtgcg
ctctcctgttccgaccctgccgcttaccggatacctgtccgcctttc
tcccttcgggaagcgtggcgctttctcatagctcacgctgtaggta
tctcagttcggtgtaggtcgttcgctccaagctgggctgtgtgcac
gaacccccgttcagcccgaccgctgcgccttatccggtaactat
cgtcttgagtccaacccggtaagacacgacttatcgccactggcag
cagccactggtaacaggattagcagagcgaggtatgtaggcggtgct
acagagttcttgaagtggtggcctaactacggctacactagaagg
acagtatttggtatctgcgctctgctgaagccagttaccttcggaaa
aagagttggtagctcttgatccggcaaacaaaccaccgctggt
agcggtggtttttttgtttgcaagcagcagattacgcgcagaaaaaa
aggatctcaagaagatcctttgatctttctacggggtctgacgctcagtggaacgaaaactcacgttaagggattttggtcatgagatta
tcaaaaaggatcttcacctagatcctttttaaaggccggccgc
ggccgccatcggcatttctttttgcgttttttattgttaactgttaa
ttgtcctgttcaaggatgctgtctttgacaacagatgttttcttgc
ctttgatgttcagcaggaagctcggcgcaaacgttgattgtttgtct gcgtagaatcctctgtttgtcatatagcttgtaatcacgacattgtt
tcctttcgcttgaggtacagcgaagtgtgagtaagtaaaggttacat
cgttaggatcaagatccattttttaacacaaggccagttttgttcagc
ggcttgtatgggcagttaaagaattagaaacataaccaagcatgta
aatatcgttagacgtaatgccgtcaatcgtcattttttgatccgcggga
gtcagtgaacaggtaccatttgccgttcattttaaagacgttcgcgcgt
tcaatttcatctgttactgtgttagatgcaatcagcggtttcatc
actttttttcagtgtgtaatcatcgtttagctcaatcataccgagagc
gccgtttgctaactcagccgtgcgttttttatcgctttgcagaagttttt
gactttcttgacggaagaatgatgtgcttttgccatagtatgctttg
ttaaataaagattcttcgccttggtagccatcttcagttccagtgtttg
cttcaaattactaagtatttgtggccttatcttctacgtagtgagga
tctctcagcgtatggttgtcgcctgagctgtagttgcctcatcgatg
aactgctgtacattttgatacgttttttccgtcaccgtcaaagattga
tttataatcctctacaccgttgatgttcaaagagctgtctgatgctga
tacgttaacttgtgcagttgcatgttgttttttgccgtaatgtttac
cggagaaatcagtgtagaataaaacggattttttccgtcagatgtaaat
gtggctgaacctgaccattcttgtgtttggtcttttaggatagaatca
tttgcatcgaatttgtcgctgtctttaaagacgcggccagcgtttttc
cagctgtcaaacagggtttcgccgacttttgatagaacatgtaaatc
gatgtgtcatccgcattttaggatctccggctaatgcaaagacgatg
tggtagccgtgatagtttgcgacagtgccgtcagcgttttgtaatggc
cagctgtcccaaacgtccaggccttttgcagaagagatatttttaat
tgtggacgaatcaaattcagaaacttgatattttttcatttttttgctg
ttcaggggatttgcagcatatcatggcgtgtaatatgggaaatgccgta
tgtttcctatatggcttttggttcgtttctttcgcaaacgcttgag
ttgcgcctcctgccagcagtgcggtagtaaaggttaatactgttgctt
gtttttgcaaactttttgatgttcatcgttcatgtctcctttttatg
tactgtgttagcggtctgcttcttccagccctcctgtttgaagatgg
caagttagttacgcacaataaaaaaaagaacctaaaatatgtaaggggtg
acgccaaagtatacactttgccctttacacattttaggtcttgcctgc
tttatcagtaaaacccgcgcgaattacttttcgacctcattctatt
agactctcgttggattgcaactggtctatttcctcctttgttt
gatagaaaatcataaaaggatttgcagactacgggcctaaagaactaa
aaaatctatctgttctttcattctctgtatttttatagtttctgt
tgcatgggcataaagttgcctttttaatcacaattcagaaaatatcat
aatatctcatttcactaaataatagtgaacggcagctatatgtg
atgggttaaaaaggatcggcggccgctcgatttaaatc SEQ ID NO: 11 (complete nucleotide sequence of plasmid pSacB_delta_pflA)
tcgagtcaatgcggatttgacttatgatgtggcaaacaaccgatttcc
gattattactacacgtaaaagttattggaaagcggcggattgcg
gagtttctgggttatatccgcggctacgataatgcggcggatttc
cgtaaattaggagcaaaaacctgggatgccaacgctaatgcaaa
atcaggtatggctgaataaccctcatcgcaaaggcaccgacgacat
ggggcgcgtttacggcgtacagggcagagcctggcgtaa
gcctaacggcgaaaccgttgatcaattaccgcaaaattgtcaacaat
ttaagtcgcggcattgatgatcgcggcgaaattctgaccttttt
aaacccggcgaatttcgatctcggttgtctgcgcccttgtatgtac
aatcacacgttttctttgctgggcgatacgctttatttaaccagtt
atcaacgctcctgtgacgtacctttaggcttgaatttcaatcaaa
ttcaagtatttacattcttagctttaatggcgcagattaccggtaa
aaaagccggtcaggcatatcacaaaatcgtcaatgcgcatatttac
gaagaccagctggaactaatgcgcgacgtgcagttaaaacgcga
accgttcccgtcgccaaaactggaaattaatccggacattaaaacc
cttgaagatttgaaaaacctgggtaaccatggatgatttcaacg
tcgttggttaccaatgccacgaaccgataaaatatccgttctcgg
tataaaccgacaaaagtgcggtcaaaaatttaatattttcatctgtt
atagaaaatattttcaacataaaatctagggatgcctgtttggcg
tccgtaaatacgcagaaaaatattaaattttgaccgcacttttt
catctcaattaacagcctgataattcttatggatcaacaaattagct
ttgacgaaaaatgatgaatcgagctctttttccttgccgacaagg
cggaagctttaggggaaatttcccgtaggtgccgtattggtggatga
acggggcaatatcattggtgaaggctggaacctctctattgtg
aactcggatcccaccgcccatgccgaaattattgcgttgcgtaacg
ccgcgcagaaaatccaaaattaccgcctgctcaataccacttata
cgtgactttagaacccctgcaccatgtgcgccggcgcgatttacaca
gccgaatcaaaacgcttggtattcggggcgtccgattacaaaaccggtg
cggtgggttccagatttcatttttttgaggattataaaatgaatcatg
gggttgagatcacaagcggtgtcttacaggatcaatgcagtcagaagt
taagccgctttttcaacagaccgcagggaacagaaaaaacaacaaaag
ctaccgcacttttacaacaccccccggcttaacttcctctgaaaaatagtg
acaaaaaaaccgtcataatgtttacgacggttttttttatttcttaata
tgccctaaataatcaacaaaatatagcaagaagattatagcaaagaa
tttcgttttttcagagaatagtcaaatcttcgcaaaaaactaccgcac
ttttatccgctttaatcaggggaattaaaacaaaaaaattccgcctat

```
tgaggcggaatttattaagcaataagacaaactctcaattacattgat
tgtgtaaacgtacgagtgatgacgtcttgttgttgctctttagttaa
tgagttgaaacgaaccgcgtaacctgaaacacgaatggttaattgcggt
attttttccggattttccatcgcgtctaacaacatttcacggttaagaa
cgttaacattcaagtgttgaccgccttccactgtcgcttcatgatg
gaaataaccgtccattaaaccggcaaggttgcgtttttgcgcttcgtc
atctttacctaatgcgttcggtacgatagagaaggtatatgaaatacc
gtctttcgcgtaagcgaacggaagtttagccacagaagtaagtgaagc
aaccgcacctttttggtcacgaccgtgcattgggtttgcacccggtcc
gaatggcgcgcctgctcgacgaccgtccggagtattaccggttttctt
accgtataccacgttagaagtgatagtcaggatagattgtgtcggag
ttgcgttgcggtaagttttgtgttttttgaacttttttcatgaaacgt
tcaactaagtctaccgctaaatcatcaacacgcggatcattgttacc
gaattgcggatattcgcctcaatttcgaagtcgatagcaacattcg
aggccacgacattaccgtctttatctttgatgtcgccgcgaatcggt
ttaactttcgcatatttgattgcggataatgagtccgcagccacgga
aagaccgcgataccgcaagccattgtacggaatacgtcgcgatcgtgg
aacgccatcaatgccgcttcatatgcatatttatcgtgcatgaagtgg
atgatgttcaatgcggttacatattgagtcgccaaccagtccatgaaac
tgtccatacgttcgattacggtatcgaaattcaatacttcgtctgtaat
cggcgcagttttaggaccgacttgcataccatttttctcatcgatacc
gccgttaattgcgtataacatagttttagctaagtttgcgcgcgcacc
gaagaattgcatttgtttacctacgaccatcggtgatacgcagcatgcg
attgcatagtcatcgttgttgaagtcaggacgcattaagtcatcattttc
gtattgtacggaggaagtatcaatagatactttcgcacagaaacgtttga
acgcttcaggtaattgttcggaccaaagaatagttaagtttggt
tccgagaagtacccatagtgtataaagtatgtaatacgcggaagctctt
tagttaccaacggacgaccgtctaagccatacccggcgatagtttcggtt
gccctctagactccataggccgctttcctggctttgcttccagatgta
tgctctcctccggagagtaccgtgactttattttcggcacaaatacagg
ggtcgatggataaatacggcgatagttcctgacggatgatccgtatgt
accggcggaagacaagctgcaaacctgtcagtggagagttgatttaatg
gcggatgtgctgagagcaccgccccgtgaatccgcagaactgatccgt
atgtgtttgcggatgattggccggaataaataaagcgggcttaatac
agattaagcccgtataggtattattactgaataccaaacagcttac
ggaggacggaatgttaccccattgagacaaccagactgccttctgatt
attaatattttttcactattaatcagaaggaataaccatgaactttacc
cggattgacctgaatacctggaatcgcagggaacactttgccctttt
atcgtcagcagattaaatgcggattcagcctgaccaccaaactcgata
ttaccgctttgcgtaccgcactggcggagacaggttataagttttatc
cgctgatgatttacctgatctcccgggctgttaatcagtttccgg
agttccggatggcactgaaagacaatgaacttattttactgggaccag
tcagaccccggtctttactgtctttcataaagaaaccgaaacattctc
tgcactgtcctgccgttattttccggatctcagtgagtttatggcag
gttataatgcggtaacggacgaaatatcagcatgatacgtagttgtttc
cgcagggaaatttaccggagaatcacctgaatatatcatcattaccgt
gggtgagttttgacgggatttaacctgaacatcaccggaaatgatgatt
attttgccccgOttttacgatggcaaagtttcagcaggaaggtgaccgc
gtattattacctgtttctgtacaggttcatcatgcagtcgtgatgtgt
tttcatgcagcacggttttattaatacacttcagctgatgtgtgataac
atactgaaataaattaattaattctgtatttaagccaccgtatccggc
aggaatggtggcttttttttatatttaaccgtaatctgtaatttc
gtttcagactggttcaggatgagctcgcttggactcctgttgataga
tccagtaatgacctcagaactccatctggatttgttcagaacgctcg
gttgccgccgggcgtttttattggtgagaatccaagcactagcggcg
cgccggccgcccggtgtgaaataccgcacagatgcgtaaggagaaaa
taccgcatcaggcgctcttccgcttcctcgctcactgactcgctgcgc
tcggtcgttcggctgcggcgagcggtatcagctcactcaaaggcggt
aatacggttatccacagaatcaggggataacgcaggaaagaacatgt
gagcaaaaggccagcaaaaggccaggaaccgtaaaaaggccgcgtt
gctggcgtttttccataggctccgcccccctgacgagcatcacaaaa
atcgacgctcaagtcagaggtggcgaaacccgacaggactataaaga
taccaggcgtttccccctggaagctccctcgtgcgctctcctgttcc
gaccctgccgcttaccggatacctgtccgcctttctcccttcggga
agcgtggcgctttctcatagctcacgctgtaggtatctcagttcggt
gtaggtcgttcgctccaagctgggctgtgtgcacgaaccccccgtt
cagcccgaccgctgcgccttatccggtaactatcgtcttgagtccaa
cccggtaagacacgacttatcgccactggcagcagccactggtaaca
ggattagcagagcgaggtatgtaggcggtgctacagagttcttgaag
tggtggcctaactacggctacactagaaggacagtatttggtatctg
cgctctgctgaagccagttaccttcggaaaaagagttggtagctctt
gatccggcaaacaaaccaccgctggtagcggtggtttttttgtttgca
agcagcagattacgcgcagaaaaaaaggatctcaagaagatcctttg
atcttttctacggggtctgacgctcagtggaacgaaaactcacgttaa
gggattttggtcatgagattatcaaaaaggatcttcacctagatcct
tttaaaggccgccgcggccgccatcggcattttcttttgcgttttt
atttgttaactgttaattgtcctgttcaaggatgctgtcttgacaa
```
```
cagatgttttcttgcctttgatgttcagcaggaagctcggcgcaaacg
ttgattgtttgtctgcgtagaatcctctgtttgtcatatagcttgta
atcacgacattgttttccttttcgcttgaggtacagcgaagtgtgagtaa
gtaaaggttacatcgttaggatcaagatccattttttaacacaaggcca
gttttgttcagcggcttgtatgggccagttaaagaattagaaacataa
gatccgcgggagtcagtgaacaggtaccattttgccgttcatttttaaag
acgttcgcgcgttcaatttcatctgttactgtgttagatgcaatcagc
ggttttcatcacttttttcagtgtgtaatcatcgtttagctcaatcata
ccgagagcgccgtttgctaactcagccgtgcgttttttatcgctttgca
gaagtttttgacttttctgacggaagaatgatgtgcttttgccatagt
atgctttgttaaataaagattcttcgccttggtagccatcttcagttcc
agtgtttgcttcaaatactaagtatttgtggcctttatcttctacgta
gtgaggatctctcagcgtatggttgtcgcctgagctgtagttgccttc
atcgatgaactgctgtacattttgatacgttttttccgtcaccgtcaaag
attgatttataatcctctacaccgttgatgttcaaagagctgctg
atgctgatacgttaacttgtgcagttgtcagtgtttgtttgccgtaat
gtttaccggagaaatcagtgtagaataaaacggattttttccgtcaga
tgtaaatgtggctgaacctgaccattcttgtgtttggtcttttaggat
agaatcatttgcatcgaatttgtgctgtctttaaagacgcggcgcag
cgttttttccagctgtcaatagaagttttcgccgactttttgatagaaca
tgtaaatcgatgtgtcatccgcatttttaggatctccggctaatgc
aaagacgatgtggtagccgtgatagtttgcgacagtgccgtcagcgtt
ttgtaatggccagctgtcccaaacgtccaggcctttttgcaga
agagatatttttaattgtgacgaatcaaattcagaaacttgatatttt
tcattttttttgctgttcagggatttgcagcatatcatggcgtgtaata
tgggaaatgccgtatgttttcctttatgcttttggttcgtttcttc
gcaaacgcttgagttgcgctcctgccagcagtgcggtagtaaagg
ttaatactgttgcttgttttgcaaacttttttgatgttcatcgttcatg
tctccttttttatgtactgtgttagcggtctgcttcttccagccctcc
tgtttgaagatggcaagttagttacgcacaataaaaaaagacctaaaa
tatgtaaggggtgacgccaaagtatacactttgccctttacacatttt
aggtcttgcctgcttttatcagtaacaaacccgcgcgatttactttcg
acctcattctattagactctcgtttggattgcaactggtctatttctct
cttttgtttgatagaaaatcataaaaggatttgcagactacgggcct
aaagaactaaaaatctatctgttttcttttcattctctgtattttttata
gtttctgttgcatgggcataaagttgcctttttaatcacaattcagaaa
atatcataatatctcatttcactaaataatagtgaacggcaggt
atatgtgatgggttaaaaaggatcggcggccgctcgatttaaatc SEQ ID NO: 12 (complete nucleotide sequence of
plasmid pSacB_delta_pflD)
tcgagaggcctgacgtcgggcccggtaccacgcgtcatatgactagttc
ggacctagggatgggatcgagctcttttccttgccgaca
aggcggaagctttagggggaaaatccgtaggtgccgtattggtggat
gaacggggcaatatcattggtgaaggctggaacctctctatt
gtgaactcggatcccaccgccatgccgaaattattgcgttgcgtaa
cgccgcgcagaaaatccaaaattaccgcctgctcaatacc
acttatacgtgactttagaacctgcaccatgtgcgccgcgcgat
tttacacagccgaatcaaacgcttggtattcgggggcgtccgat
tacaaaaccggtgcggtgggttccagatttcatttttttgaggatta
taaaatgaatcatgggttgagatcacaagcggtgtcttataggca
tcaatgcagtcaggagttaagccgcttttccaaaagcgcagggaac
agaaaaaacaacaaaaagctaccgcacttttacaacacc
cccggcttaactcctctgaaaaatagtgacaaaaaaaccgtcataat
gtttacgacgcttttttatttcttctaatatgtcacattaagcccg
tagcctgcaagcaaccccttaacatgctccattaattctttttgtc
ggcggtttacatcttcaagctcgtatttatcgccgagtcacttccat
ttatgggcgcctagacggtgataaggtaataattccacttttttcga
tattcttcatatctttaatgaaattcccccagcatgtgcaaatcttcg
tcactatctgtataaccggcactacaacatggcggatccaggtacg
ctgatttcgatccgctaaatattttgcgaattcgagcactctttat
tcggcacgccaatcaggctttcgtgaacccgttcattcatttctttc
aggtcaagcaacacaagatccgtgtcatcaatcaattcatcaataat
atgatcatgatgacggacgaaaccgttggatccaagcaagtatt
aattccttcttttatggcaggctctgaaccagtcccgtacaaattcc
gcctgtaaatagctcaccgccggaagcgtaactccgcccgccgag
gcgttcataaaatggcgataggtcaccacttctttcattaa
ttcttcaacggaaatttctttaccgccgtgcaaatcccaggtgtctc
tgttatggcaatatttacaacgcattaagcagccttgtaaaaataa
aataaagcggttcccggcccgtcaactcccgcaggtttcaaatg
aatgaattcgtctaaaaccgacataatatgccctaaataa
tcaacaaaatatagcaagaagattatagcaaagaattttcgttttttt
cagagaatagtcaaatcttgcaaaaaactaccgcacttttatc
cgctttaatcaggggaattaaaacaaaaaaattccgcctattgaggc
ggaattattaagcaataagacaaactctcaattttaatacttc
cttcttttctagtattgataagattgaaaccttgcaaggatgacgg
```

```
cggatttgccgtcactctcacccaactaatgtggacgactggtaa
accattgcattagaccaatgcaaacaccaccaccgacgatgttacct
aaagtaacaggaattaaatttttaattactaaatggtacatat
ctaaatttgcaaactgctcggcatttaaaccccgttgcctgccagaat
tccggcgatgcgaaatttgcaattaccatgcccataggatca
taaacatatttgctacgcagtgttcaaagcctgaagcgacaaayaac
ccgatcggcaggatcataataaaagctttatccgttagagt
yttgccggcataggccatccaaacggcaatacataccataatgttg
caaagaatacctaaacagaaggcttcaayccaggtatgttct
attttatgttgtgccgtatttaaaatggttaatcccactgaccgt
ttgccgccatgatctgaccggaaaaccaaattaatgcaacaataa
ataaaccgccgacaaaattaccgaartaaaccacaatccagttacg
taacatctgaattgttgtaattttactctcaaagcgggcaata
gtcgataaagttgatgaagtaaatagttcacagccgcaaaccgcca
ccataattaccccgagagagaacaccaaaccgccgacc
agtttagttaatccccaaggcgctcccgcagaggctgtttgagttgt
tgtataaaaaacgaatgcaagagcaataaacataccggcag
agatcgccgataaaaatgaataggcttgttttttcgtagcttat
aaacgccgacgtctaacccggtttgagccatctcggttggcgaagc
catccaagccaatttaaaatcttccgatttcattgagctttcctta
gtaataaaactactcggaaatgagtagaactgccttaaagcataa
atgatagattaaaaaatccaaaattgttgaatattatttaacgggg
ggattataaaagattcataaattagataatagctaatttgagtgat
ccatatcaccttttacagattttttgacctaaatcaaaattacccaa
atagagtaataataccattataaaggggtggatttattccttttggttt
acgagataaaattgctatttaagctgatttctgataaaaagtgcggt
agattttttcccaaaaataaggaaacacaaaatggcagaagaa
acaatttcagtaaaattattcgtaaagaaattcccgccagcattat
atatcaagacgatcttgtcaccgcatttcgcgatattgcgccgca
ggcaaaaactcatattttaattattccgaataaattgattccgacag
taaacgacgtaaccgcccatcgtcgacatcgatgctcttctgcg
ttaattaacaattgggatcctctagactttgcttccagatgatgctc
tcctccggagagtcgtgactttattttcggcacaaatacaggg
gtcgatggataccgtgacgatagtttcctgacggatgatccgtatgt
accggcggaagacaagctgcaaacctgtcagatggagatt
gatttaatggcggatgtgctgagagcaccgccccgtgaatccgcagaa
ctgatccgctatgtgtttgccggatgattggccggacact
aaagccgggcttaatacagattaagccgtataggtattattactga
ataccaaacagcttacggaggacggaatgttacccattga
gacaaccagactgccttctgattattaatattttcactattaatcag
aaggaataaccatgaattttacccggattgacctgaatacctgg
aatcgcagggaacactttgcccttatcgtcagcagattaaatgcgga
ttcagcctgaccaccaaactcgatattaccgcttgcgtacc
gcactggcggagacaggttataagttttatccgctgatgatttacctg
atctcccgggctgttaatcagtttccggagttccggatggacct
gaaagacaatgaacttatttactgggaccagtcagacccggtctttac
tgtcttttcataaagaaaccgaaacattctctgcactgtcctgc
cgttattttccggatctcagtgagtttatggcaggttataatgcggta
acggcagaatatcagcatgataccagattgtttcgctgccgcggaa
atttaccggagaatcacctgaatatatcatcattaccgtgggtgagtt
ttgacgggatttaacctgaacatcaccggaaatgatgattatttt
gccccggttttacgatggcaaagtttcagcaggaaggtgaccgcgta
ttattacctgtttctgtacagttcatcatgcagtctgtgatgg
ctttcatgcagcacggtttattaatacacttcagctgatgtgtgataa
catactgaaataaattaattaattctgtatttaagcaccgtatcc
ggcaggaatggtggctttttttttatattttaaccgtaatctgtaatt
tcgtttcagactggttcaggatgagctcgcttggactcctgttagag
atccagtaatgacctcagaactccatctggatttgttcagaacgctcg
gttgccgccgggcgttttttattggtgagaatccaagcactag
cggcgcgccggccgcccggtgtgaaataccgcacagatgcgtaagga
gaaaataccgcatcaggcgctcttccgcttcctcgctc
```

```
actgactcgctgcgctcggtcgttcggctgcggcgagcggtatcagct
cactcaaaggcggtaatacggttatccacagaatcaggg
gataacgcaggaaagaacatgtgagcaaaaggccagcaaaaggccagg
aaccgtaaaaaggccgcgttgctggcgtttttccat
aggctccgcccccctgacgagcatcacaaaaatcgacgctcaagtca
gaggtggcgaaacccgacaggactataaagataccaggcgtttcccc
ctgaaagctccctcgtgcgctctcctgttccgaccctgccgcttaccg
gatacctgtccgcctttctcccttcgggaagcgtggcgctttctcata
gctcacgctgtaggtatctcagttcggtgtaggtcgttcgctccaagc
tgggctgtgtgcacgaaccccccgttcagcccgaccgctgcgcttat
ccggtaactatcgtcttgagtccaacccggtaagacacgacttatcg
ccactggcagcagccactggtaacaggattagcagagcgaggtatgt
aggcggtgctacagagttcttgaagtggtggcctaactacggctaca
ctagaaggacagtatttggtatctgcgctctgctgaagccagttac
cttcggaaaaagagttggtagctcttgatccggcaaacaaaccaccg
ctggtagcggtggtttttttgtttgcaagcagcagattacgcgcaga
aaaaaaggatctcaagaagatcctttgatctttctacggggtctga
cgctcagtggaacgaaaactcacgttaagggattttggtcatgaga
ttatcaaaaaggatcttcacctagatccttttaaaggccggcgcgg
ccgccatcggcattttcttttgcgttttttatttgttaactgttaattg
tccttgttcaaggatgctgtctttgacaacagatgttttcttgccttt
gatgttcagcaggaagctcggcgcaaacgttgattgtttgtctgcgta
gaatcctctgtttgtcatatagcttgtaatcacgacattgtttcctt
cgcttgaggtacagcgaagtgtgagtaagtaaaggttacatcgttag
gatcaagatccattttaacacaaggccagttttgttcagcggcttgt
atgggccagttaaagaattagaaacataaccaagcatgtaaatatcgtt
agacgtaatgccgtcaatcgtcatttttgatccgcgggagtcagtg
aacaggtaccatttgccgttcattttaaagacgttcgcgcgttcaat
ttcatctgttactgtgttagatgcaatcagcggttcatcacttttttc
agtgtgtaatcatcgtttagctcaatcataccgagagcgccgtttgcta
actcagccgtgcgtttttatcgctttgcagaagttttttgactttcttg
acggaagaatgatgtgctttgccatagtagctttgttaaataaagat
tcttcgccttggtagccatcttcagttccagtgtttgcttcaaata
ctaagtattgtgtgccttatcttctacgtagtgaggatctctcagcgt
atggttgtcgcctgagctgtagttgccttcatcgatgaactgctgt
acattttgatacgtttttccgtcaccgtcaaagattgatttataatcct
ctacaccgttgatgttcaaagagctgtctgatgctgatacgttaac
ttgtgcagttgtcagtgttttgtttgccgtaatgtttaccggagaaatca
gtgtagaataaacggattttttccgtcagatgtaaatgtggctgaa
cctgaccattcttgtgtttggtcttttaggatagaatcatttgcatcga
atttgtcgctgtcttaaagacgcggccagcgttttccagctgtca
ataagaagtttcgccgacttttttgatagaacatgtaaatcgatgtgtcat
ccgcattttaggatctccggctaatgcaaagacgatgtggta
gccgtgatagtttgcgacagtgccgtcagcgttttgtaatggccagctgt
cccaaacgtccaggcctttgcagaagagatatttttaattg
tggacgaatcaaattcagaaacttgatatttttcatttttttgctgttc
agggatttgcagcatatcatggcgtgtaatatgggaaatgccgtat
gttccttatatggcttttggttcgtttcttcgcaaacgcttgagt
tgcgcctcctgccagcagtgcggtagtaaaggttaatactgttgcttgtt
ttgcaaacttttttgatgttcatcgttcatgtctccttttttatgtactg
tgttagcggtctgcttcttccagccctcctgttgaagatggcaagttagt
tacgcacaataaaaaaagacctaaatatgtaaggggtgacgccaaagt
atacactttgcccttacacattttaggtcttgcctgcttta
tcagtaacaaaccgcgcgattactttcgacctcattctattagact
ctcgtttggattgcaactggtctattttcctcttttgtttgatagaaa
atcataaaggatttgcagactacgggcctaaagaactaaaaaatctatc
tgtttcttttcattctctgtattttttatagttttcgtttgcatgggc
ataaagttgcctttttaatcacaattcagaaaatatcataatctcat
ttcactaaataatagtgaacggcaggtatatgtgatgggttaaa
aaggatcggcggccgctcgatttaaatc
```

The invention claimed is:

1. A process for producing an organic acid by fermentation, comprising the process steps:
I) cultivating a modified microorganism in a culture medium to which is fed, as assimilable carbon sources, glycerol and a further carbonaceous compound, to allow the microorganism to produce the organic acid, thereby obtaining a fermentation broth comprising the organic acid;
II) recovering the organic acid or the salt thereof from the fermentation broth obtained in process step I);
wherein further carbonaceous compound is fed to the culture medium such that the consumption rate of the further carbonaceous compound ($CR_{c.c.}$; in g per liter per hour) is lower than the maximum theoretical consumption rate of the further carbonaceous compound ($CR_{c.c.\ max}$; in g per liter per hour),
wherein the organic acid is succinic acid,
wherein the further carbonaceous compound is a carbohydrate, and
wherein the wildtype from which the modified microorganism has been derived belongs to the family of Pasteurellaceae,
wherein the modified microorganism has, compared to its wildtype,
i) a reduced pyruvate formate lyase activity,
ii) a reduced lactate dehydrogenase activity, or
iii) a reduced pyruvate formate lyase activity and a reduced lactate dehydrogenase activity, and
wherein the modified microorganism comprises:
A) a deletion of the ldhA-gene or at least a part thereof, a deletion of a regulatory element of the ldhA-gene or at least a part thereof or an introduction of at least one mutation into the ldhA-gene;
B) a deletion of the pflD-gene or at least a part thereof, a deletion of a regulatory element of the pflD-gene or at least a part thereof or an introduction of at least one mutation into the pflD-gene;
C) a deletion of the pflA-gene or at least a part thereof, a deletion of a regulatory element of the pflA-gene or at least a part thereof or an introduction of at least one mutation into the pflA-gene;
D) a deletion of the ldhA-gene or at least a part thereof, a deletion of a regulatory element of the ldhA-gene or at least a part thereof or an introduction of at least one mutation into the ldhA-gene
and
a deletion of the pflD-gene or at least a part thereof, a deletion of a regulatory element of the pflD-gene or at least a part thereof or an introduction of at least one mutation into the pflD-gene;
or
E) a deletion of the ldhA-gene or at least a part thereof, a deletion of a regulatory element of the ldhA-gene or at least a part thereof or an introduction of at least one mutation into the ldhA-gene
and
a deletion of the pflA-gene or at least a part thereof, a deletion of a regulatory element of the pflA-gene or at least a part thereof or an introduction of at least one mutation into the pflA-gene.

2. The process according to claim 1, wherein for a cultivation period of at least 30 minutes the consumption rate of the further carbonaceous compound ($CR_{c.c.}$; in g per liter per hour) is lower than the maximum theoretical consumption rate of the further carbonaceous compound ($CR_{c.c.\ max}$; in g per liter per hour).

3. The process according to claim 1, wherein the consumption rate of the further carbonaceous compound ($CR_{c.c.}$; in g per liter per hour) is not more than 50% of the maximum theoretical consumption rate of the further carbonaceous compound ($CR_{c.c.\ max}$; in g per liter per hour).

4. The process according to claim 1, wherein in process step I) glycerol and the further carbonaceous compound are fed into the culture medium in a total weight ratio glycerol: further carbonaceous compound of at least 5:1.

5. The process according to claim 1, wherein the carbohydrate is selected from the group consisting of sucrose, D-glucose or mixtures thereof.

6. The process according to claim 1, wherein the wildtype from which the modified microorganism has been derived belongs to the genus *Basfia*.

7. The process according to claim 6, wherein the microorganism used in process step I) belongs to the species *Basfia succiniciproducens*.

8. The process according to claim 7, wherein the wildtype from which the modified microorganism has been derived has a 16S rDNA of SEQ ID NO: 1 or a sequence, which shows a sequence homology of at least 96% with SEQ ID NO: 1.

9. The process according to claim 1, wherein the process further comprises the process step:
   III) converting the organic acid contained in the fermentation broth obtained in process step I) or converting the recovered organic acid obtained in process step II) into a secondary organic product being different from the organic acid by at least one chemical reaction.

10. The process according to claim 9, wherein the organic acid is succinic acid and wherein the secondary organic product is selected from the group consisting of succinic acid esters or polymers thereof, tetrahydrofuran (THF), 1,4-butanediol (BDO), gamma-butyrolactone (GBL) and pyrrolidones.

* * * * *

SEQUENCE LISTING

<160> NUMBER OF SEQ ID NOS: 12

<210> SEQ ID NO 1
<211> LENGTH: 1517
<212> TYPE: DNA
<213> ORGANISM: Basfia succiniciproducens
<220> FEATURE:
<221> NAME/KEY: misc_feature
<222> LOCATION: (1)..(1517)
<223> OTHER INFORMATION: 16 S rDNA of strain DD1

<400> SEQUENCE: 1

```
tttgatcctg gctcagattg aacgctggcg gcaggcttaa cacatgcaag tcgaacggta    60
gcgggaggaa agcttgcttt ctttgccgac gagtggcgga cgggtgagta atgcttgggg   120
atctggctta tggaggggga taacgacggg aaactgtcgc taataccgcg taatatcttc   180
ggattaaagg gtgggacttt cgggccaccc gccataagat gagcccaagt gggattaggt   240
agttggtggg gtaaaggcct accaagccga cgatctctag ctggtctgag aggatgacca   300
gccacactgg aactgagaca cggtccagac tcctacggga ggcagcagtg gggaatattg   360
cacaatgggg ggaaccctga tgcagccatg ccgcgtgaat gaagaaggcc ttcgggttgt   420
aaagttcttt cggtgacgag gaaggtgttt gttttaatag acaagcaat tgacgttaat    480
cacagaagaa gcaccggcta actccgtgcc agcagccgcg gtaatacgga gggtgcgagc   540
gttaatcgga ataactgggc gtaaagggca tgcaggcgga cttttaagtg agatgtgaaa   600
gccccgggct taacctggga attgcatttc agactgggag tctagagtac tttagggagg   660
ggtagaattc cacgtgtagc ggtgaaatgc gtagagatgt ggaggaatac cgaaggcgaa   720
ggcagcccct tgggaagata ctgacgctca tatgcgaaag cgtggggagc aaacaggatt   780
agatacccctg gtagtccacg cggtaaacgc tgtcgatttg gggattgggc tttaggcctg   840
gtgctcgtag ctaacgtgat aaatcgaccc cctggggagt acggccgcaa ggttaaaact   900
caaatgaatt gacgggggcc cgcacaagcg gtggagcatg tggtttaatt cgatgcaacg   960
cgaagaacct tacctactct tgacatccag agaatcctgt agagatacgg gagtgccttc  1020
gggagctctg agacaggtgc tgcatggctg tcgtcagctc gtgttgtgaa atgttgggtt  1080
aagtcccgca acgagcgcaa cccttatcct ttgttgccag catgtaaaga tgggaactca  1140
aaggagactg ccggtgacaa accggaggaa ggtgggggatg acgtcaagtc atcatggccc  1200
ttacgagtag ggctacacac gtgctacaat ggtgcataca gagggcggcg ataccgcgag  1260
gtagagcgaa tctcagaaag tgcatcgtag tccggattgg agtctgcaac tcgactccat  1320
gaagtcggaa tcgctagtaa tcgcaaatca gaatgttgcg gtgaatacgt tcccgggcct  1380
tgtacacacc gcccgtcaca ccatgggagt gggttgtacc agaagtagat agcttaacct  1440
tcggggggg cgtttaccac ggtatgattc atgactgggg tgaagtcgta acaaggtaac  1500
cgtagggaa cctgcgg                                                   1517
```

<210> SEQ ID NO 2
<211> LENGTH: 3008
<212> TYPE: DNA
<213> ORGANISM: Basfia succiniciproducens
<220> FEATURE:
<221> NAME/KEY: misc_feature
<222> LOCATION: (1)..(3008)
<223> OTHER INFORMATION: 23 S rDNA of strain DD1

<400> SEQUENCE: 2

```
agtaataacg aacgacacag gtataagaat acttgaggtt gtatggttaa gtgactaagc    60
gtacaaggtg gatgccttgg caatcagagg cgaagaagga cgtgctaatc tgcgaaaagc   120
ttgggtgagt tgataagaag cgtctaaccc aagatatccg aatggggcaa cccagtagat   180
gaagaatcta ctatcaataa ccgaatccat aggttattga ggcaaaccgg gagaactgaa   240
acatctaagt accccgagga aaagaaatca accgagatta cgtcagtagc ggcgagcgaa   300
agcgtaagag ccggcaagtg atagcatgag gattagagga atcggctggg aagccgggcg   360
```

```
gcacagggtg atagccccgt acttgaaaat cattgtgtgg tactgagctt gcgagaagta    420
gggcgggaca cgagaaatcc tgtttgaaga agggggggacc atcctccaag gctaaatact    480
cctgattgac cgatagtgaa ccagtactgt gaaggaaagg cgaaaagaac cccggtgagg    540
ggagtgaaat agaacctgaa accttgtacg tacaagcagt gggagcccgc gagggtgact    600
gcgtaccttt tgtataatgg gtcagcgact tatattatgt agcgaggtta accgaatagg    660
ggagccgaag ggaaaccgag tcttaactgg gcgtcgagtt gcatgatata gacccgaaac    720
ccggtgatct agccatgggc aggttgaagg ttgggtaaca ctaactggag gaccgaaccg    780
actaatgttg aaaaattagc ggatgacctg tggctggggg tgaaaggcca atcaaaccgg    840
gagatagctg gttctccccg aaatctattt aggtagagcc ttatgtgaat accttcgggg    900
gtagagcact gtttcggcta gggggccatc ccggcttacc aacccgatgc aaactgcgaa    960
taccgaagag taatgcatag gagacacacg gcgggtgcta acgttcgtcg tggagaggga   1020
aacaacccag accgccagct aaggtcccaa agtttatatt aagtgggaaa cgaagtggga   1080
aggcttagac agctaggatg ttggcttaga agcagccatc atttaaagaa agcgtaatag   1140
ctcactagtc gagtcggcct gcgcggaaga tgtaacgggg ctcaaatata gcaccgaagc   1200
tgcggcatca ggcgtaagcc tgttgggtag gggagcgtcg tgtaagcgga agaaggtggt   1260
tcgagagggc tgctggacgt atcacgagtg cgaatgctga cataagtaac gataaaacgg   1320
gtgaaaaacc cgttcgccgg aagaccaagg gttcctgtcc aacgttaatc ggggcagggt   1380
gagtcggccc ctaaggcgag gctgaagagc gtagtcgatg ggaaacgggt taatattccc   1440
gtacttgtta taattgcgat gtggggacgg agtaggttag gttatcgacc tgttggaaaa   1500
ggtcgtttaa gttggtaggt ggagcgttta ggcaaatccg gacgcttatc aacaccgaga   1560
gatgatgacg aggcgctaag gtgccgaagt aaccgatacc acacttccag gaaaagccac   1620
taagcgtcag attataataa accgtactat aaaccgacac aggtggtcag gtagagaata   1680
ctcaggcgct tgagagaact cgggtgaagg aactaggcaa aatagcaccg taacttcggg   1740
agaaggtgcg ccggcgtaga ttgtagaggt ataccttga aggttgaacc ggtcgaagtg   1800
acccgctggc tgcaactgtt tattaaaaac acagcactct gcaaacacga aagtggacgt   1860
atagggtgtg atgcctgccc ggtgctggaa ggttaattga tggcgttatc gcaagagaag   1920
cgcctgatcg aagccccagt aaacggcggc cgtaactata acggtcctaa ggtagcgaaa   1980
ttccttgtcg ggtaagttcc gacctgcacg aatggcataa tgatggccag gctgtctcca   2040
cccgagactc agtgaaattg aaatcgccgt gaagatgcgg tgtacccgcg gctagacgga   2100
aagaccccgt gaacctttac tatagcttga cactgaacct tgaattttga tgtgtaggat   2160
aggtgggagg ctttgaagcg gtaacgccag ttatcgtgga gccatccttg aaataccacc   2220
ctttaacgtt tgatgttcta acgaagtgcc cggaacgggt actcggacag tgtctggtgg   2280
gtagtttgac tggggcggtc tcctcccaaa gagtaacgga ggagcacgaa ggttgctaa   2340 tgacggtcgg acatcgtcag gttagtgcaa tggtataagc aagcttaact gcgagacgga   2400
caagtcgagc aggtgcgaaa gcaggtcata gtgatccggt ggttctgaat ggaagggcca   2460
tcgctcaacg gataaaaggt actccgggga taacaggctg ataccgccca agagttcata   2520
tcgacggcgg tgtttggcac ctcgatgtcg gctcatcaca tcctgggggct gaagtaggtc   2580 ccaagggtat ggctgttcgc catttaaagt ggtacgcgag ctgggtttaa aacgtcgtga   2640
gacagtttgg tccctatctg ccgtgggcgt tggagaattg agagggggctg ctcctagtac   2700 gagaggaccg gagtggacgc atcactggtg ttccggttgt gtcgccagac gcattgccgg   2760
```

```
gtagctacat gcggaagaga taagtgctga aagcatctaa gcacgaaact tgcctcgaga    2820
tgagttctcc cagtatttaa tactgtaagg gttgttggag acgacgacgt agataggccg    2880
ggtgtgtaag cgttgcgaga cgttgagcta accggtacta attgcccgag aggcttagcc    2940
atacaacgct caagtgtttt tggtagtgaa agttattacg gaataagtaa gtagtcaggg    3000
aatcggct                                                             3008
```

<210> SEQ ID NO 3
<211> LENGTH: 1029
<212> TYPE: DNA
<213> ORGANISM: Basfia succiniciproducens
<220> FEATURE:
<221> NAME/KEY: misc_feature
<223> OTHER INFORMATION: nucleotide sequence of ldhA-gene from strain
      DD1

<400> SEQUENCE: 3

```
ttgacaaaat cagtatgttt aaataaggag ctaactatga agttgccgt ttacagtact       60 aaaaattatg atcgcaaaca tctggatttg gcgaataaaa aatttaattt tgagcttcat     120
ttctttgatt ttttacttga tgaacaaacc gcgaaaatgg cggagggcgc cgatgccgtc     180
tgtattttcg tcaatgatga tgcgagccgc ccggtgttaa caagttggc gcaaatcgga     240 gtgaaaatta tcgctttacg ttgtgccggt tttaataatg tggatttgga ggcggcaaaa     300
gagctgggat taaaagtcgt acgggtgcct gcgtattcgc cggaagccgt tgccgagcat     360
gcgatcggat taatgctgac tttaaaccgc cgtatccata aggcttatca gcgtacccgc     420
gatgcgaatt tttctctgga aggattggtc ggttttaata tgttcggcaa aaccgccgga     480
gtgattggta cgggaaaaat cggcttggcg gctattcgca tttttaaaag cttcggtatg     540
gacgttctgg cgtttgatcc ttttaaaaat ccggcggcgg aagcgttggg cgcaaaatat     600
gtcggtttag acgagcttta tgcaaaatcc catgttatca ctttgcattg cccggctacg     660
gcggataatt atcatttatt aaatgaagcg gctttttaata aaatgcgcga cggtgtaatg     720
attattaata ccagccgcgg cgttttaatt gacagccggg cggcaatcga agcgttaaaa     780
cggcagaaaa tcggcgctct cggtatggat gtttatgaaa atgaacggga tttgttttc      840 gaggataaat ctaacgatgt tattacggat gatgtattcc gtcgcctttc ttcctgtcat     900
aatgtgcttt ttaccggtca tcaggcgttt ttaacgaag aagcgctgaa taatatcgcc      960
gatgtgactt tatcgaatat tcaggcggtt tccaaaaatg caacgtgcga aatagcgtt    1020 gaaggctaa                                                            1029
```

<210> SEQ ID NO 4
<211> LENGTH: 342
<212> TYPE: PRT
<213> ORGANISM: Basfia succiniciproducens
<220> FEATURE:
<221> NAME/KEY: MISC_FEATURE
<223> OTHER INFORMATION: amino acid sequence of LdhA from strain DD1

<400> SEQUENCE: 4

```
Met Thr Lys Ser Val Cys Leu Asn Lys Glu Leu Thr Met Lys Val Ala
1               5                   10                  15

Val Tyr Ser Thr Lys Asn Tyr Asp Arg Lys His Leu Asp Leu Ala Asn
            20                  25                  30

Lys Lys Phe Asn Phe Glu Leu His Phe Asp Phe Leu Leu Asp Glu
        35                  40                  45
```

```
Gln Thr Ala Lys Met Ala Glu Gly Ala Asp Ala Val Cys Ile Phe Val
    50              55                  60

Asn Asp Asp Ala Ser Arg Pro Val Leu Thr Lys Leu Ala Gln Ile Gly
 65              70                  75                  80

Val Lys Ile Ile Ala Leu Arg Cys Ala Gly Phe Asn Asn Val Asp Leu
                85                  90                  95

Glu Ala Ala Lys Glu Leu Gly Leu Lys Val Val Arg Val Pro Ala Tyr
            100                 105                 110

Ser Pro Glu Ala Val Ala Glu His Ala Ile Gly Leu Met Leu Thr Leu
        115                 120                 125

Asn Arg Arg Ile His Lys Ala Tyr Gln Arg Thr Arg Asp Ala Asn Phe
130                 135                 140

Ser Leu Glu Gly Leu Val Gly Phe Asn Met Phe Gly Lys Thr Ala Gly
145                 150                 155                 160

Val Ile Gly Thr Gly Lys Ile Gly Leu Ala Ala Ile Arg Ile Leu Lys
                165                 170                 175

Gly Phe Gly Met Asp Val Leu Ala Phe Asp Pro Phe Lys Asn Pro Ala
            180                 185                 190

Ala Glu Ala Leu Gly Ala Lys Tyr Val Gly Leu Asp Glu Leu Tyr Ala
        195                 200                 205

Lys Ser His Val Ile Thr Leu His Cys Pro Ala Thr Ala Asp Asn Tyr
210                 215                 220

His Leu Leu Asn Glu Ala Ala Phe Asn Lys Met Arg Asp Gly Val Met
225                 230                 235                 240

Ile Ile Asn Thr Ser Arg Gly Val Leu Ile Asp Ser Arg Ala Ala Ile
                245                 250                 255

Glu Ala Leu Lys Arg Gln Lys Ile Gly Ala Leu Gly Met Asp Val Tyr
            260                 265                 270

Glu Asn Glu Arg Asp Leu Phe Phe Glu Asp Lys Ser Asn Asp Val Ile
        275                 280                 285

Thr Asp Asp Val Phe Arg Arg Leu Ser Ser Cys His Asn Val Leu Phe
290                 295                 300

Thr Gly His Gln Ala Phe Leu Thr Glu Glu Ala Leu Asn Asn Ile Ala
305                 310                 315                 320

Asp Val Thr Leu Ser Asn Ile Gln Ala Val Ser Lys Asn Ala Thr Cys
                325                 330                 335

Glu Asn Ser Val Glu Gly
            340

<210> SEQ ID NO 5
<211> LENGTH: 741
<212> TYPE: DNA
<213> ORGANISM: Basfia succiniciproducens
<220> FEATURE:
<221> NAME/KEY: misc_feature
<223> OTHER INFORMATION: nucleotide sequence of pflA-gene from strain
      DD1

<400> SEQUENCE: 5
atgtcggttt taggacgaat tcattcattt gaaacctgcg ggacagttga cgggccggga    60
atccgcttta tttttatttt acaaggctgc ttaatgcgtt gtaaatactg ccataataga   120
gacacctggg atttgcacgg cggtaaagaa atttccgttg aagaattaat gaaagaagtg   180
gtgacctatc gccattttat gaacgcctcg ggcggcggag ttaccgcttc ggcggtgaa    240 gctatttac aggcggaatt tgtacgggac tggttcagag cctgccataa agaaggaatt    300
```

```
aatacttgct tggataccaa cggtttcgtc cgtcatcatg atcatattat tgatgaattg    360
attgatgaca cggatcttgt gttgcttgac ctgaaagaaa tgaatgaacg ggttcacgaa    420
agcctgattg gcgtgccgaa taaaagagtg ctcgaattcg caaatatttt agcggatcga    480
aatcagcgta cctggatccg ccatgttgta gtgccgggtt atacagatag tgacgaagat    540
ttgcacatgc tggggaattt cattaaagat atgaagaata tcgaaaaagt ggaattatta    600
ccttatcacc gtctaggcgc ccataaatgg aagtactcg gcgataaata cgagcttgaa    660
gatgtaaaac cgccgacaaa agaattaatg gagcatgtta aggggttgct tgcaggctac    720
gggcttaatg tgacatatta g                                              741
```

```
<210> SEQ ID NO 6
<211> LENGTH: 246
<212> TYPE: PRT
<213> ORGANISM: Basfia succiniciproducens
<220> FEATURE:
<221> NAME/KEY: MISC_FEATURE
<223> OTHER INFORMATION: amino acid sequence of PflA from strain DD1

<400> SEQUENCE: 6
```

Met Ser Val Leu Gly Arg Ile His Ser Phe Glu Thr Cys Gly Thr Val
1               5                   10                  15

Asp Gly Pro Gly Ile Arg Phe Ile Leu Phe Leu Gln Gly Cys Leu Met
            20                  25                  30

Arg Cys Lys Tyr Cys His Asn Arg Asp Thr Trp Asp Leu His Gly Gly
        35                  40                  45

Lys Glu Ile Ser Val Glu Glu Leu Met Lys Glu Val Val Thr Tyr Arg
    50                  55                  60

His Phe Met Asn Ala Ser Gly Gly Val Thr Ala Ser Gly Gly Glu
65                  70                  75                  80

Ala Ile Leu Gln Ala Glu Phe Val Arg Asp Trp Phe Arg Ala Cys His
                85                  90                  95

Lys Glu Gly Ile Asn Thr Cys Leu Asp Thr Asn Gly Phe Val Arg His
            100                 105                 110

His Asp His Ile Ile Asp Glu Leu Ile Asp Asp Thr Asp Leu Val Leu
        115                 120                 125

Leu Asp Leu Lys Glu Met Asn Glu Arg Val His Glu Ser Leu Ile Gly
    130                 135                 140

Val Pro Asn Lys Arg Val Leu Glu Phe Ala Lys Tyr Leu Ala Asp Arg
145                 150                 155                 160

Asn Gln Arg Thr Trp Ile Arg His Val Val Pro Gly Tyr Thr Asp
                165                 170                 175

Ser Asp Glu Asp Leu His Met Leu Gly Asn Phe Ile Lys Asp Met Lys
            180                 185                 190

Asn Ile Glu Lys Val Glu Leu Leu Pro Tyr His Arg Leu Gly Ala His
        195                 200                 205

Lys Trp Glu Val Leu Gly Asp Lys Tyr Glu Leu Glu Asp Val Lys Pro
    210                 215                 220

Pro Thr Lys Glu Leu Met Glu His Val Lys Gly Leu Leu Ala Gly Tyr
225                 230                 235                 240

Gly Leu Asn Val Thr Tyr
                245

```
<210> SEQ ID NO 7
<211> LENGTH: 2313
<212> TYPE: DNA
```

<213> ORGANISM: Basfia succiniciproducens
<220> FEATURE:
<221> NAME/KEY: misc_feature
<223> OTHER INFORMATION: nucleotide sequence of pflD-gene from strain DD1

<400> SEQUENCE: 7

```
atggctgaat taacagaagc tcaaaaaaaa gcatgggaag gattcgttcc cggtgaatgg       60
caaaacggcg taaatttacg tgactttatc caaaaaaact atactccgta tgaaggtgac      120
gaatcattct tagctgatgc gactcctgca accagcgagt tgtggaacag cgtgatggaa      180
ggcatcaaaa tcgaaaacaa aactcacgca cctttagatt tcgacgaaca tactccgtca      240
actatcactt ctcacaagcc tggttatatc aataaagatt tagaaaaaat cgttggtctt      300
caaacagacg ctccgttaaa acgtgcaatt atgccgtacg gcggtatcaa aatgatcaaa      360
ggttcttgcg aagtttacgg tcgtaaatta gatccgcaag tagaatttat tttcaccgaa      420
tatcgtaaaa cccataacca aggcgtattc gacgtttata cgccggatat tttacgctgc      480
cgtaaatcag gcgtgttaac cggtttaccg gatgcttacg gtcgtggtcg tattatcggt      540
gactaccgtc gtttagcggt atacggtatt gattacctga tgaaagataa aaaagcccaa      600
ttcgattcat tacaaccgcg tttggaagcg ggcgaagaca ttcaggcaac tatccaatta      660
cgtgaagaaa ttgccgaaca cacccgcgct ttaggcaaaa tcaaagaaat ggcggcatct      720
tacggttacg acatttccgg ccctgcgaca acgcacagg aagcaatcca atggacatat      780
tttgcttatc tggcagcggt taaatcacaa acggtgcgg caatgtcatt cggtcgtacg      840
tctacattct tagatatcta tatcgaacgt gacttaaaac gcggtttaat cactgaacaa      900
caggcgcagg aattaatgga ccacttagta atgaaattac gtatggttcg tttcttacgt      960
acgccggaat acgatcaatt attctcaggc gacccgatgt gggcaaccga aactatcgcc     1020
ggtatgggct tagacggtcg tccgttggta actaaaaaca gcttccgcgt attacatact     1080
ttatacacta tgggtacttc tccggaacca aacttaacta ttctttggtc cgaacaatta     1140
cctgaagcgt tcaaacgttt ctgtgcgaaa gtatctattg atacttcctc cgtacaatac     1200
gaaaatgatg acttaatgcg tcctgacttc aacaacgatg actatgcaat cgcatgctgc     1260
gtatcaccga tggtcgtagg taaacaaatg caattcttcg gtgcgcgcgc aaacttagct     1320
aaaactatgt tatacgcaat taacggcggt atcgatgaga aaaatggtat gcaagtcggt     1380
cctaaaactg cgccgattac agacgaagta ttgaatttcg ataccgtaat cgaacgtatg     1440
gacagtttca tggactggtt ggcgactcaa tatgtaaccg cattgaacat catccacttc     1500
atgcacgata aatatgcata tgaagcggca ttgatggcgt tccacgatcg cgacgtattc     1560
cgtacaatgg cttgcggtat cgcgggtctt tccgtggctg cggactcatt atccgcaatc     1620
aaatatgcga agttaaaacc gattcgcggc gacatcaaag ataaagacgg taatgtcgtg     1680
gcctcgaatg ttgctatcga cttcgaaatt gaaggcgaat atccgcaatt cggtaacaat     1740
gatccgcgtg ttgatgattt agcggtagac ttagttgaac gtttcatgaa aaaagttcaa     1800
aaacacaaaa cttaccgcaa cgcaactccg acacaatcta tcctgactat cacttctaac     1860
gtggtatacg gtaagaaaac cggtaatact ccggacggtc gtcgagcagg cgcgccattc     1920
ggaccgggtg caaacccaat gcacggtcgt gaccaaaaag gtgcggttgc ttcacttact     1980
tctgtggcta aacttccgtt cgcttacgcg aaagacggta tttcatatac cttctctatc     2040
gtaccgaacg cattaggtaa agatgacgaa gcgcaaaaac gcaaccttgc cggtttaatg     2100
gacggttatt tccatcatga agcgacagtg gaaggcggtc aacacttgaa tgttaacgtt     2160
```

-continued

```
cttaaccgtg aaatgttgtt agacgcgatg gaaaatccgg aaaaataccc gcaattaacc    2220
attcgtgttt caggttacgc ggttcgtttc aactcattaa ctaaagagca acaacaagac    2280
gtcatcactc gtacgtttac acaatcaatg taa                                 2313
```

<210> SEQ ID NO 8
<211> LENGTH: 770
<212> TYPE: PRT
<213> ORGANISM: Basfia succiniciproducens
<220> FEATURE:
<221> NAME/KEY: MISC_FEATURE
<223> OTHER INFORMATION: amino acid of PflD from strain DD1

<400> SEQUENCE: 8

```
Met Ala Glu Leu Thr Glu Ala Gln Lys Lys Ala Trp Glu Gly Phe Val
1               5                   10                  15

Pro Gly Glu Trp Gln Asn Gly Val Asn Leu Arg Asp Phe Ile Gln Lys
            20                  25                  30

Asn Tyr Thr Pro Tyr Glu Gly Asp Glu Ser Phe Leu Ala Asp Ala Thr
        35                  40                  45

Pro Ala Thr Ser Glu Leu Trp Asn Ser Val Met Glu Gly Ile Lys Ile
    50                  55                  60

Glu Asn Lys Thr His Ala Pro Leu Asp Phe Asp Glu His Thr Pro Ser
65                  70                  75                  80

Thr Ile Thr Ser His Lys Pro Gly Tyr Ile Asn Lys Asp Leu Glu Lys
                85                  90                  95

Ile Val Gly Leu Gln Thr Asp Ala Pro Leu Lys Arg Ala Ile Met Pro
            100                 105                 110

Tyr Gly Gly Ile Lys Met Ile Lys Gly Ser Cys Glu Val Tyr Gly Arg
        115                 120                 125

Lys Leu Asp Pro Gln Val Glu Phe Ile Phe Thr Glu Tyr Arg Lys Thr
    130                 135                 140

His Asn Gln Gly Val Phe Asp Val Tyr Thr Pro Asp Ile Leu Arg Cys
145                 150                 155                 160

Arg Lys Ser Gly Val Leu Thr Gly Leu Pro Asp Ala Tyr Gly Arg Gly
                165                 170                 175

Arg Ile Ile Gly Asp Tyr Arg Arg Leu Ala Val Tyr Gly Ile Asp Tyr
            180                 185                 190

Leu Met Lys Asp Lys Lys Ala Gln Phe Asp Ser Leu Gln Pro Arg Leu
        195                 200                 205

Glu Ala Gly Glu Asp Ile Gln Ala Thr Ile Gln Leu Arg Glu Glu Ile
    210                 215                 220

Ala Glu Gln His Arg Ala Leu Gly Lys Ile Lys Glu Met Ala Ala Ser
225                 230                 235                 240

Tyr Gly Tyr Asp Ile Ser Gly Pro Ala Thr Asn Ala Gln Glu Ala Ile
                245                 250                 255

Gln Trp Thr Tyr Phe Ala Tyr Leu Ala Ala Val Lys Ser Gln Asn Gly
            260                 265                 270

Ala Ala Met Ser Phe Gly Arg Thr Ser Thr Phe Leu Asp Ile Tyr Ile
        275                 280                 285

Glu Arg Asp Leu Lys Arg Gly Leu Ile Thr Glu Gln Ala Gln Glu
    290                 295                 300

Leu Met Asp His Leu Val Met Lys Leu Arg Met Val Arg Phe Leu Arg
305                 310                 315                 320

Thr Pro Glu Tyr Asp Gln Leu Phe Ser Gly Asp Pro Met Trp Ala Thr
```

-continued

```
                325                 330                 335
Glu Thr Ile Ala Gly Met Gly Leu Asp Gly Arg Pro Leu Val Thr Lys
            340                 345                 350
Asn Ser Phe Arg Val Leu His Thr Leu Tyr Thr Met Gly Thr Ser Pro
            355                 360                 365
Glu Pro Asn Leu Thr Ile Leu Trp Ser Glu Gln Leu Pro Glu Ala Phe
        370                 375                 380
Lys Arg Phe Cys Ala Lys Val Ser Ile Asp Thr Ser Ser Val Gln Tyr
385                 390                 395                 400
Glu Asn Asp Asp Leu Met Arg Pro Asp Phe Asn Asn Asp Asp Tyr Ala
                405                 410                 415
Ile Ala Cys Cys Val Ser Pro Met Val Val Gly Lys Gln Met Gln Phe
                420                 425                 430
Phe Gly Ala Arg Ala Asn Leu Ala Lys Thr Met Leu Tyr Ala Ile Asn
            435                 440                 445
Gly Gly Ile Asp Glu Lys Asn Gly Met Gln Val Gly Pro Lys Thr Ala
        450                 455                 460
Pro Ile Thr Asp Glu Val Leu Asn Phe Asp Thr Val Ile Glu Arg Met
465                 470                 475                 480
Asp Ser Phe Met Asp Trp Leu Ala Thr Gln Tyr Val Thr Ala Leu Asn
                485                 490                 495
Ile Ile His Phe Met His Asp Lys Tyr Ala Tyr Glu Ala Ala Leu Met
            500                 505                 510
Ala Phe His Asp Arg Asp Val Phe Arg Thr Met Ala Cys Gly Ile Ala
            515                 520                 525
Gly Leu Ser Val Ala Ala Asp Ser Leu Ser Ala Ile Lys Tyr Ala Lys
        530                 535                 540
Val Lys Pro Ile Arg Gly Asp Ile Lys Asp Lys Asp Gly Asn Val Val
545                 550                 555                 560
Ala Ser Asn Val Ala Ile Asp Phe Glu Ile Glu Gly Glu Tyr Pro Gln
                565                 570                 575
Phe Gly Asn Asn Asp Pro Arg Val Asp Asp Leu Ala Val Asp Leu Val
            580                 585                 590
Glu Arg Phe Met Lys Lys Val Gln Lys His Lys Thr Tyr Arg Asn Ala
        595                 600                 605
Thr Pro Thr Gln Ser Ile Leu Thr Ile Thr Ser Asn Val Val Tyr Gly
        610                 615                 620
Lys Lys Thr Gly Asn Thr Pro Asp Gly Arg Arg Ala Gly Ala Pro Phe
625                 630                 635                 640
Gly Pro Gly Ala Asn Pro Met His Gly Arg Asp Gln Lys Gly Ala Val
                645                 650                 655
Ala Ser Leu Thr Ser Val Ala Lys Leu Pro Phe Ala Tyr Ala Lys Asp
            660                 665                 670
Gly Ile Ser Tyr Thr Phe Ser Ile Val Pro Asn Ala Leu Gly Lys Asp
        675                 680                 685
Asp Glu Ala Gln Lys Arg Asn Leu Ala Gly Leu Met Asp Gly Tyr Phe
        690                 695                 700
His His Glu Ala Thr Val Glu Gly Gly Gln His Leu Asn Val Asn Val
705                 710                 715                 720
Leu Asn Arg Glu Met Leu Leu Asp Ala Met Glu Asn Pro Glu Lys Tyr
                725                 730                 735
Pro Gln Leu Thr Ile Arg Val Ser Gly Tyr Ala Val Arg Phe Asn Ser
            740                 745                 750
```

Leu Thr Lys Glu Gln Gln Gln Asp Val Ile Thr Arg Thr Phe Thr Gln
        755                 760                 765

Ser Met
    770

<210> SEQ ID NO 9
<211> LENGTH: 4285
<212> TYPE: DNA
<213> ORGANISM: artificial sequence
<220> FEATURE:
<223> OTHER INFORMATION: complete nucleotide sequence of plasmid pSacB

<400> SEQUENCE: 9

```
tcgagaggcc tgacgtcggg cccggtacca cgcgtcatat gactagttcg gacctaggga      60
tatcgtcgac atcgatgctc ttctgcgtta attacaatt  gggatcctct agactccata     120
ggccgctttc ctggctttgc ttccagatgt atgctctcct ccggagagta ccgtgacttt     180
attttcggca caaatacagg ggtcgatgga taaatacggc gatagtttcc tgacggatga     240
tccgtatgta ccggcggaag acaagctgca aacctgtcag atggagattg atttaatggc     300
ggatgtgctg agagcaccgc cccgtgaatc cgcagaactg atccgctatg tgtttgcgga     360
tgattggccg gaataaataa agccgggctt aatacagatt aagcccgtat agggtattat     420
tactgaatac caaacagctt acggaggacg gaatgttacc cattgagaca accagactgc     480
cttctgatta ttaatatttt tcactattaa tcagaaggaa taaccatgaa tttttacccgg     540
attgacctga atacctggaa tcgcaggaa  cactttgccc tttatcgtca gcagattaaa     600
tgcggattca gcctgaccac caaactcgat attaccgctt tgcgtaccgc actggcggag     660
acaggttata agttttatcc gctgatgatt tacctgatct cccgggctgt taatcagttt     720
ccggagttcc ggatggcact gaaagacaat gaacttattt actgggacca gtcagacccg     780
gtctttactg tctttcataa agaaaccgaa acattctctg cactgtcctg ccgttatttt     840
ccggatctca gtgagtttat ggcaggttat aatgcggtaa cggcagaata tcagcatgat     900
accagattgt ttccgcaggg aaatttaccg gagaatcacc tgaatatatc atcattaccg     960
tgggtgagtt ttgacgggat ttaacctgaa catcaccgga aatgatgatt attttgcccc    1020
ggttttacg  atggcaaagt ttcagcagga aggtgaccgc gtattattac ctgtttctgt    1080
acaggttcat catgcagtct gtgatggctt tcatgcagca cggtttatta atacacttca    1140
gctgatgtgt gataacatac tgaaataaat taattaattc tgtatttaag ccaccgtatc    1200
cggcaggaat ggtggctttt ttttatatt  ttaaccgtaa tctgtaattt cgtttcagac    1260
tggttcagga tgagctcgct tggactcctg ttgatagatc cagtaatgac ctcagaactc    1320
catctggatt tgttcagaac gctcggttgc cgccgggcgt tttttattgg tgagaatcca    1380
agcactagcg gcgcgccggc cggcccggtg tgaaataccg cacagatgcg taaggagaaa    1440
ataccgcatc aggcgctctt ccgcttcctc gctcactgac tcgctgcgct cggtcgttcg    1500
gctgcggcga gcggtatcag ctcactcaaa ggcggtaata cggttatcca cagaatcagg    1560
ggataacgca ggaaagaaca tgtgagcaaa aggccagcaa aaggccagga accgtaaaaa    1620
ggccgcgttg ctggcgtttt tccataggct ccgcccccct gacgagcatc acaaaaatcg    1680
acgctcaagt cagaggtggc gaaacccgac aggactataa agataccagg cgtttccccc    1740
tggaagctcc ctcgtgcgct ctcctgttcc gaccctgccg cttaccggat acctgtccgc    1800
ctttctccct tcgggaagcg tggcgctttc tcatagctca cgctgtaggt atctcagttc    1860
```

```
ggtgtaggtc gttcgctcca agctgggctg tgtgcacgaa ccccccgttc agcccgaccg      1920
ctgcgcctta tccggtaact atcgtcttga gtccaacccg gtaagacacg acttatcgcc      1980
actggcagca gccactggta acaggattag cagagcgagg tatgtaggcg gtgctacaga      2040
gttcttgaag tggtggccta actacggcta cactagaagg acagtatttg gtatctgcgc      2100
tctgctgaag ccagttacct tcggaaaaag agttggtagc tcttgatccg gcaaacaaac      2160
caccgctggt agcggtggtt ttttttgttt gcaagcagcag attacgcgca gaaaaaaagg      2220
atctcaagaa gatcctttga tcttttctac ggggtctgac gctcagtgga acgaaaactc      2280
acgttaaggg attttggtca tgagattatc aaaaaggatc ttcacctaga tccttttaaa      2340
ggccggccgc ggccgccatc ggcattttct tttgcgtttt tatttgttaa ctgttaattg      2400
tccttgttca aggatgctgt ctttgacaac agatgttttc ttgcctttga tgttcagcag      2460
gaagctcggc gcaaacgttg attgtttgtc tgcgtagaat cctctgtttg tcatatagct      2520
tgtaatcacg acattgtttc ctttcgcttg aggtacagcg aagtgtgagt aagtaaaggt      2580
tacatcgtta ggatcaagat ccattttaa cacaaggcca gttttgttca gcggcttgta      2640
tgggccagtt aaagaattag aaacataacc aagcatgtaa atatcgttag acgtaatgcc      2700
gtcaatcgtc attttgatc cgcgggagtc agtgaacagg taccatttgc cgttcatttt      2760
aaagacgttc gcgcgttcaa tttcatctgt tactgtgtta gatgcaatca gcggtttcat      2820
cacttttttc agtgtgtaat catcgttag ctcaatcata ccgagagcgc cgtttgctaa      2880
ctcagccgtg cgttttttat cgcttttgcag aagttttga cttttcttgac ggaagaatga      2940 tgtgctttg ccatagtatg ctttgttaaa taaagattct tcgccttggt agccatcttc      3000
agttccagtg tttgcttcaa atactaagta tttgtggcct ttatcttcta cgtagtgagg      3060
atctctcagc gtatggttgt cgcctgagct gtagttgcct tcatcgatga actgctgtac      3120
attttgatac gttttccgt caccgtcaaa gattgattta taatcctcta caccgttgat      3180
gttcaaagag ctgtctgatg ctgatacgtt aacttgtgca gttgtcagtg tttgtttgcc      3240
gtaatgttta ccggagaaat cagtgtagaa taaacggatt tttccgtcag atgtaaatgt      3300
ggctgaacct gaccattctt gtgtttggtc ttttaggata gaatcatttg catcgaattt      3360
gtcgctgtct ttaaagacgc ggccagcgtt tttccagctg tcaatagaag tttcgccgac      3420 ttttttgatag aacatgtaaa tcgatgtgtc atccgcattt ttaggatctc cggctaatgc      3480
aaagacgatg tggtagccgt gatagtttgc gacagtgccg tcagcgtttt gtaatggcca      3540
gctgtcccaa acgtccaggc cttttgcaga agagatattt ttaattgtgg acgaatcaaa      3600
ttcagaaact tgatattttt catttttttg ctgttcaggg atttgcagca tatcatggcg      3660
tgtaatatgg gaaatgccgt atgtttcctt atatggcttt tggttcgttt ctttcgcaaa      3720
cgcttgagtt gcgcctcctg ccagcagtgc ggtagtaaag gttaatactg ttgcttgttt      3780
tgcaaacttt ttgatgttca tcgttcatgt ctccttttt atgtactgtg ttagcggtct      3840
gcttcttcca gccctcctgt ttgaagatgg caagttagtt acgcacaata aaaaagacc      3900 taaaatatgt aagggtgac gccaaagtat acactttgcc ctttacacat tttaggtctt      3960
gcctgcttta tcagtaacaa acccgcgcga tttacttttc gacctcattc tattagactc      4020
tcgtttggat tgcaactggt ctattttcct cttttgtttg atagaaaatc ataaaggat      4080 ttgcagacta cgggcctaaa gaactaaaaa atctatctgt ttcttttcat tctctgtatt      4140
ttttatagtt tctgttgcat gggcataaag ttgccttttt aatcacaatt cagaaaatat      4200
cataatatct catttcacta ataatagtg aacggcaggt atatgtgatg ggttaaaaag      4260
```

```
gatcggcggc cgctcgattt aaatc                                        4285

<210> SEQ ID NO 10
<211> LENGTH: 7074
<212> TYPE: DNA
<213> ORGANISM: artificial sequence
<220> FEATURE:
<223> OTHER INFORMATION: complete nucleotide sequence of plasmid
      pSacB_delta_ldhA

<400> SEQUENCE: 10
tcgagaggcc tgacgtcggg cccggtacca cgcgtcatat gactagttcg gacctaggga     60
tgggtcagcc tgaacgaacc gcacttgtat gtaggtagtt ttgaccgccc gaatattcgt    120
tataccttgg tggaaaaatt caaaccgatg gagcaattat acaatttgt ggcggcgcaa    180 aaaggtaaaa gcggtatcgt ctattgcaac agccgtagca aagtggagcg cattgcggaa    240
gccctgaaga aaagaggcat ttccgcagcc gcttatcatg cgggcatgga gccgtcgcag    300
cgggaagcgg tgcaacaggc gtttcaacgg ataatattc aagtggtggt ggcgaccatt    360
gcttttggta tggggatcaa caaatctaat gtgcgttttg tggcgcattt tgatttatct    420
cgcagcattg aggcgtatta tcaggaaacc gggcgcgcgg ggcgggacga cctgccggcg    480
gaagcggtac tgttttacga gccggcggat tatgcctggt tgcataaaat tttattggaa    540
gagccggaaa gcccgcaacg ggatattaaa cggcataagc tggaagccat cggcgaattt    600
gccgaaagcc agacctgccg tcgtttagtg ctgttaaatt atttcggcga aaaccgccaa    660
acgccatgta ataactgtga tatctgcctc gatccgccga aaaatatga cggattatta    720 gacgcgcaga aaatcctttc gaccatttat cgcaccgggc aacgtttcgg cacgcaatac    780
gtaatcggcg taatgcgcgg tttgcagaat cagaaaataa agaaaatca acatgatgag    840 ttgaaagtct acggaattgg caaagataaa agcaaagaat actggcaatc ggtaattcgt    900
cagctgattc atttgggctt tgtgcaacaa atcatcagcg atttcggcat ggggaccaga    960
ttacagctca ccgaaagcgc gcgtcccgtg ctgcgcggcg aagtgtcttt ggaactggcc   1020
atgccgagat tatcttccat taccatggta caggctccgc aacgcaatgc ggtaaccaac   1080
tacgacaaag atttatttgc ccgcctgcgt ttcctgcgca aacagattgc cgacaaagaa   1140
aacattccgc cttatattgt gttcagtgac gcgaccttgc aggaaatgtc gttgtatcag   1200
ccgaccagca aagtggaaat gctgcaaatc aacggtgtcg gcgccatcaa atggcagcgc   1260
ttcggacagc tttttatggc gattattaaa gaacatcagg ctttgcgtaa agcgggtaag   1320
aatccgttgg aattgcaatc ttaaaatttt taacttttg accgcacttt taaggttagc   1380
aaattccaat aaaagtgcg gtgggttttc gggaatttt aacgcgctga tttcctcgtc   1440
ttttcaattt yttcgyctcc atttgttcgg yggttgccgg atcctttctt gactgagatc   1500
cataagagag tagaatagcg ccgcttatat ttttaatagc gtacctaatc gggtacgctt   1560
tttttatgcg gaaaatccat atttttctac cgcacttttt ctttaaagat ttatacttaa   1620
gtctgtttga ttcaatttat ttggaggttt tatgcaacac attcaactgg ctcccgattt   1680
aacattcagt cgcttaattc aaggattctg gcggttaaaa agctggcgga atcgccgca   1740 ggaattgctt acattcgtta agcaaggatt agaattaggc gttgatacgc tggatcatgc   1800
cgcttgttac ggggctttta cttccgaggc ggaattcgga cgggcgctgg cgctggataa   1860
atccttgcgc gcacagctta cttttggtga ccaaatgcggg attttgtatc ctaatgaaga   1920
attacccgat ataaaatccc atcactatga caacagctac cgccatatta tgtggtcggc   1980
```

```
gcaacgttcc attgaaaaac tgcaatgcga ctatttagat gtattgctga ttcaccgwct    2040
ttctccctgt gcggatcccg aacaaatcgc gcgggctttt gatgaacttt atcaaaccgg    2100
raaagtacgt tatttcgggg tatctaacta tacgccggct aagttcgcca tgttgcaatc    2160
ttatgtgaat cagccgttaa tcactaatca aattgagatt tcgcctcttc atcgtcaggc    2220
ttttgatgac ggtaccctgg attttttact ggaaaaacgt attcaaccga tggcatggtc    2280
gccacttgcc ggcggtcgtt tattcaatca ggatgagaac agtcgggcgg tgcaaaaaac    2340
attactcgaa atcggtgaaa cgaaaggaga aacccgttta gatacattgg cttatgcctg    2400
gttattggcg catccggcaa aaattatgcc ggttatgggg tccggtaaaa ttgaacgggt    2460
aaaaagcgcg gcggatgcgt tacgaatttc cttcactgag gaagaatgga ttaaggttta    2520
tgttgccgca cagggacggg atattccgta acatcatccg tctaatcctg cgtatctggg    2580
gaaagatgcg tcatcgtaag aggtctataa tattcgtcgt tttgataagg gtgccatatc    2640
cggcacccgt taaaatcaca ttgcgttcgc aacaaaatta ttccttacga atagcattca    2700
cctcttttaa cagatgttga atatccgtat cggcaaaaat atcctctata tttgcggtta    2760
aacggcgccg ccagttagca tattgagtgc tggttcccgg aatattgacg ggttcggtca    2820
taccgagcca gtcttcaggt tggaatcccc atcgtcgaca tcgatgctct tctgcgttaa    2880
ttaacaattg ggatcctcta gactccatag gccgctttcc tggctttgct tccagatgta    2940
tgctctcctc cggagagtac cgtgacttta ttttcggcac aaatacaggg gtcgatggat    3000
aaatacggcg atagtttcct gacggatgat ccgtatgtac cggcggaaga caagctgcaa    3060
acctgtcaga tggagattga tttaatggcg gatgtgctga gagcaccgcc ccgtgaatcc    3120
gcagaactga tccgctatgt gtttgcggat gattggccgg aataaataaa gccgggctta    3180
atacagatta agcccgtata gggtattatt actgaatacc aaacagctta cggaggacgg    3240
aatgttaccc attgagacaa ccagactgcc ttctgattat taatatttt cactattaat    3300 cagaaggaat aaccatgaat tttacccgga ttgacctgaa tacctggaat cgcagggaac    3360
actttgccct ttatcgtcag cagattaaat gcggattcag cctgaccacc aaactcgata    3420
ttaccgcttt gcgtaccgca ctggcggaga caggttataa gttttatccg ctgatgattt    3480
acctgatctc ccgggctgtt aatcagtttc cggagttccg gatggcactg aaagacaatg    3540 aacttatttta ctgggaccag tcagacccgg tctttactgt cttt cataaa gaaaccgaaa    3600 cattctctgc actgtcctgc cgttattttc cggatctcag tgagtttatg gcaggttata    3660
atgcggtaac ggcagaatat cagcatgata ccagattgtt tccgcaggga aatttaccgg    3720
agaatcacct gaatatatca tcattaccgt gggtgagttt tgacgggatt taacctgaac    3780
atcaccggaa atgatgatta ttttgccccg gttttacga tggcaaagtt tcagcaggaa    3840
ggtgaccgcg tattattacc tgtttctgta caggttcatc atgcagtctg tgatggcttt    3900
catgcagcac ggtttattaa tacacttcag ctgatgtgtg ataacatact gaaataaatt    3960
aattaattct gtatttaagc caccgtatcc ggcaggaatg gtggcttttt tttatattt    4020 taaccgtaat ctgtaatttc gtttcagact ggttcaggat gagctcgctt ggactcctgt    4080
tgatagatcc agtaatgacc tcagaactcc atctggattt gttcagaacg ctcggttgcc    4140
gccgggcgtt ttttattggt gagaatccaa gcactagcgg cgcgccggcc ggcccggtgt    4200
gaaataccgc acagatgcgt aaggagaaaa taccgcatca ggcgctcttc cgcttcctcg    4260
ctcactgact cgctgcgctc ggtcgttcgg ctgcggcgag cggtatcagc tcactcaaag    4320
```

-continued

```
gcggtaatac ggttatccac agaatcaggg gataacgcag gaaagaacat gtgagcaaaa      4380
ggccagcaaa aggccaggaa ccgtaaaaag gccgcgttgc tggcgttttt ccataggctc      4440
cgcccccctg acgagcatca caaaaatcga cgctcaagtc agaggtggcg aaacccgaca      4500
ggactataaa gataccaggc gtttccccct ggaagctccc tcgtgcgctc tcctgttccg      4560
accctgccgc ttaccggata cctgtccgcc tttctccctt cgggaagcgt ggcgctttct      4620
catagctcac gctgtaggta tctcagttcg gtgtaggtcg ttcgctccaa gctgggctgt      4680
gtgcacgaac cccccgttca gcccgaccgc tgcgccttat ccggtaacta tcgtcttgag      4740
tccaacccgg taagacacga cttatcgcca ctggcagcag ccactggtaa caggattagc      4800
agagcgaggt atgtaggcgg tgctacagag ttcttgaagt ggtggcctaa ctacggctac      4860
actagaagga cagtatttgg tatctgcgct ctgctgaagc cagttacctt cggaaaaaga      4920
gttggtagct cttgatccgg caaacaaacc accgctggta gcggtggttt ttttgtttgc      4980
aagcagcaga ttacgcgcag aaaaaaagga tctcaagaag atcctttgat cttttctacg      5040
gggtctgacg ctcagtggaa cgaaaactca cgttaaggga ttttggtcat gagattatca      5100
aaaaggatct tcacctagat ccttttaaag gccggccgcg gccgccatcg gcattttctt      5160
ttgcgttttt atttgttaac tgttaattgt ccttgttcaa ggatgctgtc tttgacaaca      5220
gatgttttct tgcctttgat gttcagcagg aagctcggcg caaacgttga ttgtttgtct      5280
gcgtagaatc ctctgtttgt catatagctt gtaatcacga cattgtttcc tttcgcttga      5340
ggtacagcga agtgtgagta agtaaaggtt acatcgttag gatcaagatc catttttaac      5400
acaaggccag ttttgttcag cggcttgtat gggccagtta agaattaga aacataacca      5460 agcatgtaaa tatcgttaga cgtaatgccg tcaatcgtca tttttgatcc gcgggagtca      5520
gtgaacaggt accatttgcc gttcatttta aagacgttcg cgcgttcaat ttcatctgtt      5580
actgtgttag atgcaatcag cggtttcatc acttttttca gtgtgtaatc atcgtttagc      5640
tcaatcatac cgagagcgcc gtttgctaac tcagccgtgc gttttttatc gctttgcaga      5700 agttttgac tttcttgacg gaagaatgat gtgcttttgc catagtatgc tttgttaaat       5760
aaagattctt cgccttggta gccatcttca gttccagtgt ttgcttcaaa tactaagtat      5820
ttgtggcctt tatcttctac gtagtgagga tctctcagcg tatggttgtc gcctgagctg      5880
tagttgcctt catcgatgaa ctgctgtaca ttttgatacg ttttccgtc accgtcaaag       5940 attgatttat aatcctctac accgttgatg ttcaaagagc tgtctgatgc tgatacgtta      6000
acttgtgcag ttgtcagtgt tgtttgccg taatgtttac cggagaaatc agtgtagaat       6060
aaacggattt ttccgtcaga tgtaaatgtg gctgaacctg accattcttg tgtttggtct      6120
tttaggatag aatcatttgc atcgaatttg tcgctgtctt taaagacgcg gccagcgttt      6180
ttccagctgt caatagaagt ttcgccgact ttttgataga acatgtaaat cgatgtgtca      6240
tccgcatttt taggatctcc ggctaatgca aagacgatgt ggtagccgtg atagtttgcg      6300
acagtgccgt cagcgttttg taatggccag ctgtcccaaa cgtccaggcc ttttgcagaa      6360
gagatatttt taattgtgga cgaatcaaat tcagaaactt gatattttc atttttttgc       6420 tgttcaggga tttgcagcat atcatggcgt gtaatatggg aaatgccgta tgtttcctta      6480
tatggctttt ggttcgtttc tttcgcaaac gcttgagttg cgcctcctgc cagcagtgcg      6540
gtagtaaagg ttaatactgt tgcttgtttt gcaaactttt tgatgttcat cgttcatgtc      6600 tccttttta tgtactgtgt tagcggtctg cttcttccag ccctcctgtt tgaagatggc        6660
aagttagtta cgcacaataa aaaaagacct aaaatatgta agggtgacg ccaaagtata        6720
```

```
cactttgccc tttacacatt ttaggtcttg cctgctttat cagtaacaaa cccgcgcgat      6780
ttacttttcg acctcattct attagactct cgtttggatt gcaactggtc tattttcctc      6840
ttttgtttga tagaaaatca taaaaggatt tgcagactac gggcctaaag aactaaaaaa      6900
tctatctgtt tcttttcatt ctctgtattt tttatagttt ctgttgcatg gcataaagt       6960 tgccttttta atcacaattc agaaaatatc ataatatctc atttcactaa ataatagtga      7020
acggcaggta tatgtgatgg gttaaaaagg atcggcggcc gctcgattta aatc            7074

<210> SEQ ID NO 11
<211> LENGTH: 7183
<212> TYPE: DNA
<213> ORGANISM: artificial sequence
<220> FEATURE:
<223> OTHER INFORMATION: complete nucleotide sequence of plasmid
      pSacB_delta_pflA

<400> SEQUENCE: 11
tcgagtcaat gcggatttga cttatgatgt ggcaaacaac cgatttccga ttattactac        60
acgtaaaagt tattggaaag cggcgattgc ggagtttctg ggttatatcc gcggctacga       120
taatgcggcg gatttccgta aattaggagc aaaaacctgg gatgccaacg ctaatgaaaa       180
tcaggtatgg ctgaataacc ctcatcgcaa aggcaccgac gacatggggc gcgtttacgg       240
cgtacagggc agagcctggc gtaagcctaa cggcgaaacc gttgatcaat tacgcaaaat       300
tgtcaacaat ttaagtcgcg gcattgatga tcgcggcgaa attctgacct tttttaaaccc      360 gggcgaattc gatctcggtt gtctgcgccc ttgtatgtac aatcacacgt tttctttgct       420
gggcgatacg ctttatttaa ccagttatca acgctcctgt gacgtacctt taggcttgaa       480
tttcaatcaa attcaagtat ttacattctt agctttaatg gcgcagatta ccggtaaaaa       540
agccggtcag gcatatcaca aaatcgtcaa tgcgcatatt tacgaagacc agctggaact       600
aatgcgcgac gtgcagttaa aacgcgaacc gttcccgtcg ccaaaactgg aaattaatcc       660
ggacattaaa acccttgaag atttagaaac ctgggtaacc atggatgatt tcaacgtcgt       720
tggttaccaa tgccacgaac cgataaaata tccgttctcg gtataaaccg acaaaagtgc       780
ggtcaaaaat ttaatatttt catctgttat agaaaatatt tttcaacata aaatctaggg       840
atgcctgttt ggcgtccgta aatacgcaga aaaatattaa attttgacc gcactttttt        900 catctcaatt aacagcctga taattcttat ggatcaacaa attagctttg acgaaaaaat       960
gatgaatcga gctcttttcc ttgccgacaa ggcggaagct ttaggggaaa ttcccgtagg      1020
tgccgtattg gtggatgaac ggggcaatat cattggtgaa ggctggaacc tctctattgt      1080
gaactcggat cccaccgccc atgccgaaat tattgcgttg cgtaacgccg cgcagaaaat      1140
ccaaaattac cgcctgctca ataccacttt atacgtgact ttagaaccct gcaccatgtg      1200
cgccggcgcg attttacaca gccgaatcaa acgcttggta ttcggggcgt ccgattacaa      1260
aaccggtgcg gtgggttcca gatttcattt ttttgaggat tataaaatga atcatggggt      1320
tgagatcaca agcggtgtct tacaggatca atgcagtcag aagttaagcc gcttttccca      1380
aaagcgcagg gaacagaaaa acaacaaaaa agctaccgca cttttacaac accccggct       1440 taactcctct gaaaaatagt gacaaaaaaa ccgtcataat gtttacgacg gtttttttat      1500
ttcttaatat gcccttaaat aatcaacaaa atatagcaag aagattatag caaagaattt      1560 cgttttttc agagaaatagt caaatcttcg caaaaaacta ccgcactttt atccgcttta      1620
atcaggggaa ttaaaacaaa aaaattccgc ctattgaggc ggaatttatt aagcaataag      1680
```

```
acaaactctc aattacattg attgtgtaaa cgtacgagtg atgacgtctt gttgttgctc   1740
tttagttaat gagttgaaac gaaccgcgta acctgaaaca cgaatggtta attgcgggta   1800
tttttccgga ttttccatcg cgtctaacaa catttcacgg ttaagaacgt taacattcaa   1860
gtgttgaccg ccttccactg tcgcttcatg atggaaataa ccgtccatta aaccggcaag   1920
gttgcgtttt tgcgcttcgt catctttacc taatgcgttc ggtacgatag agaaggtata   1980
tgaaataccg tctttcgcgt aagcgaacgg aagtttagcc acagaagtaa gtgaagcaac   2040
cgcacctttt tggtcacgac cgtgcattgg gtttgcaccc ggtccgaatg cgcgcctgc    2100 tcgacgaccg tccggagtat taccggtttt cttaccgtat accacgttag aagtgatagt   2160
caggatagat tgtgtcggag ttgcgttgcg gtaagttttg tgtttttgaa cttttttcat   2220
gaaacgttca actaagtcta ccgctaaatc atcaacacgc ggatcattgt taccgaattg   2280
cggatattcg ccttcaattt cgaagtcgat agcaacattc gaggccacga cattaccgtc   2340
tttatctttg atgtcgccgc gaatcggttt aactttcgca tatttgattg cggataatga   2400
gtccgcagcc acggaaagac ccgcgatacc gcaagccatt gtacggaata cgtcgcgatc   2460
gtggaacgcc atcaatgccg cttcatatgc atatttatcg tgcatgaagt ggatgatgtt   2520
caatgcggtt acatattgag tcgccaacca gtccatgaaa ctgtccatac gttcgattac   2580
ggtatcgaaa ttcaatactt cgtctgtaat cggcgcagtt ttaggaccga cttgcatacc   2640 attttctca tcgataccgc cgttaattgc gtataacata gttttagcta agtttgcgcg    2700
cgcaccgaag aattgcattt gtttacctac gaccatcggt gatacgcagc atgcgattgc   2760
atagtcatcg ttgttgaagt caggacgcat taagtcatca ttttcgtatt gtacggagga   2820
agtatcaata gatactttcg cacagaaacg tttgaacgct tcaggtaatt gttcggacca   2880
aagaatagtt aagtttggtt ccggagaagt acccatagtg tataaagtat gtaatacgcg   2940
gaagctgttt ttagttacca acggacgacc gtctaagccc ataccggcga tagtttcggt   3000
tgccctctag actccatagg ccgctttcct ggctttgctt ccagatgtat gctctcctcc   3060
ggagagtacc gtgactttat tttcggcaca aatacagggg tcgatggata aatacgcga    3120 tagtttcctg acgatgatc cgtatgtacc ggcggaagac aagctgcaaa cctgtcagat    3180
ggagattgat ttaatggcgg atgtgctgag agcaccgccc cgtgaatccg cagaactgat   3240
ccgctatgtg tttgcggatg attggccgga ataaataaag ccgggcttaa tacagattaa   3300
gcccgtatag ggtattatta ctgaatacca aacagcttac ggaggacgga atgttaccca   3360
ttgagacaac cagactgcct tctgattatt aatattttc actattaatc agaaggaata    3420
accatgaatt ttacccggat tgacctgaat acctggaatc gcagggaaca ctttgcccctt  3480 tatcgtcagc agattaaatg cggattcagc ctgaccacca aactcgatat taccgctttg   3540
cgtaccgcac tggcggagac aggttataag ttttatccgc tgatgattta cctgatctcc   3600
cgggctgtta atcagtttcc ggagttccgg atggcactga agacaatga acttatttac    3660 tgggaccagt cagacccggt ctttactgtc tttcataaag aaaccgaaac attctctgca   3720
ctgtcctgcc gttatttcc ggatctcagt gagtttatgg caggttataa tgcggtaacg    3780
gcagaatatc agcatgatac cagattgttt ccgcagggaa atttaccgga gaatcacctg   3840
aatatatcat cattaccgtg ggtgagtttt gacgggattt aacctgaaca tcaccggaaa   3900
tgatgattat tttgccccgg ttttacgat ggcaaagttt cagcaggaag gtgaccgcgt    3960
attattacct gtttctgtac aggttcatca tgcagtctgt gatggctttc atgcagcacg   4020
```

```
gtttattaat acacttcagc tgatgtgtga taacatactg aaataaatta attaattctg    4080
tatttaagcc accgtatccg gcaggaatgg tggctttttt tttatatttt aaccgtaatc    4140
tgtaatttcg tttcagactg gttcaggatg agctcgcttg gactcctgtt gatagatcca    4200
gtaatgacct cagaactcca tctggatttg ttcagaacgc tcggttgccg ccgggcgttt    4260
tttattggtg agaatccaag cactagcggc gcgccggccg gcccggtgtg aaataccgca    4320
cagatgcgta aggagaaaat accgcatcag gcgctcttcc gcttcctcgc tcactgactc    4380
gctgcgctcg tcgttcggc tgcggcgagc ggtatcagct cactcaaagg cggtaatacg    4440
gttatccaca gaatcagggg ataacgcagg aaagaacatg tgagcaaaag gccagcaaaa    4500
ggccaggaac cgtaaaaagg ccgcgttgct ggcgtttttc cataggctcc gcccccctga    4560
cgagcatcac aaaaatcgac gctcaagtca gaggtggcga acccgacag gactataaag    4620 ataccaggcg tttccccctg gaagctccct cgtgcgctct cctgttccga ccctgccgct    4680
taccggatac ctgtccgcct ttctcccttc gggaagcgtg gcgctttctc atagctcacg    4740
ctgtaggtat ctcagttcgg tgtaggtcgt tcgctccaag ctgggctgtg tgcacgaacc    4800
ccccgttcag cccgaccgct gcgccttatc cggtaactat cgtcttgagt ccaacccggt    4860
aagacacgac ttatcgccac tggcagcagc cactggtaac aggattagca gagcgaggta    4920
tgtaggcggt gctacagagt tcttgaagtg gtggcctaac tacggctaca ctagaaggac    4980
agtatttggt atctgcgctc tgctgaagcc agttaccttc ggaaaaagag ttggtagctc    5040
ttgatccggc aaacaaacca ccgctggtag cggtggtttt tttgtttgca agcagcagat    5100
tacgcgcaga aaaaaggat ctcaagaaga tcctttgatc ttttctacgg ggtctgacgc    5160
tcagtggaac gaaaactcac gttaagggat tttggtcatg agattatcaa aaaggatctt    5220
cacctagatc cttttaaagg ccggccgcgg ccgccatcgg cattttcttt tgcgttttta    5280
tttgttaact gttaattgtc cttgttcaag gatgctgtct ttgacaacag atgttttctt    5340
gcctttgatg ttcagcagga agctcggcgc aaacgttgat tgtttgtctg cgtagaatcc    5400
tctgtttgtc atatagcttg taatcacgac attgtttcct ttcgcttgag gtacagcgaa    5460
gtgtgagtaa gtaaaggtta catcgttagg atcaagatcc attttttaaca caaggccagt    5520 tttgttcagc ggcttgtatg ggccagttaa agaattagaa acataaccaa gcatgtaaat    5580
atcgttagac gtaatgccgt caatcgtcat ttttgatccg cgggagtcag tgaacaggta    5640
ccatttgccg ttcattttaa agacgttcgc gcgttcaatt tcatctgtta ctgtgttaga    5700
tgcaatcagc ggtttcatca cttttttcag tgtgtaatca tcgtttagct caatcatacc    5760
gagagcgccg tttgctaact cagccgtgcg ttttttatcg ctttgcagaa gttttttgact    5820 ttcttgacgg aagaatgatg tgcttttgcc atagtatgct ttgttaaata agattcttc    5880 gccttggtag ccatcttcag ttccagtgtt tgcttcaaat actaagtatt tgtggccttt    5940
atcttctacg tagtgaggat ctctcagcgt atggttgtcg cctgagctgt agttgccttc    6000
atcgatgaac tgctgtacat tttgatacgt ttttccgtca ccgtcaaaga ttgatttata    6060
atcctctaca ccgttgatgt tcaaagagct gtctgatgct gatacgttaa cttgtgcagt    6120
tgtcagtgtt tgtttgccgt aatgtttacc ggagaaatca gtgtagaata aacggatttt    6180
tccgtcagat gtaaatgtgg ctgaacctga ccattcttgt gtttggtctt ttaggataga    6240
atcatttgca tcgaatttgt cgctgtcttt aaagacgcgg ccagcgtttt tccagctgtc    6300
aatagaagtt tcgccgactt tttgatagaa catgtaaatc gatgtgtcat ccgcattttt    6360
aggatctccg gctaatgcaa agacgatgtg gtagccgtga tagtttgcga cagtgccgtc    6420
```

```
agcgttttgt aatggccagc tgtcccaaac gtccaggcct tttgcagaag agatatttt     6480 aattgtggac gaatcaaatt cagaaacttg atattttca ttttttgct gttcagggat      6540 ttgcagcata tcatggcgtg taatatggga aatgccgtat gtttccttat atggcttttg    6600
gttcgtttct ttcgcaaacg cttgagttgc gcctcctgcc agcagtgcgg tagtaaaggt    6660
taatactgtt gcttgttttg caaacttttt gatgttcatc gttcatgtct cctttttat    6720 gtactgtgtt agcggtctgc ttcttccagc cctcctgttt gaagatggca agttagttac    6780
gcacaataaa aaagaccta aatatgtaa ggggtgacgc caagtatac actttgccct       6840 ttacacattt taggtcttgc ctgctttatc agtaacaaac ccgcgcgatt tacttttcga    6900
cctcattcta ttagactctc gtttggattg caactggtct attttcctct tttgtttgat    6960
agaaaatcat aaaaggattt gcagactacg ggcctaaaga actaaaaat ctatctgttt     7020 cttttcattc tctgtatttt ttatagtttc tgttgcatgg cataaagtt gccttttaa      7080 tcacaattca gaaatatca taatatctca tttcactaaa taatagtgaa cggcaggtat     7140
atgtgatggg ttaaaaagga tcggcggccg ctcgatttaa atc                      7183

<210> SEQ ID NO 12
<211> LENGTH: 7161
<212> TYPE: DNA
<213> ORGANISM: artificial sequence
<220> FEATURE:
<223> OTHER INFORMATION: complete nucleotide sequence of plasmid
      pSacB_pflD

<400> SEQUENCE: 12
tcgagaggcc tgacgtcggg cccggtacca cgcgtcatat gactagttcg gacctaggga     60
tgggatcgag ctcttttcct tgccgacaag gcggaagctt tagggaaat tcccgtaggt     120 gccgtattgg tggatgaacg gggcaatatc attggtgaag gctggaacct ctctattgtg    180
aactcggatc ccaccgccca tgccgaaatt attgcgttgc gtaacgccgc gcagaaaatc    240
caaaattacc gcctgctcaa taccactta tacgtgactt tagaaccctg caccatgtgc     300
gccggcgcga ttttacacag ccgaatcaaa cgcttggtat tcggggcgtc cgattacaaa    360
accggtgcgg tgggttccag atttcattt tttgaggatt ataaaatgaa tcatggggtt     420
gagatcacaa gcggtgtctt ataggatcaa tgcagtcaga agttaagccg cttttcccaa    480
aagcgcaggg aacagaaaa caacaaaaa gctaccgcac ttttacaaca cccccggctt      540
aactcctctg aaaatagtg acaaaaaac cgtcataatg tttacgacgg tttttttatt      600
tcttctaata tgtcacatta agcccgtagc ctgcaagcaa ccccttaaca tgctccatta    660
attcttttgt cggcggtttt acatcttcaa gctcgtattt atcgccgagt acttcccatt    720
tatgggcgcc tagacggtga taaggtaata attccacttt tcgatattc ttcatatctt     780 taatgaaatt ccccagcatg tgcaaatctt cgtcactatc tgtataaccc ggcactacaa    840
catggcggat ccaggtacgc tgatttcgat ccgctaaata ttttgcgaat tcgagcactc    900
ttttattcgg cacgccaatc aggctttcgt gaacccgttc attcatttct ttcaggtcaa    960
gcaacacaag atccgtgtca tcaatcaatt catcaataat atgatcatga tgacggacga   1020
aaccgttggt atccaagcaa gtattaattc cttctttatg gcaggctctg aaccagtccc   1080
gtacaaattc cgcctgtaaa atagcttcac cgccggaagc ggtaactccg ccgcccgagg   1140
cgttcataaa atgcgatag gtcaccactt cttttcattaa ttcttcaacg gaaatttctt   1200
taccgccgtg caaatcccag gtgtctctgt tatggcaata tttacaacgc attaagcagc   1260
```

```
cttgtaaaaa taaaataaag cggattcccg gcccgtcaac tgtcccgcag gtttcaaatg    1320
aatgaattcg tcctaaaacc gacataatat gcccttaaat aatcaacaaa atatagcaag    1380
aagattatag caaagaattt cgttttttc agagaatagt caaatcttcg caaaaaacta     1440
ccgcactttt atccgcttta atcaggggaa ttaaaacaaa aaaattccgc ctattgaggc    1500
ggaatttatt aagcaataag acaaactctc aatttaata cttccttctt ttctagtatt     1560
gataagattg aaaccttgca aggatgacgg cggatttgcc gtcactctca cccaactaat    1620
gtggacgact ggtaaaccat tgcattagac caatgcaaac accaccaccg acgatgttac    1680
ctaaagtaac aggaattaaa tttttaatta ctaaatggta catatctaaa tttgcaaact    1740
gctcggcatt taaacccgtt gcctgccaga attccggcga tgcgaaattt gcaattacca    1800
tgcccatagg gatcataaac atatttgcta cgcagtgttc aaagcctgaa gcgacaaaya    1860
acccgatcgg caggatcata ataaaagctt tatccgttag agtyttgccg gcataggcca    1920
tccaaacggc aatacatacc ataatgttgc aaagaatacc taaacagaag gcttcaaycc    1980
aggtatgttc tattttatgt tgtgccgtat ttaaaatggt taatccccac tgaccgtttg    2040
ccgccatgat ctgaccggaa accaaatta atgcaacaat aaataaaccg ccgacaaaat     2100
taccgaarta aaccacaatc cagttacgta acatctgaat tgttgtaatt ttactctcaa    2160
agcgggcaat agtcgataaa gttgatgaag taaatagttc acagccgcaa accgccacca    2220
taattacccc gagagagaac accaaaccgc cgaccagttt agttaatccc caaggcgctc    2280
ccgcagaggc tgtttgagtt gttgtataaa aaacgaatgc aagagcaata aacataccgg    2340
cagagatcgc cgataaaaat gaataggctt gttttttcgt agctttataa acgccgacgt    2400
ctaacccggt ttgagccatc tcggttggcg aagccatcca agccaattta aaatcttccg    2460
atttcattga gctttcctta gtaataaaac tactcggaaa tgagtagaac tgccttaaag    2520
cataaatgat agattaaaaa atccaaaatt gttgaatatt atttaacggg gggattataa    2580
aagattcata aattagataa tagctaattt gagtgatcca tatcacccttt tacagatttt    2640 ttgacctaaa tcaaaattac ccaaatagag taataatacc attataaagg gtgtggattt    2700
attcctttgg tttacgagat aaattgctat ttaagctgat ttctgataaa aagtgcggta    2760
gattttcccc aaaaataagg aaacacaaaa tggcagaaga aacaatttc agtaaaatta     2820 ttcgtaaaga aattcccgcc gacattatat atcaagacga tcttgtcacc gcatttcgcg    2880
atattgcgcc gcaggcaaaa actcatattt taattattcc gaataaattg attccgacag    2940
taaacgacgt aaccgcccat cgtcgacatc gatgctcttc tgcgttaatt aacaattggg    3000
atcctctaga ctttgcttcc agatgtatgc tctcctccgg agagtaccgt gactttattt    3060
tcggcacaaa tacaggggtc gatggataaa tacggcgata gtttcctgac ggatgatccg    3120
tatgtaccgg cggaagacaa gctgcaaacc tgtcagatgg agattgattt aatggcggat    3180
gtgctgagag caccgccccg tgaatccgca gaactgatcc gctatgtgtt tgcggatgat    3240
tggccggaat aaataaagcc gggcttaata cagattaagc ccgtataggg tattattact    3300
gaataccaaa cagcttacgg aggacggaat gttacccatt gagacaacca gactgccttc    3360
tgattattaa tattttcac tattaatcag aaggaataac catgaatttt acccggattg     3420
acctgaatac ctggaatcgc agggaacact tgcccttta tcgtcagcag attaaatgcg     3480
gattcagcct gaccaccaaa ctcgatatta ccgctttgcg taccgcactg gcggagacag    3540
gttataagtt ttatccgctg atgatttacc tgatctcccg ggctgttaat cagtttccgg    3600
```

```
agttccggat ggcactgaaa gacaatgaac ttatttactg ggaccagtca gacccggtct    3660
ttactgtctt tcataaagaa accgaaacat tctctgcact gtcctgccgt tattttccgg    3720
atctcagtga gtttatggca ggttataatg cggtaacggc agaatatcag catgatacca    3780
gattgtttcc gcagggaaat ttaccggaga atcacctgaa tatatcatca ttaccgtggg    3840
tgagttttga cgggatttaa cctgaacatc accggaaatg atgattattt tgccccggtt    3900
tttacgatgg caaagtttca gcaggaaggt gaccgcgtat tattacctgt ttctgtacag    3960
gttcatcatg cagtctgtga tggctttcat gcagcacggt ttattaatac acttcagctg    4020
atgtgtgata acatactgaa ataaattaat taattctgta tttaagccac cgtatccggc    4080
aggaatggtg cttttttttt tatattttaa ccgtaatctg taatttcgtt tcagactggt    4140
tcaggatgag ctcgcttgga ctcctgttga tagatccagt aatgacctca gaactccatc    4200
tggatttgtt cagaacgctc ggttgccgcc gggcgttttt tattggtgag aatccaagca    4260
ctagcggcgc gccggccggc ccggtgtgaa ataccgcaca gatgcgtaag gagaaaatac    4320
cgcatcaggc gctcttccgc ttcctcgctc actgactcgc tgcgctcggt cgttcggctg    4380
cggcgagcgg tatcagctca ctcaaaggcg gtaatacggt tatccacaga atcaggggat    4440
aacgcaggaa agaacatgtg agcaaaaggc cagcaaaagg ccaggaaccg taaaaaggcc    4500
gcgttgctgg cgtttttcca taggctccgc cccccctgacg agcatcacaa aaatcgacgc    4560
tcaagtcaga ggtggcgaaa cccgacagga ctataaagat accaggcgtt ccccctggaa    4620
agctccctcg tgcgctctcc tgttccgacc ctgccgctta ccggatacct gtccgccttt    4680
ctcccttcgg gaagcgtggc gctttctcat agctcacgct gtaggtatct cagttcggtg    4740
taggtcgttc gctccaagct gggctgtgtg cacgaacccc ccgttcagcc cgaccgctgc    4800
gccttatccg gtaactatcg tcttgagtcc aacccggtaa gacacgactt atcgccactg    4860
gcagcagcca ctggtaacag gattagcaga gcgaggtatg taggcggtgc tacagagttc    4920
ttgaagtggt ggcctaacta cggctacact agaaggacag tatttggtat ctgcgctctg    4980
ctgaagccag ttaccttcgg aaaaagagtt ggtagctctt gatccggcaa caaaccacc    5040 gctggtagcg gtggtttttt tgtttgcaag cagcagatta cgcgcagaaa aaaggatct    5100 caagaagatc ctttgatctt ttctacgggg tctgacgctc agtggaacga aaactcacgt    5160
taagggattt tggtcatgag attatcaaaa aggatcttca cctagatcct ttaaaggcc    5220 ggccgcggcc gccatcggca ttttcttttg cgtttttatt tgttaactgt taattgtcct    5280
tgttcaagga tgctgtcttt gacaacagat gttttcttgc ctttgatgtt cagcaggaag    5340
ctcggcgcaa acgttgattg tttgtctgcg tagaatcctc tgtttgtcat atagcttgta    5400
atcacgacat tgtttccttt cgcttgaggt acagcgaagt gtgagtaagt aaaggttaca    5460
tcgttaggat caagatccat ttttaacaca aggccagttt tgttcagcgg cttgtatggg    5520
ccagttaaag aattagaaac ataaccaagc atgtaaatat cgttagacgt aatgccgtca    5580
atcgtcattt ttgatccgcg ggagtcagtg aacaggtacc atttgccgtt cattttaaag    5640
acgttcgcgc gttcaatttc atctgttact gtgttagatg caatcagcgg tttcatcact    5700
tttttcagtg tgtaatcatc gtttagctca atcataccga gagcgccgtt tgctaactca    5760
gccgtgcgtt ttttatcgct ttgcagaagt ttttgacttt cttgacggaa gaatgatgtg    5820
cttttgccat agtatgcttt gttaaataaa gattcttcgc cttggtagcc atcttcagtt    5880
ccagtgtttg cttcaaatac taagtatttg tggcctttat cttctacgta gtgaggatct    5940
ctcagcgtat ggttgtcgcc tgagctgtag ttgccttcat cgatgaactg ctgtacattt    6000
```

```
tgatacgttt ttccgtcacc gtcaaagatt gatttataat cctctacacc gttgatgttc    6060
aaagagctgt ctgatgctga tacgttaact tgtgcagttg tcagtgtttg tttgccgtaa    6120
tgtttaccgg agaaatcagt gtagaataaa cggattttc cgtcagatgt aaatgtggct     6180
gaacctgacc attcttgtgt ttggtctttt aggatagaat catttgcatc gaatttgtcg    6240
ctgtctttaa agacgcggcc agcgttttc cagctgtcaa tagaagttc gccgactttt      6300 tgatagaaca tgtaaatcga tgtgtcatcc gcattttag gatctccggc taatgcaaag     6360
acgatgtggt agccgtgata gtttgcgaca gtgccgtcag cgttttgtaa tggccagctg    6420
tcccaaacgt ccaggccttt tgcagaagag atattttaa ttgtggacga atcaaattca     6480 gaacttgat attttcatt tttttgctgt tcagggattt gcagcatatc atggcgtgta      6540
atatgggaaa tgccgtatgt ttccttat ggcttttggt tcgtttcttt cgcaaacgct      6600
tgagttgcgc ctcctgccag cagtgcggta gtaaaggtta atactgttgc ttgttttgca    6660 aacttttga tgttcatcgt tcatgtctcc tttttatgt actgtgttag cggtctgctt      6720
cttccagccc tcctgtttga agatggcaag ttagttacgc acaataaaaa aagacctaaa    6780
atatgtaagg ggtgacgcca aagtatacac tttgccctt acacatttta ggtcttgcct     6840
gctttatcag taacaaaccc gcgcgattta cttttcgacc tcattctatt agactctcgt    6900
ttggattgca actggtctat tttcctcttt tgtttgatag aaaatcataa aaggatttgc    6960
agactacggg cctaaagaac taaaaaatct atctgtttct tttcattctc tgtatttttt    7020
atagtttctg ttgcatgggc ataaagttgc cttttaatc acaattcaga aaatatcata    7080
atatctcatt tcactaaata atagtgaacg gcaggtatat gtgatgggtt aaaaaggatc    7140
ggcggccgct cgatttaaat c                                               7161
```